United States Patent
St Amant et al.

(10) Patent No.: US 10,841,083 B2
(45) Date of Patent: Nov. 17, 2020

(54) SYSTEMS, DEVICES, AND/OR PROCESSES FOR OMIC CONTENT PROCESSING AND/OR COMMUNICATION

(71) Applicant: ARM Ltd., Cambridge (GB)

(72) Inventors: Renee Marie St Amant, Austin, TX (US); Peter James Samuel Ferguson, Cambridge (GB); Gary Dale Carpenter, Austin, TX (US); Brian Tracy Cline, Austin, TX (US)

(73) Assignee: ARM Ltd., Cambridge (GB)

( * ) Notice: Subject to any disclaimer, the term of this patent is extended or adjusted under 35 U.S.C. 154(b) by 207 days.

(21) Appl. No.: 15/922,738

(22) Filed: Mar. 15, 2018

(65) Prior Publication Data

US 2019/0288837 A1  Sep. 19, 2019

(51) Int. Cl.
*H04L 9/08* (2006.01)
*H04L 29/06* (2006.01)
*G16H 80/00* (2018.01)
*H04W 12/04* (2009.01)
*G16H 50/20* (2018.01)

(52) U.S. Cl.
CPC ........... *H04L 9/0827* (2013.01); *G16H 50/20* (2018.01); *G16H 80/00* (2018.01); *H04L 63/0428* (2013.01); *H04W 12/04* (2013.01)

(58) Field of Classification Search
CPC .................. H04L 63/0853; H04L 9/0828
See application file for complete search history.

(56) References Cited

U.S. PATENT DOCUMENTS

| 2003/0083822 | A2 | 1/2003 | Brunner et al. |
| 2008/0178284 | A1* | 7/2008 | Harwell ........... G11B 20/00275 726/21 |
| 2009/0117033 | A1* | 5/2009 | O'gara ............... A61K 51/1255 424/1.11 |
| 2010/0070455 | A1 | 3/2010 | Halperin et al. |
| 2012/0084193 | A1* | 4/2012 | Marino ................. G06Q 40/04 705/37 |
| 2012/0221350 | A1 | 8/2012 | Kennedy et al. |
| 2012/0230326 | A1 | 9/2012 | Ganeshalingam et al. |

(Continued)

FOREIGN PATENT DOCUMENTS

| WO | 2012122555 A2 | 9/2012 |
| WO | 2012122555 A3 | 9/2012 |
| WO | 2017079828 A1 | 5/2017 |

OTHER PUBLICATIONS

ETHzürich Wearable devices, Screenshots of youtube video, www.youtube.com/watch?v=Qi34rm0gSZA, retrieved Nov. 28, 2018, 15 pages.

(Continued)

*Primary Examiner* — Ali Shayanfar
(74) *Attorney, Agent, or Firm* — Berkeley Law & Technology Group, LLP

(57) ABSTRACT

Subject matter disclosed herein may relate to at least one processor to establish a communication connection between a portable computing device and a particular external device, the at least one processor to initiate transmission of one or more signal packets representative of one or more communication, security, and/or cryptographic parameters to the particular external device responsive at least in part to the establishing the communication connection.

20 Claims, 23 Drawing Sheets

(56) References Cited

U.S. PATENT DOCUMENTS

| | | | | |
|---|---|---|---|---|
| 2013/0062156 | A1* | 3/2013 | Chandaria | G07F 1/06 |
| | | | | 194/339 |
| 2013/0130360 | A1 | 5/2013 | Ho et al. | |
| 2013/0323306 | A1* | 12/2013 | Weber | A61P 35/00 |
| | | | | 424/489 |
| 2014/0089348 | A1* | 3/2014 | Vollmert | G06F 16/00 |
| | | | | 707/785 |
| 2014/0160519 | A1* | 6/2014 | Jeran | G06F 3/1203 |
| | | | | 358/1.14 |
| 2014/0245373 | A1* | 8/2014 | Martin | H04L 63/104 |
| | | | | 726/1 |
| 2016/0249864 | A1 | 9/2016 | Kang et al. | |
| 2016/0314460 | A1* | 10/2016 | Subramanian | G06Q 20/12 |
| 2018/0001184 | A1* | 1/2018 | Tran | A63B 43/004 |
| 2018/0010197 | A1* | 1/2018 | Beane-Ebel | C12Q 1/6886 |
| 2018/0070199 | A1* | 3/2018 | Buck | H04W 4/80 |
| 2018/0103042 | A1* | 4/2018 | Castagna | H04L 63/08 |
| 2019/0000754 | A1* | 1/2019 | Huang | A61K 9/0048 |

OTHER PUBLICATIONS

Epigenetic Mechanisms Chart, https://commonfund.nih.gov/sites/default/files/epigeneticmechanisms.pdf, retrieved Jan. 23, 2019, 1 page.

Kohler et. al.; "Plant epigenomics—deciphering the mechanisms of epigenetic inheritance and plasticity in plants"; Genome Biology; Jul. 6, 2017, 3 pages.

Notification of Transmittal of the International Search Report and the Written Opinion of the International Searching Authority, or the Declaration, dated May 31, 2019, International Application No. PCT/GB2019/050692, 1 pg.

International Search Report, dated May 31, 2019, International Application No. PCT/GB2019/050692, 5 pgs.

Written Opinion of the International Searching Authority, dated May 31, 2019, International Application No. PCT/GB2019/050692, 15 pgs.

Akashi, et. al., "Noninvasive method for assessing the human circadian clock using hair follicle cells", PNAS, Aug. 31, 2010, vol. 107, No. 35, pp. 15643-15648.

Akashi, et. al., "Supporting Information. Noninvasive method for assessing the human circadian clock using hair follicle cells", Proceedings of the National Academy of Sciences of the United States of America, vol. 107, No. 35, Aug. 23, 2010, 9 pgs.

Non-Final Office Action dated Feb. 4, 2020, U.S. Appl. No. 15/922,755, 36 pages.

Response to Non Office Action filed May 4, 2020, U.S. Appl. No. 15/922,755, 25 pages.

Non-Final Office Action dated Jan. 17, 2020, U.S. Appl. No. 15/922,771, 33 pages.

Response to Non-Final Office Action filed Apr. 17, 2020, U.S. Appl. No. 15/922,771, 46 pages.

Final Office Action, U.S. Appl. No. 15/922,771, dated Jun. 19, 2020, 25 Pages.

Response to Final Office Action, U.S. Appl. No. 15/922,771, filed Aug. 19, 2020, 26 Pages.

Advisory Action, U.S. Appl. No, 15/922,771, dated Sep. 2, 2020, 13 Pages.

Notice of Allowance, U.S. Appl. No. 15/922,755, dated Jul. 2, 2020, 19 Pages.

Notification Concerning Transmittal of International Preliminary Report on Patentability, App. No. PCT/GB2019/050692, dated Sep. 24, 2020, 1 Page.

International Preliminary Report on Patentability, App. No. PCT/GB2019/050692, dated Sep. 24, 2020, 1 Page.

Written Opinion of the International Searching Authority, App. No. PCT/GB2019/050692, dated Sep. 24, 2020, 12 Pages.

RCE Amendment, U.S. Appl. No 15/922,771, filed Sep. 21, 2020, 28 Pages.

* cited by examiner

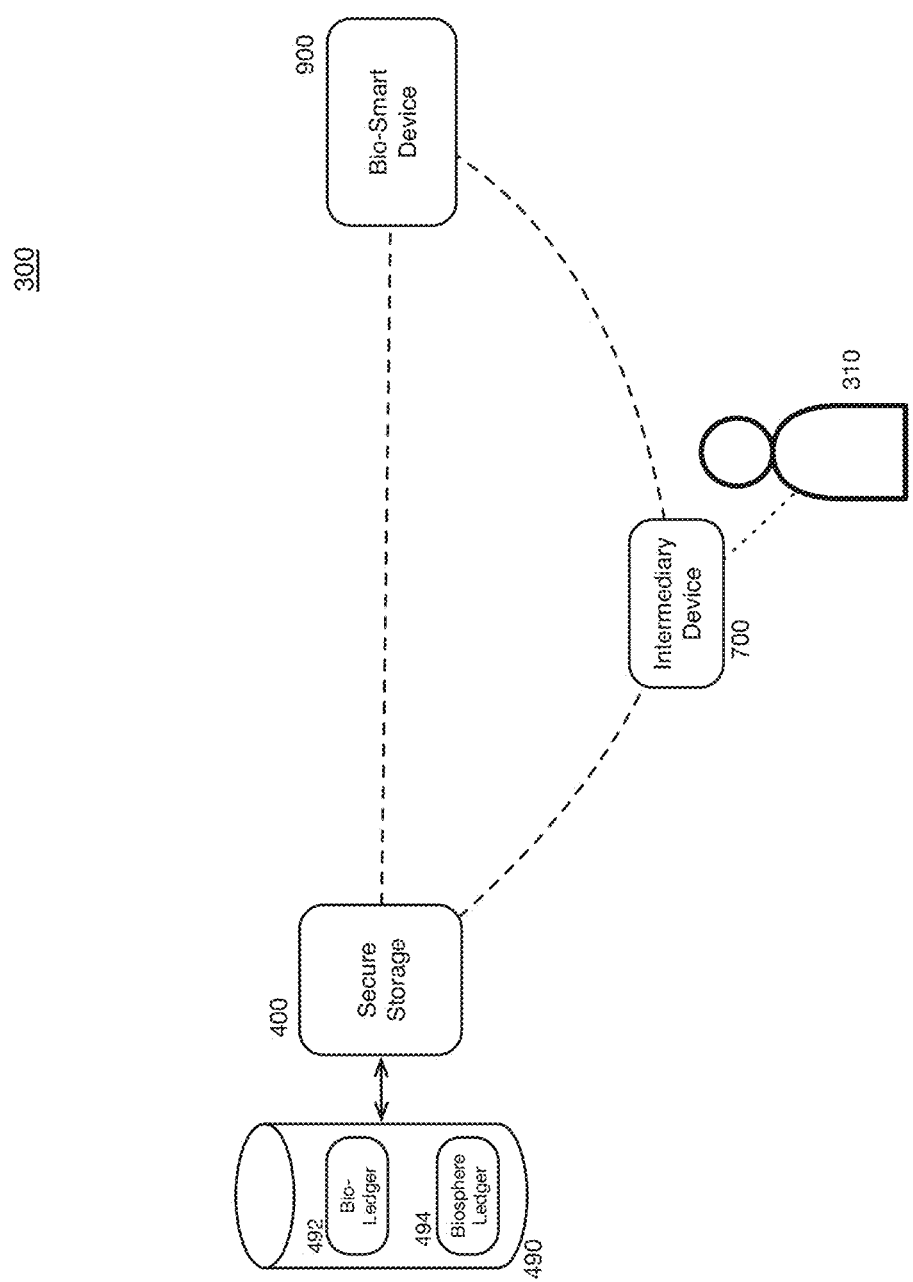

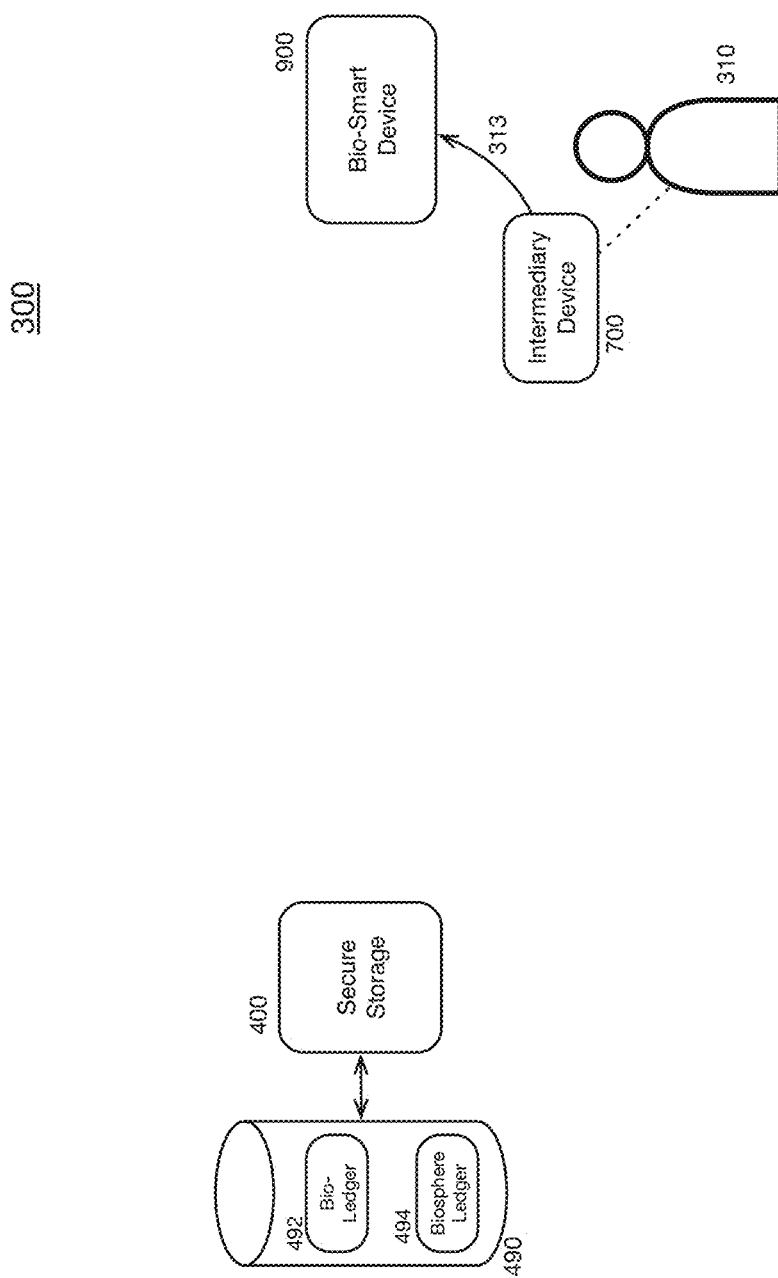

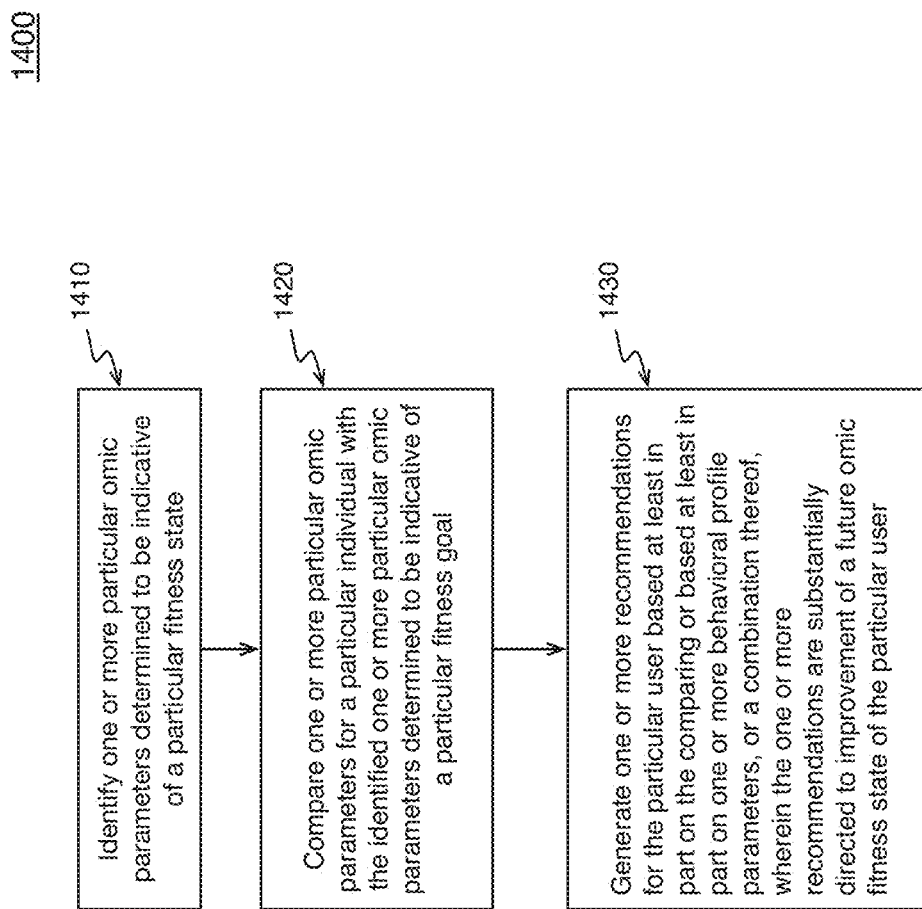

US 10,841,083 B2

SYSTEMS, DEVICES, AND/OR PROCESSES FOR OMIC CONTENT PROCESSING AND/OR COMMUNICATION

RELATED APPLICATIONS

This patent application is related to U.S. Ser. No. 15/922,721 entitled Systems, Devices, and/or Processes for Omic and/or Behavioral Content Processing; U.S. Ser. No. 15/922,755 entitled Systems, Devices, and/or Processes for Omic Content Processing and/or Partitioning; and U.S. Ser. No. 15/922,771 entitled Systems, Devices, and/or Processes for Omic Content and/or Environmental Content Processing and/or Communication; all filed herewith, and all hereby incorporated by reference in their entirety.

BACKGROUND

Field

Subject matter disclosed herein relates to systems, devices, and/or processes for processing and/or communicating signals and/or states representative of omic content.

Information

Integrated circuit devices, such as processors, for example, may be found in a wide range of electronic device types. For example, one or more processors may be used in mobile devices, such as cellular phones, for example, as well as in server computers, personal computers, digital cameras, tablet devices, personal digital assistants, wearable devices, etc. Mobile devices and/or other computing devices, for example, may include integrated circuit devices, such as processors, to process signals and/or states representative of a diverse of content types for a variety of purposes. With an abundance of diverse content being accessible, signal and/or state processing techniques continue to evolve. At times, however, processing signals and/or states representative of diverse content may prove to be relatively resource-demanding, which may present a number of challenges including, for example, increased processing time, storage demands, complexity, cost, and/or the like.

BRIEF DESCRIPTION OF THE DRAWINGS

Claimed subject matter is particularly pointed out and distinctly claimed in the concluding portion of the specification. However, both as to organization and/or method of operation, together with objects, features, and/or advantages thereof, it may best be understood by reference to the following detailed description if read with the accompanying drawings in which:

FIG. 3a is a schematic block diagram depicting an example device, system, and/or process for communication and/or processing of epigenetic content, in accordance with an embodiment.

FIG. 3c is a schematic block diagram depicting an example communication of parameters between an intermediary device and a bio-smart device, in accordance with an embodiment.

FIG. 14 is an illustration of an example process for generating recommendations directed to improvement of a future epigenetic fitness state of a particular individual, in accordance with an embodiment.

Figure 1:
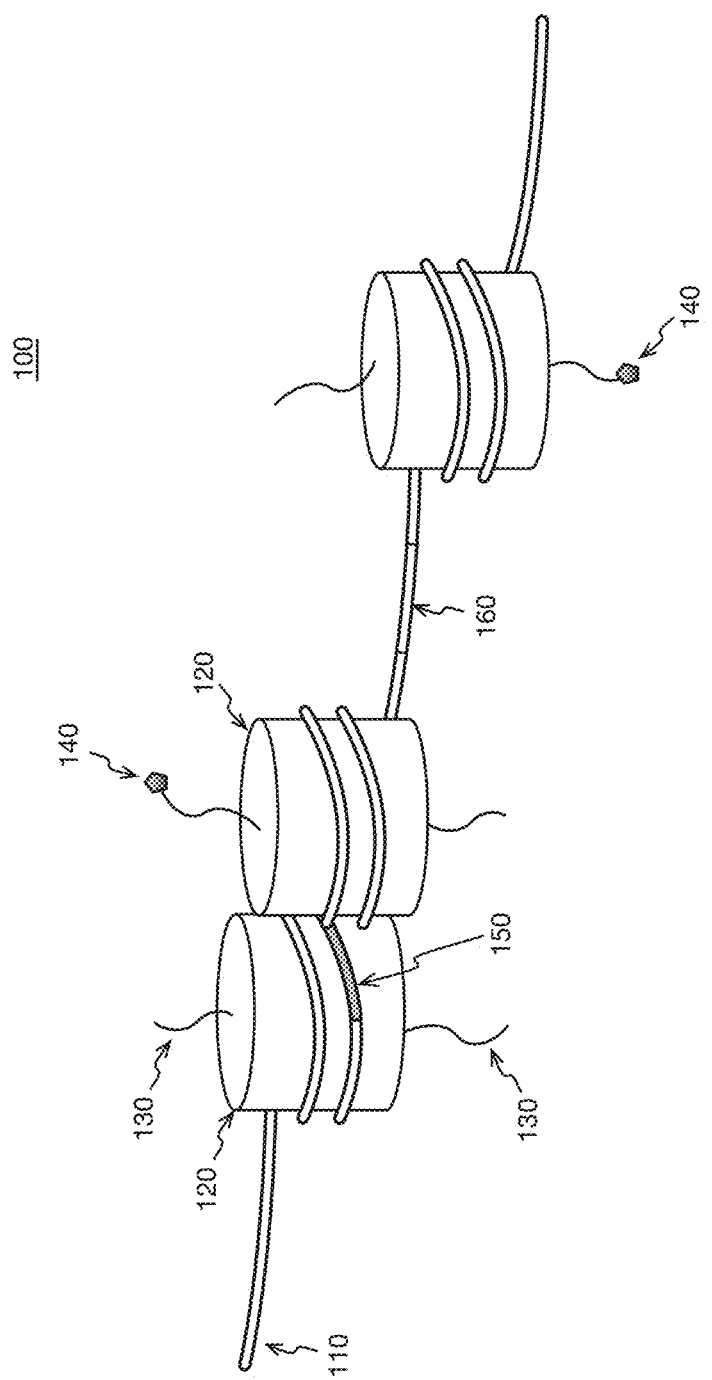
FIG. 1 is an illustration depicting an example DNA portion, in accordance with an embodiment.

Reference is made in the following detailed description to accompanying drawings, which form a part hereof, wherein like numerals may designate like parts throughout that are corresponding and/or analogous. It will be appreciated that the figures have not necessarily been drawn to scale, such as for simplicity and/or clarity of illustration. For example, dimensions of some aspects may be exaggerated relative to others. Further, it is to be understood that other embodiments may be utilized. Furthermore, structural and/or other changes may be made without departing from claimed subject matter. References throughout this specification to "claimed subject matter" refer to subject matter intended to be covered by one or more claims, or any portion thereof, and are not necessarily intended to refer to a complete claim set, to a particular combination of claim sets (e.g., method claims, apparatus claims, etc.), or to a particular claim. It should also be noted that directions and/or references, for example, such as up, down, top, bottom, and so on, may be used to facilitate discussion of drawings and are not intended to restrict application of claimed subject matter. Therefore, the following detailed description is not to be taken to limit claimed subject matter and/or equivalents.

DETAILED DESCRIPTION

References throughout this specification to one implementation, an implementation, one embodiment, an embodiment, and/or the like means that a particular feature, structure, characteristic, and/or the like described in relation to a particular implementation and/or embodiment is included in at least one implementation and/or embodiment of claimed subject matter. Thus, appearances of such phrases, for example, in various places throughout this specification are not necessarily intended to refer to the same implementation and/or embodiment or to any one particular implementation and/or embodiment. Furthermore, it is to be understood that particular features, structures, characteristics, and/or the like described are capable of being combined in various ways in one or more implementations and/or embodiments and, therefore, are within intended claim scope. In general, of course, as has always been the case for the specification of a patent application, these and other issues have a potential to vary in a particular context of usage. In other words, throughout the patent application, particular context of description and/or usage provides helpful guidance regarding reasonable inferences to be drawn; however, likewise, "in this context" in general without further qualification refers to the context of the present patent application.

As mentioned, integrated circuit devices, such as processors, for example, may be found in a wide range of electronic device types. For example, one or more processors may be used in mobile devices, such as tablet devices and/or cellular phones, for example, as well as in server computers, personal computers, digital cameras, tablet devices, personal digital assistants, wearable devices, etc. Mobile devices and/or other computing devices, for example, may include integrated circuit devices, such as processors, to process signals and/or states representative of a diverse of content types for a variety of purposes. With an abundance of diverse content being accessible, signal and/or state processing techniques continue to evolve. At times, however, processing signals and/or states representative of diverse content may prove to be relatively resource-demanding, which may present a number of challenges including, for example, increased processing time, storage demands, complexity, cost, and/or the like.

In some circumstances, integrated circuit devices, such as processors, for example, may be employed in computing devices, for example, to perform tasks that may be beneficial in managing and/or improving a biological, behavioral, and/or emotional state of an individual. For example, embodiments may analyze and/or otherwise process epigenetic content and/or other content types (e.g., parameters indicative of environmental factors, behavioral factors, etc.) to detect and/or predict changes in an epigenetic state for a particular individual. In some embodiments, potentially undesirable changes in epigenetic state may be detected and/or predicted, and/or recommendations may be generated with a goal of improving an epigenetic state of a particular individual.

"Omics" and/or the like generally refers to biological fields of study, such as genomics, proteomics, metabolomics, epigenomics, microbiomics, etc. Herein, "omic content" and/or the like refers to epigenetic, microbiome, proteome, metabolome, or transcriptome content, or any combination thereof. Embodiments may also involve genomic content. "Epigenetic content" refers to signals and/or states representative of one or more epigenetic parameters. Epigenetic and/or other omic content, for example, may be transmitted and/or received as signals and/or states (e.g., signal packets) physically propagated over a network, such as the Internet. Further, epigenetic and/or other omic content may be stored as signals and/or states in a memory, for example. "Epigenetic" in some cases and/or contexts refers to bio-markers that may sit on top of particular genes within animal, such as human, and/or plant deoxyribonucleic acid (DNA). Further, in some cases, epigenetic bio-markers may be measured through a technique similar to genetic sequencing. Epigenetic parameters, for example, may be representative of one or more particular bio-markers that may result in a particular gene expression (e.g., which particular genes are turned on and/or turned off). For example, a bio-marker may sit on top of a genome and may change that particular genome's function. Example mechanisms for changing a genome's function may include, but are not limited to, attachment of a methyl group comprising a carbon atom and three carbon atoms ($CH_3$) to one or more segments of DNA, and/or histone modification. Epigenetic mechanisms may encompass a number of pre-transcriptional to post-translational events involving chromatin structure, methylation, non-coding ribonucleic acids (RNA), and/or histone modification, for example. Subject matter is not limited in scope in these regards.

FIG. 1, for example, depicts an example illustration 100 of an example DNA portion, such as DNA portion 100. As depicted in FIG. 1, an example DNA portion, such as DNA portion 110, may include example histones 120 and/or example histone tails 130. Histones, such as example histones 120, may comprise proteins around which DNA may wind, such as for compaction and/or gene regulation, for example. Histone modification may involve, in some circumstances, the binding of epigenetic factors, such as example epigenetic factors 140, to histone tails, such as example histone tails 130. For example, a binding of epigenetic factors to histone tails may alter an extent to which DNA may be wrapped around histones and/or may alter an extent to which the availability of genes, such as example genes 150 and/or 160, in the DNA may be activated. For example, one or more epigenetic factors 140 may bind to one or more histone tails 130, and as a result, at least in part, one or more genes 150 may be deactivated.

Additionally, DNA methylation may occur, for example, in response to methyl groups (e.g., as produced by the body and/or consumed in some dietary source, such as in the form of 5-methyltetrahydrofolate) tagging DNA and/or activating and/or repressing particular genes. Epigenetic mechanisms may be affected at least in part by any of several example factors and/or processes including, but not limited to, development in utero and/or in childhood, environmental chemicals, drugs and/or pharmaceuticals, aging, diet, etc. Epigenetic factors and/or processes may generally have an effect on people's health, potentially resulting in some situations in cancer, autoimmune disease, mental disorders, and/or diabetes, to name but a few examples. The term "exposome" may refer to a measure of cumulative exposures of an individual over the course of a lifetime and/or how those exposures may relate to the health of an individual. An individual's exposure may begin before birth and/or may include effects from environmental and/or occupational sources, for example. Such exposure may influence, for example, epigenome, microbiome, proteome, metabolome, transcriptome, and/or other states that may impact, adversely and/or otherwise, an individual's health and/or wellbeing.

While an individual's genes typically may not change during a lifetime, epigenetic bio-markers, such as example epigenetic factors 140, may change based at least in part on environmental factors in some circumstances. For example, epigenetic changes may occur due at least in part to climate, diet, exercise, environmental toxins, etc. Science has determined some epigenetic indicators of particular diseases, such as various cancers and/or diabetes, as well as epigenetic indicators of societally-relevant conditions such as addiction, risk of suicide, etc., for example. Further, science has determined that at least some epigenetic characteristics may be transferred from individuals to their offspring in a process referred to as "epigenetic inheritance" and/or "transgenerational epigenetic inheritance."

Although some embodiments described herein mention epigenetic content, embodiments are not restricted to epigenetic content, but rather may include other "omic" content. As mentioned, "omics" and/or the like in this context generally refers to biological fields of study, such as genomics, proteomics, metabolomics, epigenomics, microbiomics, etc. Herein, "omic content" and/or the like refers to epigenetic, microbiome, proteome, metabolome, or transcriptome content, or any combination thereof. As also mentioned, embodiments may also involve genomic content. In an embodiment, as more detailed and/or comprehensive epigenetic and/or other omic content becomes available for individuals, it may be beneficial to make such content, and/or particular portions of such content, available to electronic devices configured to process epigenetic and/or other omic content to an individual's benefit, for example. In an embodiment, for example, it may be advantageous to have an electronic device determine what particular levels of body fat may be harmless for a particular individual. For another example, it may be beneficial to have an electronic device detect whether a decline in cognitive function may be a result of fatigue and/or whether a decline may be a result of early-onset dementia. In a further example, it may be advantageous for an electronic device to determine whether a change in epigenetic markers may be presaged by changes in particular air particulates and/or by an introduction of different dietary elements. Challenges related to implementing such devices, systems, and/or processes may include, for example, enabling electronic devices to access particular sensitive, private, and/or confidential content while achieving a desired level of security in storing and/or communicating sensitive, private, and/or confidential content. An additional example challenge may include development of a recommended, standardized, and/or otherwise specified manner of tracking, monitoring, storing, and/or representing, for example, an individual's environmental influencers such that science and/or analytics, for example, may continue to determine relationships and/or correlations between an individual's environmental factors and changes in personal biological content, for example.

Embodiments may include devices, systems, and/or processes for relatively securely storing content, such as epigenetic and/or other omic content, for one or more particular individuals and/or for relatively securely communicating content, such as epigenetic content, to various devices, for example. Example embodiments described herein may further be directed to devices, systems, and/or processes that may enable, at least in part, and/or may include, one or more "bio-smart" devices. "Bio-smart," and/or "bio-smart device" and/or the like refer to the use of personal biological (e.g., omic) content by a computing device, for example, to help manage and/or improve a biological, behavioral, and/or emotional state of an individual. As described more fully below, bio-smart devices may, in embodiments, interact with an individual's bio-ledger and/or biosphere ledger in a relatively secure manner. In embodiments, a bio-smart device may relatively securely interact with an individual's bio-ledger and/or biosphere ledger with help from an intermediary device, as also explained more fully below. For bio-smart devices, interactions with an individual's bio-ledger and/or biosphere ledger may include, for example, reading and/or writing. By contrast, logging-type devices, more fully described below, may write content (e.g., environmental measurement parameters) to a storage device, such as secure storage device, but may not, in an embodiment, read from a bio-ledger and/or biosphere ledger. In an embodiment, as described more fully below, a logging-type device may write content to a secure storage device, for example, and the secure storage device may store obtained content in one or more individual's bio-ledger and/or biosphere ledger. A secure storage device may also, for example, store satellite positioning system (e.g., GPS) location parameters associated with content obtained from a logging-type device in one or more individual's bio-ledger and/or biosphere ledger. Embodiments may employ machine learning and/or other content analytic techniques to leverage personal biological content, such as epigenetic and/or other omic content, for example, to help, at least in part, one or more particular individuals to improve their biological, behavioral, and/or emotional states.

Embodiments may enable electronic devices, such as bio-smart devices, to request and/or access subsets of personal biological content measured, determined, and/or otherwise gathered at one or more previous points in time, for example. Embodiments may further include coordinated and/or timestamped snapshots of an individual's biological content and/or content representative of environmental influencers to enable, at least in part, additional understanding of relationships and/or correlations between changes in biological state of an individual and environmental influencers, for example. Further, embodiments may include aggregation of an individual's biological and/or environmental influencer content, for example, that may result at least in part from an increase in numbers of environmental sensors and/or an increase in particular medical testing. In an embodiment, content may be aggregated in a recommended, standardized, and/or otherwise specified manner, for example.

For example, in an embodiment, epigenetic and/or other omic content (e.g., microbiome, proteome, metabolome, and/or transcriptome content) pertaining to a particular individual may be obtained, wherein the epigenetic and/or other omic content may be representative of one or more particular epigenetic and/or other omic states for the particular individual at respective points in time. In an embodiment, epigenetic content may include parameters indicative of particular bio-markers associated with particular gene expressions, for example. Embodiments may analyze and/or otherwise process epigenetic content and/or other content types (e.g., parameters indicative of environmental factors, behavioral factors, etc.) to detect and/or predict changes in epigenetic state for a particular individual. In some embodiments, potentially undesirable changes in epigenetic state may be detected and/or predicted, and/or recommendations may be generated with a goal of improving an epigenetic state of a particular individual. As mentioned, although embodiments may, for ease of discussion, describe epigenetic content, claimed subject matter is not limited in scope in this respect. For example, embodiments may include epigenetic, microbiome, proteome, metabolome, or transcriptome content, or any combination thereof.

In at least some embodiments, content, such as may be obtained from one or more sensors, for example, may be processed to generate content, such as behavioral profile content, for one or more individuals. In embodiments, behavioral profile content may be analyzed and/or otherwise processed in combination with epigenetic content, for example, to detect and/or predict changes in epigenetic state for one or more individuals. Further, in embodiments, content, such as behavioral profile content for one or more individuals, may be analyzed and/or otherwise processed in combination with epigenetic content, for example, to generate recommendations with respect to one or more individuals. In embodiments, recommendations may be directed at improving a current and/or future epigenetic state of one or more individuals. In other embodiments, content, such as behavioral profile content for a particular individual, may be analyzed and/or otherwise processed in combination with epigenetic content, for example, to generate recommendations for a particular individual directed to the particular individual's behavioral and/or biological state.

In an embodiment, content obtained from one or more sensors may be processed by particular hardware circuitry to generate behavioral profile content representative of a particular individual's physical, mental, and/or emotional state. For example, a processor, such as a behavioral processing unit, may be dedicated, at least in part, to processing sensor content to generate behavioral profile content representative of a particular individual's physical, mental, and/or emotional state. A processor, such as a behavioral processing unit, may include particular circuitry directed to performing particular operations to relatively more efficiently process sensor content to generate behavioral profile content for a particular individual, in an embodiment. For example, in an embodiment, a processor, such as a behavioral processing unit, may include machine learning acceleration circuitry directed to performing particular operations that may relatively more efficiently operate on sets of parameters, such as multi-dimensional sets of parameters, that may be utilized in various machine learning techniques such as, for example, neural networks, as discussed more fully below. In an embodiment, a processor, such as a behavioral processing unit, may comprise a co-processor, for example, that may operate in cooperation with a general-purpose processor, although subject matter is not limited in this respect.

The terms "individual," "operator," and/or "user" refer to human individuals and/or may be utilized herein interchangeably. In some contexts, such as related to agricultural applications, an "individual" may comprise a particular plant, crop, and/or farm, for example. Further, as utilized herein, "behavioral profile content" and/or the like refers to one or more parameters representative of a behavioral, physical, mental, and/or emotional state for at least one particular individual (e.g., human and/or plant). Thus, for example, "behavioral profile content" and/or the like is not limited to merely behavioral aspects of a particular individual's state, but may also include parameters representative of one or more biological aspects with respect to a particular individual, as explained more fully herein. Further, although some embodiments herein may be described in connection with "an" individual and/or "a" particular individual, subject matter is not limited to a single individual. For example, at least some embodiments may include behavioral profile content for one or more individuals, although, again, subject matter is not limited in scope in these respects. Also, content refers to physical signals and/or states that may be transmitted and/or received, for example, via wired and/or wireless interconnects and/or via one or more networks. Signals and states comprising content may also be stored in a memory and/or a mass storage device, for example. Example communication technologies and/or example physical media by which content, such as omic and/or behavioral profile content, may be transmitted, received, and/or stored, for example, are mentioned below.

Further, as utilized herein, the term "current" and/or the like refers to substantially and/or approximately current with respect to a point in time. For example, a "current" behavioral and/or biological state of a particular individual refers to a behavioral and/or biological state for the particular individual derived at least in part from relatively recent sensor content. For example, in an embodiment, behavioral profile content for a particular individual may be representative of a behavioral and/or biological state of the particular individual derived at least in part from sensor content obtained from one or more sensors within fractions of a second of being generated.

Figure 2:
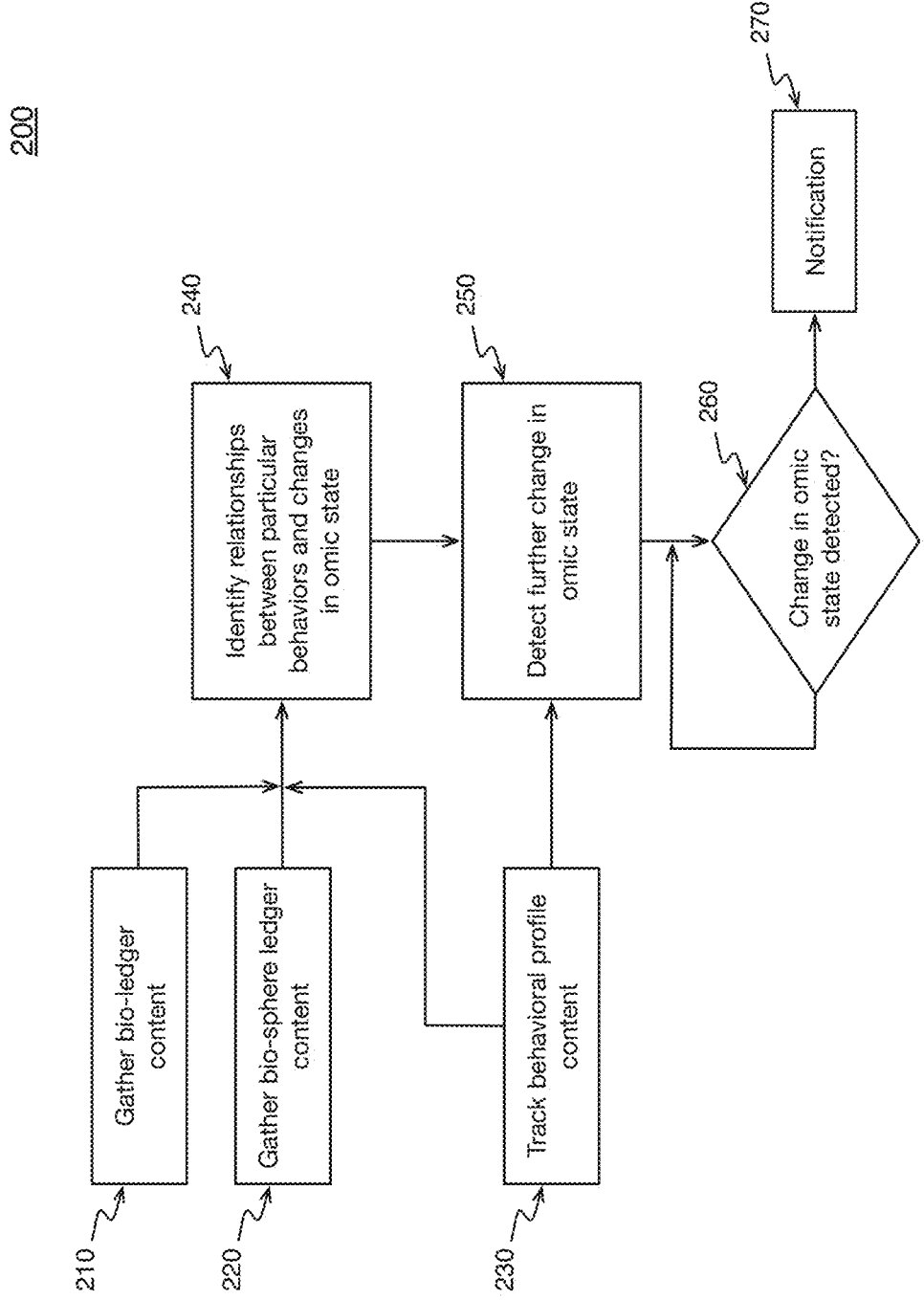
FIG. 2 is an illustration of an example process for detecting a change in epigenetic state, in accordance with an embodiment.

FIG. 2 is an illustration of an example process for detecting a change in epigenetic state, in accordance with an embodiment. Embodiments in accordance with claimed subject matter may include all of blocks 210-270, fewer than blocks 210-270, and/or more than blocks 210-270. Further, the order of blocks 210-270 is merely an example order, and subject matter is not limited in scope in these respects. As depicted at blocks 210 and/or 220, epigenetic content, such as in the form of bio-ledger content and/or biosphere ledger content, may be gathered and/or otherwise obtained for one or more individuals. In an embodiment, an electronic device, such as a bio-smart device and/or a secure storage device, as discussed more fully below, may receive signals and/or states comprising omic content, for example, from one or more devices. In an embodiment, content, such as omic content, may be transmitted and/or received via wired and/or wireless network connections. For example, omic content, such as bio-ledger content and/or biosphere ledger content, may be transmitted and/or received via signal packet communications and/or signal frame communications, also referred to as signal packet transmissions and/or signal frame transmissions (or merely "signal packets" or "signal frames"). In an embodiment, signal packets and/or signal frames, for example, may be communicated between nodes of a network, where a node may comprise one or more network devices and/or one or more computing devices, for example. As discussed more fully below, epigenetic content and/or other content types, such as behavioral profile content, may be analyzed and/or otherwise processed at least in part to detect and/or predict changes in epigenetic state for one or more individuals. In an embodiment, a computing device may include one or more processors, such as one or more behavioral processing units, discussed below. In an embodiment, behavioral profile content may be written to an individual's bio-ledger and/or biosphere ledger, which may include a computing device, such as a bio-smart device, transmitting via signal packet communication and/or signal frame communication, for example, parameters representative of omic content to be stored at a secure storage device. Further, in an embodiment, epigenetic and/or other omic content may be processed via one or more processors at least in part to detect and/or predict changes in epigenetic state, as explained more fully below.

To analyze and/or otherwise process epigenetic content, a device, system, and/or process may request subsets of epigenetic content for one or more particular individuals from previous points in time. Machine learning and/or other analytic techniques may benefit from generation of coordinated and/or time-stamped snapshots of a individual's epigenetic content and/or time-stamped snapshots of a individual's behavioral profile content, and/or may also benefit from coordinated and/or time-stamped snapshots of environmental factors corresponding to a individual's epigenetic content. Embodiments may further employ environmental sensors and/or medical (e.g., genetic, biological, etc.) testing to gather, over a period of time, epigenetic content and/or content representative of environmental factors for one or more individuals. In an embodiment, epigenetic and/or other omic content may be gathered, for example, by receiving signals and/or states at a communication interface of an electronic device and/or by storing the received signals and/or states in a non-transitory memory. Epigenetic and/or environmental content for one or more individuals may be configured in a manner relatively more conducive to identification of relationships, correlations, etc. between epigenetic changes and/or environmental factors. As mentioned, embodiments are not restricted to epigenetic content, but may also include other types of omic content (e.g., microbiome, proteome, metabolome, and/or transcriptome content).

For example, as suggested at blocks 210 and/or 220, personal bio-ledgers and/or personal biosphere ledgers may be generated from epigenetic, and/or environmental content for a particular individual. As utilized herein, "Bio-ledger" refers to entries of parameters representative of one or more aspects of one or more individual's internal biological state stored in at least one non-transitory medium and/or memory of at least one computing device. In an embodiment, bio-ledger entries may be time-stamped. For example, time-stamped entries may correspond, at least in part, to one or more aspects of an individual's internal biological state at particular points in time, for example. In an embodiment, bio-ledger entries may include parameters representative of one or more aspects of genetic content, epigenetic content, microbiome content, or proteome content, metabolome content, and/or transcriptome content, or any combination thereof, to name several non-limiting examples. Bio-ledger entries may further include, for example, lab test content for an individual, content representative of diagnosed diseases for an individual, identified risk factors for an individual, etc. In an embodiment, a bio-ledger may include entries for any number of particular individuals and/or for a population of individuals, for example. In an embodiment, a bio-ledger may be indexed within at least one memory of a computing device on a per-individual basis. Further, particular individuals may be associated with more than one bio-ledger and/or biosphere ledger. For example, different bio-ledgers and/or biosphere ledgers for an individual may incorporate varying security characteristics and/or permissions, in an embodiment.

Further, as utilized herein, "biosphere ledger" refers to entries of parameters representative of one or more environmental aspects related to one or more particular individuals stored in at least one non-transitory medium and/or memory of at least one computing device. Environmental aspects may include, for example, environmental exposures (e.g., air and/or water pollutants), lifestyle (e.g., media consumption, diet, exercise, medications, etc.), and/or behavioral (e.g., behavioral profile content). "Environmental content" refers to one or more parameters indicative of one or more particular environmental aspects related to one or more particular individuals. "Lifestyle content" and/or the like refers to one or more parameters indicative of one or more particular lifestyle aspects related to one or more particular individuals. Example types of lifestyle content may include parameters representative of an individual's diet (e.g., food, beverages, supplements, etc.), media consumption (e.g., media type, media title, media genre, etc.), medications, and/or exercise habits, routines, and/or experiences, although claimed subject matter is not limited in scope in these respects. In an embodiment, a biosphere ledger may include parameters indicative environmental context for one or more entries of a bio-ledger. For example, one or more bio-ledger entries may indicate a change in epigenetic and/or other omic state for a particular individual. In embodiment, one or more entries of a biosphere ledger may indicate an environmental context in which a change in epigenetic and/or other omic state may have occurred. For example, a bio-ledger may indicate one or more changes in epigenetic state for a particular individual, and a biosphere ledger may include air quality measurements taken at points in time relevant to the indicated changes in epigenetic state. Further, for example, behavioral profile content may indicate repeated anger states for an individual, and such states may be found to relate to particular changes in epigenetic and/or other omic states for the individual.

In embodiments, separate databases and/or portions of databases for bio-ledger content and/or biosphere content may allow for different security and/or communication considerations and/or implementations, for example, for the different content. Bio-ledger content and/or biosphere ledger content may be stored in separate non-transitory media and/or memory devices, for example, and/or in separate portions of a non-transitory medium and/or memory. For example, certified laboratories, hospitals, doctor's offices, etc., may be permitted to write to an individual's bio-ledger. Similarly, at-home medical devices, for example, may also be permitted to write to an individual's bio-ledger. Further, in an embodiment, particular electronic devices, such as a bio-smart device, may be permitted to read from, but not write to, an individual's bio-ledger, for example, at least in part to improve an electronic device's offerings with respect to a particular individual. In some embodiments, relatively simple logging-type devices, for example, may be restricted to merely logging/writing content to an individual's biosphere ledger, as discussed more fully below. Additionally, software services, implemented, for example, on one or more computing devices, may log content to an individual's biosphere ledger. For example, air-quality measurements and/or ultra-violet (UV) radiation level measurements for particular times and/or locations may be obtained from publicly-available content and/or may be written to an individual's biosphere ledger. In other embodiments, behavioral profile content may be written to an individual's biosphere ledger, for example. Of course, subject matter is not limited in scope in these respects. In an embodiment, bio-ledger content and/or biosphere content may be written and/or recorded to a secure storage device, for example, at least in part via wired and/or wireless network communication between a computing device, such as a bio-smart device (discussed below) and a secure storage device.

In an embodiment, a goal of gathering and/or storing biosphere ledger content may include tracking histories of environmental influences to which one or more individuals may be exposed. Example environmental influencers may include, but are not limited to, exposure to monitored environmental conditions (e.g., air quality, ultra-violet radiation, noise pollution, etc.), substances consumed by an individual (e.g., an individual's diet), and/or media content consumed by an individual (e.g., watching particular television shows, reading a particular book, etc.). In an embodiment, biosphere ledger entries may be time-stamped. For example, a parameter indicative of a particular time of measurement may be stored in a biosphere ledger in connection with a particular air quality measurement parameter. A number of measurements may be taken and/or measurement parameters stored over a period of time, for example. In an embodiment, a biosphere ledger may include entries for any number of particular individuals and/or for one or more populations of individuals, for example. In an embodiment, biosphere ledger entries may be indexed on a per-individual basis to permit retrieval of particular entries pertaining to a particular individual, for example.

In an embodiment, one or more biosphere ledger entries may include a respective metric of influence parameter. "Metric of influence" in this context refers to a degree of relevance to a particular individual. In an embodiment, a metric of influence parameter may be representative of a measure of relevance with respect to a particular biosphere ledger entry. Further, in an embodiment, a metric of influence parameter may be determined based at least in part on a distance factor, a frequency factor, or a relative granularity factor, or any combination thereof. For example, a distance factor may indicate a measure of proximity to a particular sensor for an individual for a corresponding biosphere entry for the particular individual. For example, an air quality measurement taken by an air filter device within an individual's home may be assigned a greater relevance score with respect to a distance factor than would an air quality measurement taken at a regional airport.

Also, for example, a frequency factor may indicate a frequency at which particular measurements are taken. In an embodiment, an appropriate frequency of measurement may be dependent on the nature of the measurement. For example, with respect to rainfall measurements, it may be more advantageous to measure hourly rather than monthly. However, per-second measurements may not be desirable. In an embodiment, a frequency factor of a metric of influence may be assigned a value based at least in part on how closely a rate of measurement matches a rate of change in the subject being measured, although subject matter is not limited in scope in this respect. Also, in an embodiment, a relative granularity factor may include an indication of appropriateness for a particular measurement for a particular individual. For example, while a county-level smog count may be a relatively good gauge of particulate consumption for a particular individual, another individual's smart e-cigarette may be assigned a relatively higher relative granularity factor for that particular individual due at least in part to known consumption of particulates from the electronic cigarette.

Further, in an embodiment, one or more biosphere ledger entries may include parameters indicative of consent and/or permission. For example, because in some situations multiple sources may have access to a biosphere ledger, individual entries of a biosphere ledger may include parameters representative of particular privacy levels that may provide consent and/or permission to particular devices to access the biosphere entries. For example, parameters indicative of consent to access particular entries within a biosphere ledger may include content identifying one or more particular devices and/or one or more particular individuals that have been granted permission to access the particular entries. Any devices and/or individuals attempting to access particular entries without such consent may be denied access.

Additionally, in an embodiment, one or more biosphere entries may include one or more parameters indicative of a location associated with one or more environmental measurements. For example, air quality measurement parameters may be stored within a biosphere ledger along with parameters indicating locations of measurement devices involved in taking the measurements. In an embodiment, location parameters may include satellite positioning system (e.g., GPS) coordinates, although subject matter is not limited in scope in this respect.

Also, in an embodiment, one or more biosphere entries may include one or more parameters representative of a tangibility metric. In an embodiment, some devices, systems, and/or processes may contribute relatively less tangible, and/or perhaps relatively less proven, influencer content. For example, influencer factors associated with exposure to stress and/or events with potential emotional consequences may be assigned a tangibility metric that may indicate a reduced level of tangibility as compared with other relatively more tangible and/or relatively more proven influencer factors. In an embodiment, inclusion of relatively less tangible influencer factors in a biosphere ledger may help to mitigate false-positive correlations in machine learning models, for example. However, embodiments may also include parameters representative of a tangibility metric to identify, at least in part, biosphere entries that may be based at least in part on emotional rather than physical factors, subjective rather than objective factors, and/or values calculated via an algorithm rather than directly measured, for example. In an embodiment, a tangibility metric associated with respective biosphere ledger entries may allow for a relatively expanded concept of environment and/or environmental influencers.

Returning to FIG. 2, behavioral profile content may be tracked, as depicted at block 230. As described in more detail herein, behavioral profile content may be derived, at least in part, from content obtained from one or more sensors (e.g., microphone, camera, accelerometer, compass, etc.). For example, content obtained from one or more sensors may be processed by particular hardware circuitry to generate behavioral profile content representative of a particular individual's physical, mental, and/or emotional state. In an embodiment, behavioral profile content may include a plurality of parameters representative of focal point, excitement, anger, fear, fatigue, dehydration, or focus/distraction, or any combination thereof, in relation to a particular individual. Behavioral profile content may further include, by way of additional non-limiting examples, parameters representative of pre-breakthrough, silent like, regret/error acknowledgment, hunger, sloppiness/precision, empathy, and/or social engagement level, or any combination thereof. Further, in an embodiment, as depicted at block 240, epigenetic and/or other omic content and/or behavioral profile content may be analyzed and/or otherwise processed, such as via a behavioral processing unit, to identify relationships and/or correlations between particular behaviors and changes in epigenetic state for one or more individuals. Further, embodiments may also include omic content and/or behavioral profile content related to particular plants, such as may be advantageously utilized in agricultural settings, for example. In an embodiment, machine learning and/or other analysis techniques may be utilized to identify relationships and/or correlations between particular behaviors and/or changes in epigenetic and/or other omic state for a particular individual, although subject matter is not limited in scope in these respects.

As depicted at block 250, a further change in epigenetic state for a particular individual may be detected and/or predicted. In an embodiment, a further change in epigenetic state may be detected and/or predicted based, at least in part, on identified relationships and/or correlations between particular behaviors and particular changes in epigenetic state and/or also based at least in part on continued tracked behavioral profile content. In an embodiment, notification may be made to an individual, health professional, farmer, etc., at least in part in response to a further detected and/or predicted change in epigenetic state for a particular individual, as indicated at blocks 260 and/or 270, for example.

FIG. 3a is a schematic block diagram depicting an embodiment 300 of an example device, system, and/or process for communication of epigenetic content among various electronic devices. For example, embodiment 300 may include a secure storage device, such as secure storage device 400, that may maintain and/or access a database, such as database 490, that may store a bio-ledger and/or a biosphere ledger associated with one or more individuals, such as user 310. Embodiment 300 may also include a bio-smart device, such as bio-smart device 900, and/or an intermediary device, such as intermediary device 700. In general, and as discussed more fully below, an intermediary device, such as intermediary device 700, may be utilized to enable relatively secure communication of bio-ledger and/or biosphere ledger content between a secure storage device, such as secure storage device 400, and another device, such as bio-smart device 900.

Figure 3B:
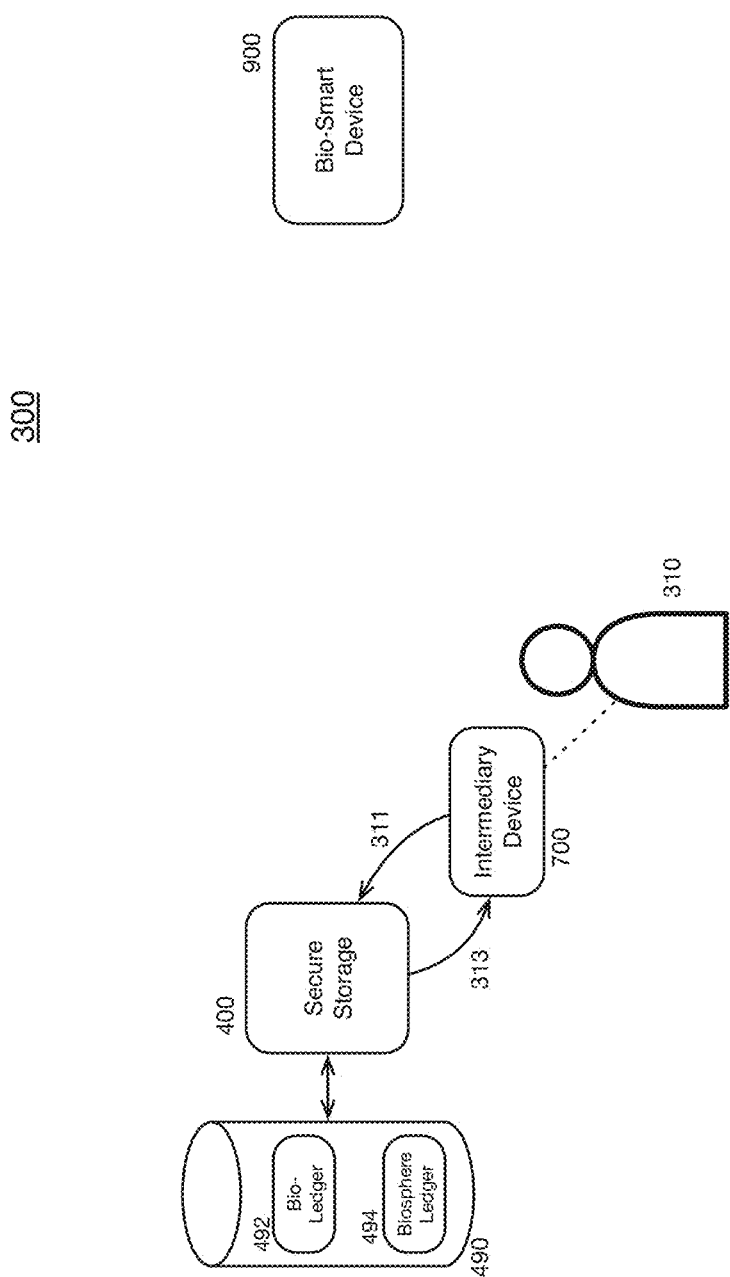
FIG. 3b is a schematic block diagram depicting an example communication of parameters between a storage device and an intermediary device, in accordance with an embodiment.

In an embodiment, an intermediary device, such as intermediary device 700, may be worn and/or carried, for example, by an individual, such as user 310. As depicted in FIG. 3b, an individual, such as user 310, may connect an intermediary device, such as intermediary device 700, to a secure storage device and/or system, such as secure storage device 400. In an embodiment, an intermediary device, such as intermediary device 700, may initiate communication of one or more parameters, such as parameter 311, particularly identifying a particular intermediary device, such as intermediary device 700, and/or a particular individual, such as user 310. In an embodiment, various parameters, such as security tokens, communications parameters, and/or cryptographic keys, for example, may be assigned to a particular individual, such as user 310, and/or to a particular intermediary device, such as intermediary device 700. In an embodiment, security, communication, and/or cryptographic parameters, for example, may be utilized by electronic devices, such as bio-smart device 900 and/or intermediary device 700, to access bio-ledger and/or biosphere ledger entries pertaining to a particular individual, such as user 310.

In an embodiment, at least in part in response to an intermediary device, such as intermediary device 700, being connected to a secure storage device, such as secure storage device 400, one or more security, communication, and/or cryptographic parameters, such as parameters 313, may be transferred from a secure storage device, such as secure storage device 400, to an intermediary device, such as intermediary device 700. Communications, between an intermediary device, such as intermediary device 700, and a secure storage device, such as secure storage device 400, may be accomplished via a wired connection, in an embodiment. While some embodiments may provide for wireless connection, security advantages may be realized through the use of a wired connection, in an embodiment. For example, user 310 may physically connect intermediary device 700 to secure storage device 400 via an external device interconnect, such as a USB port (see, for example, Universal Serial Bus Revision 3.2 Specification, published Sep. 22, 2017). In an embodiment, at least in part in response to a connection, such as via a USB port, of an intermediary device, such as intermediary device 700, at least one processor of a secure storage device, such as secure storage device 400, may initiate communication of one or more security, communication, and/or cryptographic parameters, such as parameters 313, between a secure storage device, such as secure storage device 400, and an intermediary device, such as intermediary device 700. In an embodiment, one or more parameters, such as parameters 313, may include one or more tokenized security parameters, as explained more fully below. In an embodiment, a tokenized security parameter, for example, may be utilized by an electronic device, such as a bio-smart device, to request access to particular content from a particular individual's bio-ledger and/or biosphere ledger, as also explained more fully below.

As depicted at FIG. 3c, an individual, such as user 310, at his or her discretion, for example, may physically bring an intermediary device, such as intermediary device 700, into proximity with an electronic device, such as bio-smart device 900, and/or may physically connect an intermediary device, such as intermediary device 700, to an electronic device, such as bio-smart device 900. At least in part in response to a wired and/or wireless connection of intermediary device 700 to bio-smart device 900, for example, one or more security, communication, and/or cryptographic parameters, such as parameters 313, may be communicated between intermediary device 700 and bio-smart device 900. In an embodiment, an intermediary device, such as intermediary device 700, may determine whether a bio-smart device, such as bio-smart device 900, has been pre-certified before initiating transmission of parameters between the intermediary device and the bio-smart device. For example, a secure storage device, such as secure storage device 400, may store and/or otherwise maintain a listing of bio-smart devices authorized to obtain security, communication, and/or cryptographic parameters. An intermediary device may, in an embodiment, check with a secure storage device, such as secure storage device 400, to determine whether a bio-smart device, such as bio-smart device 900, is authorized to receive security, communication, and/or cryptographic parameters. For example, an intermediary device 700 may communicate via a network, such as the Internet, with secure storage device 400, to determine whether bio-smart device 900 is pre-certified, for example. In an embodiment, "pre-certified" refers to a computing device, such as secure storage device 400, storing a certificate and/or other parameter indicative of a particular computing device's status with respect to permissions, licenses, and/or authorizations to read from and/or to write to and/or record to a particular individual's bio-ledger and/or biosphere ledger. Further, in an embodiment, an individual, such as user 310, may provide approval for communication of parameters between intermediary device 700 and bio-smart device 900, for example, such as via one or more inputs provided via a user interface of intermediary device 700 and/or of bio-smart device 900, for example. In other embodiments, user approval may be inferred from a physical connection of an intermediary device, such as intermediary device 700, and a bio-smart device, such as bio-smart device 900. At least in part via communication of particular parameters, such as parameters 313, for example, an individual, such as user 310, may grant access (e.g., read and/or write access) to particular content, such as one or more entries of bio-ledger 492 and/or biosphere ledger 494, to a particular electronic device, such as bio-smart device 900. Without parameters, such as parameters 313, obtained from an intermediary device, such as intermediary device 700, an electronic device, such as bio-smart device 900, may not be allowed access to particular content, such as bio-ledger 492 and/or biosphere ledger 494, for example.

Figure 3D:
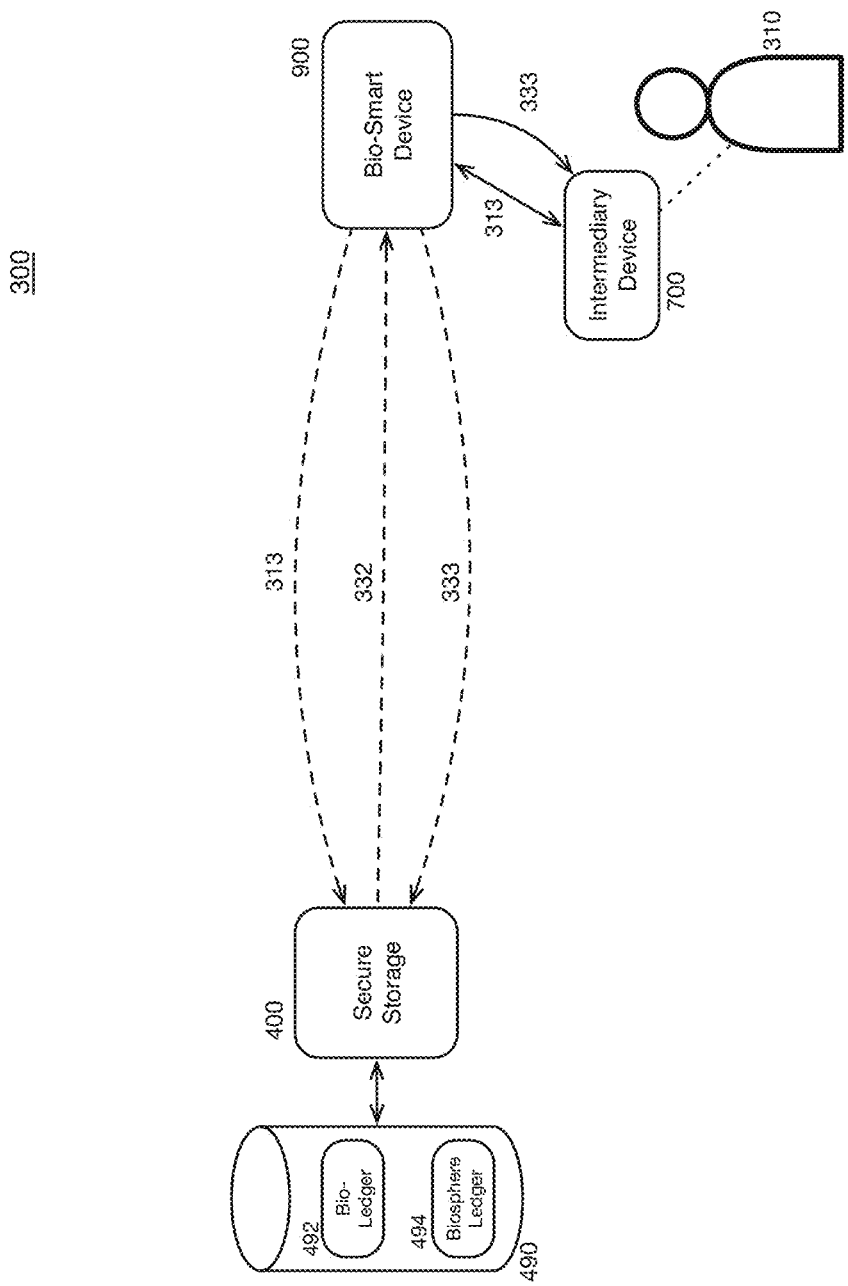
FIG. 3d is a schematic block diagram depicting an example device, system, and/or process for communication of epigenetic content, in accordance with an embodiment.

FIG. 3d depicts an example communication between a bio-smart device, such as bio-smart device 900, and a storage device, such as secure storage device 400, in accordance with an embodiment. In an embodiment, one or more communication parameters, such as one or more parameters 313, may indicate a particular address on a particular network, such as the Internet, at which a secure storage device, such as secure storage device 400, may be located. Utilizing, at least in part, one or more such communications parameters, such as parameters 313, an electronic device, such as bio-smart device 900, may establish communication with a secure storage device, such as secure storage device 400. In an embodiment, communication between bio-smart device and secure storage device 400 may include signal packet communications and/or signal frame communications, also referred to as signal packet transmissions and/or signal frame transmissions over a network, such as the Internet. Such communications may include wired and/or wireless communication of content (e.g., signals and/or states) between nodes of a network, where a node may comprise one or more network devices and/or one or more computing devices, for example Further, for example, parameters, such as parameters 313, may include one or more security parameters, such as one or more tokenized security parameters, that may indicate, directly and/or indirectly, an identity of a particular individual, such as user 310, and/or that may indicate, directly and/or indirectly, an identity of a particular intermediary device, such as intermediary device 700. In an embodiment, a secure storage device, such as secure storage device 400, may determine whether a bio-smart device, such as bio-smart device 900, is authorized (e.g., via a pre-certification process) to access bio-ledger and/or biosphere ledger content. For example, a secure storage device, such as secure storage device 400, may receive one or more such security parameters, such as one or more parameters 313, from an electronic device, such as bio-smart device 900. Secure storage device 400, for example, may permit access to particular entries of bio-ledger 492 and/or biosphere ledger 494, as depicted at arrow 332, based at least in part on a determination as to whether bio-smart device 900 is authorized (e.g., via a pre-certification process) to access such content. In an embodiment, parameters, such as parameters 313, for example, may be communicated between a bio-smart device, such as bio-smart device 900, and a secure storage device, such as secure storage device 900, at least in part by way of one or more signal packets in a wired and/or wireless connection, such as via a wired Ethernet connection and/or a wireless local area network connection (WLAN), for example. Further, in an embodiment, one or more signals packets may be communicated via a network, such as the Internet. Additionally, in an embodiment, if a bio-smart device, such as bio-smart device 900, is determined by a secure storage device, such as secure storage device 400, to not be authorized (e.g., via a pre-certification process), an error message may be returned to the bio-smart device. In an embodiment, an error message may be communicated by way of one or more signal packets via a wired and/or wired connection, such as via a wired Ethernet connection and/or a WLAN, for example. As mentioned, for example, cryptographic parameters, such as one or more parameters 313, may include one or more encryption and/or decryption keys. In an embodiment, an electronic device, such as bio-smart device 900, may decrypt content, such as bio-ledger and/or biosphere ledger entries, for example, that may be obtained from a secure storage device, such as secure storage device 400.

Additionally, in an embodiment, a bio-smart device, such as bio-smart device 900, may generate and/or otherwise obtain content pertaining to a particular individual, such as user 310. Further, generated and/or otherwise obtained content may be provided to a secure storage device, such as secure storage device 400. For example, a bio-smart device, such as bio-smart device 900, may generate biosphere and/or bio-ledger content, such as content 333, pertaining to a particular individual, such as user 310. A bio-smart device, such as bio-smart device 900, may initiate transmission of generated and/or otherwise obtained biosphere and/or bio-ledger content, such as content 333, for example, to a secure storage device, such as secure storage device 400. Further, a bio-smart device, such as bio-smart device 900, may initiate communication of generated and/or otherwise obtained biosphere and/or bio-ledger content, such as content 333, to an intermediary device, such as intermediary device 700.

In an embodiment, a secure storage device, such as secure storage device 400, may operate, at least in part, as a centralized storage for epigenetic and/or other omic content, such as bio-ledger content 492 and/or biosphere ledger content 494, for any number of particular individuals. Further, in an embodiment, a secure storage device and/or system, such as secure storage device 400, may be located at a doctor's office, diagnostics lab, genetic lab, and/or other medical and/or scientific institution, to name a few non-limiting examples. At least in part via selective dissemination of particular security, communication, and/or cryptographic parameters to particular electronic devices, content stored in a database, such as database 490, may be relatively securely maintained. In an embodiment, a particular individual, such as user 310, may control communication of bio-ledger and/or biosphere ledger content pertaining to that particular individual at least in part by controlling dissemination of particular security, communication, and/or cryptographic parameters.

Although example embodiments may describe a secure storage device, such as secure storage device 400, storing bio-ledger and/or biosphere content and also providing communication, security, and/or cryptographic parameters to electronic devices, such as intermediary device 700, other embodiments may utilize separate devices, systems, and/or processes for storing bio-ledger and/or biosphere content and disseminating communication, security, and/or cryptographic parameters. For example, communication, security, and/or cryptographic parameters may be assigned, stored, and/or communicated at a device and/or system separate from secure storage device 400. Also, as mentioned herein, a secure storage device, such as secure storage device 400, may include one or more computing devices, and/or may include a number of distributed computing devices. For example, embodiments may employ distributed computing and/or communication approaches in which portions of a process, such as signal processing and/or storage of signal samples, for example, may be allocated among various devices, including one or more client devices and/or one or more server devices, via a computing and/or communications network, for example.

Further, in an embodiment, communication between a secure storage device, such as secure storage device 400, and an electronic device, such as bio-smart device 900, for example, may occur via a wired connection or via a wireless connection, or a combination thereof. Non-limiting examples of wired and/or wireless communication interfaces, networks, specifications, protocols, etc., are provided below.

Figure 4:
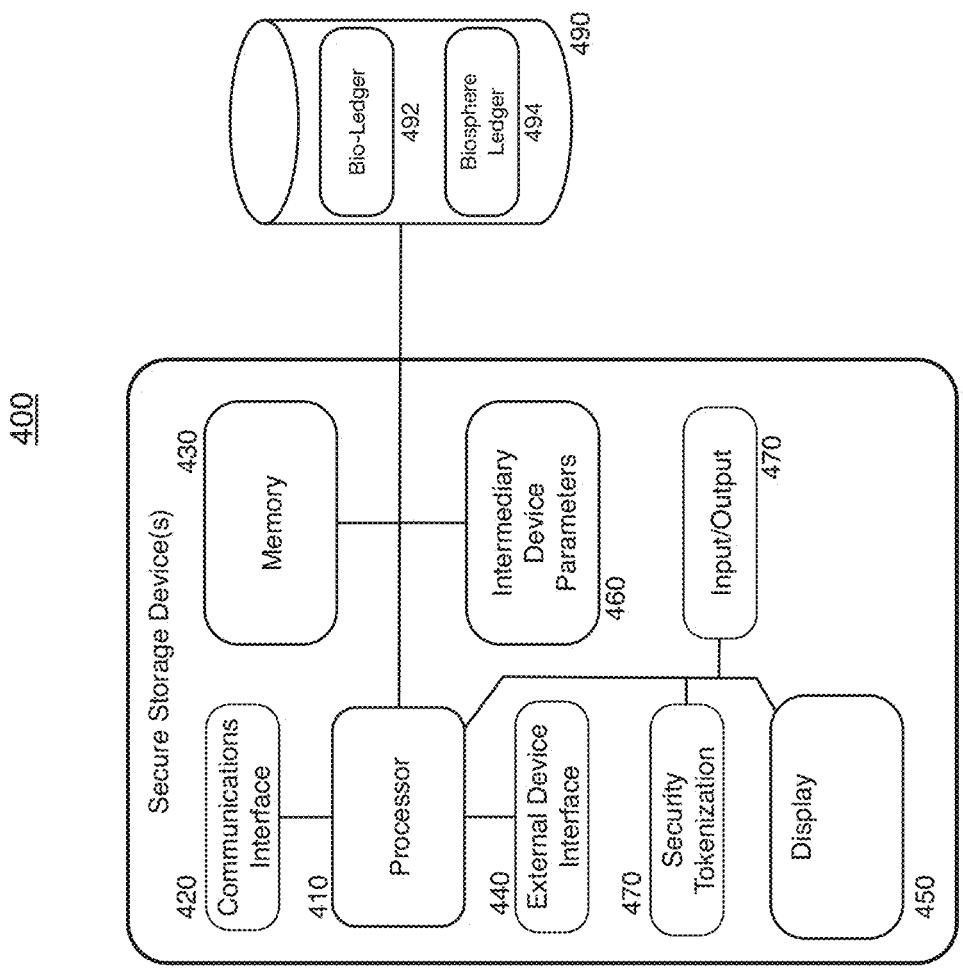
FIG. 4 is an illustration of an example storage device, in accordance with an embodiment.

FIG. 4 is an illustration of an example storage device, in accordance with an embodiment. In an embodiment, a secure storage device, such as secure storage device 400, may access, store, and/or maintain epigenetic and/or environmental content within a database, such as database 490. In an embodiment, a database, such as database 490, may include one or more mass storage devices and/or memory devices. Example storage device and/or memory device types are mentioned below. In an embodiment, a database, such as database 490, may include bio-ledger 492 and/or biosphere ledger 494. As utilized herein, "secure storage" and/or "secure storage device" refer to at least one apparatus, such as at least one computing device, including at least one non-transitory medium and/or memory, to store content, such as bio-ledger and/or biosphere ledger content, and/or to implement one or more security protocols and/or techniques to at least partially safeguard content, such as bio-ledger content and/or biosphere ledger content, from unauthorized access. For example, a secure storage device, such as secure storage device 400, may allow access to one or more entries of a bio-ledger, such as bio-ledger 492, and/or to one or more entries of a biosphere ledger, such as biosphere ledger 494, at least in part in response to a communication of appropriate security tokens between a device, such as a bio-smart device 900, and a secure storage device, such as secure storage device 400.

In an embodiment, a secure storage device, such as secure storage device 400, may include at least one processor, such as processor 410. In an embodiment, at least one processor, such as processor 410, may initiate transmission of one or more communication, security, and/or cryptographic parameters to an electronic device, such as intermediary device 700. For example, processor 410 may initiate communication of one or more communication, security, and/or cryptographic parameters to an electronic device, such as intermediary device 700, at least in part in response to an electronic device, such as intermediary device 700, becoming connected to secure storage device 400. In an embodiment, a secure storage device, such as secure storage device 400, may comprise one or more communications interfaces, such as communications interface 420. One or more communications interfaces, such as communications interface 420, may enable wireless communications between a secure storage device, such as secure storage device 400, and one or more other computing devices, such as intermediary device 700 and/or bio-smart device 900, for example. In an embodiment, wireless communications may occur substantially in accordance any of a wide range of communication protocols, such as those mentioned herein, for example.

Also, in an embodiment, a secure storage device, such as secure storage device 400, may include an external device interface, such as external device interface 440. In an embodiment, an external device interface, such as external device interface 440, may be substantially compatible and/or substantially compliant with a USB specification, although subject matter is not limited in scope in these respects. In an embodiment, an electronic device, such as intermediary device 700, may connect to and/or communicate with a secure storage device, such as secure storage device 400, via a wired connection (e.g., via external device interface 440), and/or via a wireless connection (e.g., via communications interface 420).

In an embodiment, a secure storage device, such as secure storage device 400, may further include a memory, such as memory 430. In an embodiment, memory 430 may comprise a non-volatile memory, for example. Further, in an embodiment, a memory, such as memory 430, may have stored therein executable instructions, such as for one or more operating systems, communications protocols, and/or applications, for example. A memory, such as 430, may further store intermediary device parameters, such as parameters 460. In an embodiment, parameters 460 may include one or more particular communications, security, and/or cryptographic parameters that may be assigned to a particular individual, such as user 310, and/or to a particular electronic device, such as intermediary device 310. A secure storage device, such as secure storage device 400, may further include a security tokenization unit, such as unit 470. In an embodiment, a security tokenization unit, such as unit 470, may generate one or more security tokens to at least temporarily associate a particular individual and/or particular entries of stored content, such as one or more entries of bio-ledger 492 and/or biosphere ledger 494, with a particular parameter, such as one or more parameters 460 and/or 313, for example.

In an embodiment, processor 410 may initiate communication of parameters 460 to another electronic device, such as intermediary device 700, at least in part in response to a connection of another electronic device, such as intermediary device 700, to secure storage device 400 either via external device interface 440 and/or via communications interface 420, for example. Further, in an embodiment, a secure storage device, such as secure storage device 400, may comprise a display, such as display 450, and/or may include input/output circuitry, such as circuitry 470, for example. In an embodiment, input/output circuitry may include circuitry to accommodate a keyboard, mouse, stylus, audio speaker, microphone, printer, etc., to name but a few non-limiting examples of input and/or output devices.

Figure 5:
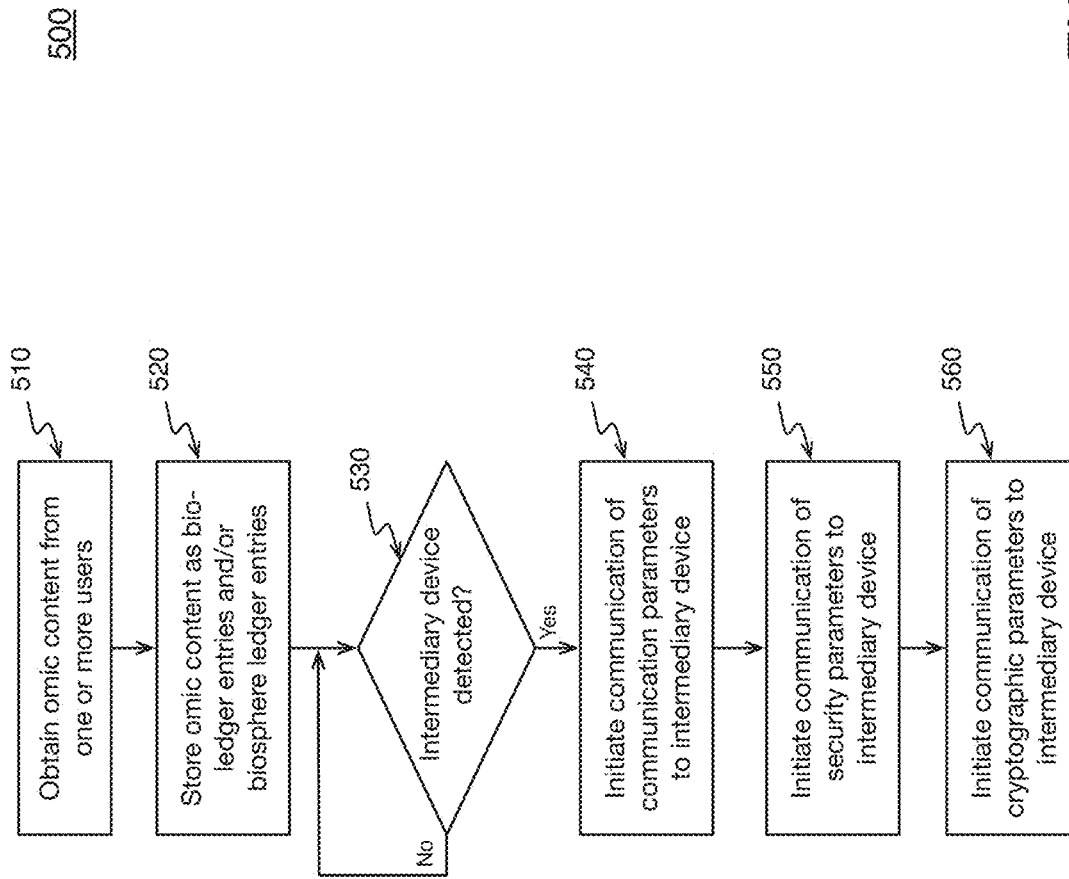
FIG. 5 is an illustration of an example process for initiating communication of parameters to an intermediary device, in accordance with an embodiment.

FIG. 5 is an illustration of an embodiment 500 of an example process for initiating communication of one or more parameters, such as communication, security, and/or cryptographic parameters, from a secure storage device, such as secure storage device 400, to an intermediary device, such as intermediary device 700. Embodiments in accordance with claimed subject matter may include all of blocks 510-560, fewer than blocks 510-560, and/or more than blocks 510-560. Further, the order of blocks 510-560 is merely an example order, and subject matter is not limited in scope in these respects. In an embodiment, an example process for initiating communication of one or more parameters, such as communication, security, and/or cryptographic parameters, to an intermediary device may be implemented, at least in part, via utilization of a secure storage device, such as secure storage device 400, although the scope of subject matter is not limited in scope in this respect.

As depicted at block 510, omic and/or other epigenetic content pertaining to one or more individuals may be obtained. In an embodiment, omic and/or epigenetic content may be obtained by a secure storage device, such as secure storage device 400, at least in part by receiving, at communications interface 420, signal packets and/or signal frames, for example, transmitted over a network, such as the Internet. In an embodiment, epigenetic and/or other omic content may be obtained at least in part by receiving signal packets and/or signal frames from test lab computing devices, doctor office computing devices, etc. In an embodiment, omic and/or other epigenetic content may be stored as one or more bio-ledger entries and/or one or more biosphere entries, as depicted at block 520, for example. In an embodiment, bio-ledger entries and/or biosphere entries may be stored, for example, as signals and/or states in one or more non-transitory media and/or memories and/or mass storage devices of a secure storage device, such as secure storage device 400. As mentioned, bio-ledger entries may include parameters representative of one or more aspects of genetic content, epigenetic content, microbiome content, proteome content, metabolome content, or transcriptome content, or any combination thereof, associated with and/or pertaining to one or more particular individuals, for example. Bio-ledger entries may further include lab test content for one or more particular individuals, content representative of diagnosed diseases for one or more particular individuals, identified risk factors for one or more particular individuals, etc., although subject matter is not limited in scope in this respect. Further, as mentioned, biosphere ledger entries may include parameters representative of one or more environmental aspects related to one or more particular individuals, for example.

In an embodiment, an intermediary device may be detected, as indicated at block 530. For example, a secure storage device, such as secure storage device 400, may detect a physical and/or electrical connection of an intermediary device, such as intermediary device 700, to an external device interface, such as external device interface 440. For another example, a secure storage device, such as secure storage device 400, may detect a wireless connection of an intermediary device, such as intermediary device 700, via a communications interface, such as communications interface 420. In some embodiments, security advantages may be experienced through an implementation of a wired connection between secure storage device 400 and intermediary device 700. For example, intermediary device 700 may connect to secure storage device 400 by way of a USB interface and/or another type of wired interface. Further, in an embodiment, at least in part in response to detection of an intermediary device, such as intermediary device 700, a device, such as secure storage device 400, may transmit one or more communication parameters to an intermediary device, such as intermediary device 700, as indicated at block 540. Additionally, at least in part in response to detection of an intermediary device, such as intermediary device 700, a device, such as secure storage device 400, may transmit one or more security parameters to an intermediary device, such as intermediary device 700, as indicated at block 550. Further, in an embodiment, at least in part in response to detection of an intermediary device, such as intermediary device 700, a device, such as secure storage device 400, may transmit one or more cryptographic parameters (e.g., encryption and/or decryption keys) to an intermediary device, such as intermediary device 700, as indicated at block 560. In an embodiment, parameters, such as one or more security parameters, communication parameters, and/or cryptographic parameters, may be transmitted from a secure storage device, such as secure storage device 400, to an intermediary device, such as intermediary device 700, as one or more signals and/or signals packets via a wired interconnect, such as via a USB interconnect, for example. For example, external device interface 440 may comprise a USB hub device, and communication between secure storage device 400 and intermediary device 700 may include USB signal packet transmissions performed under control on external device interface 440, for example. As mentioned above and as further discussed below, an intermediary device, such as intermediary device 700, may be utilized to relatively securely communicate parameters, such as one or more security parameters, communication parameters, and/or cryptographic parameters, between a secure storage device, such as secure storage device 400, and another device, such as bio-smart device 900. In an embodiment, parameters, such as one or more security parameters, communication parameters, and/or cryptographic parameters, may allow a device, such as bio-smart device 900, to request access to content, such as particular bio-ledger and/or biosphere ledger content pertaining to a particular individual, from a secure storage device, such as secure storage device 400.

Figure 6:
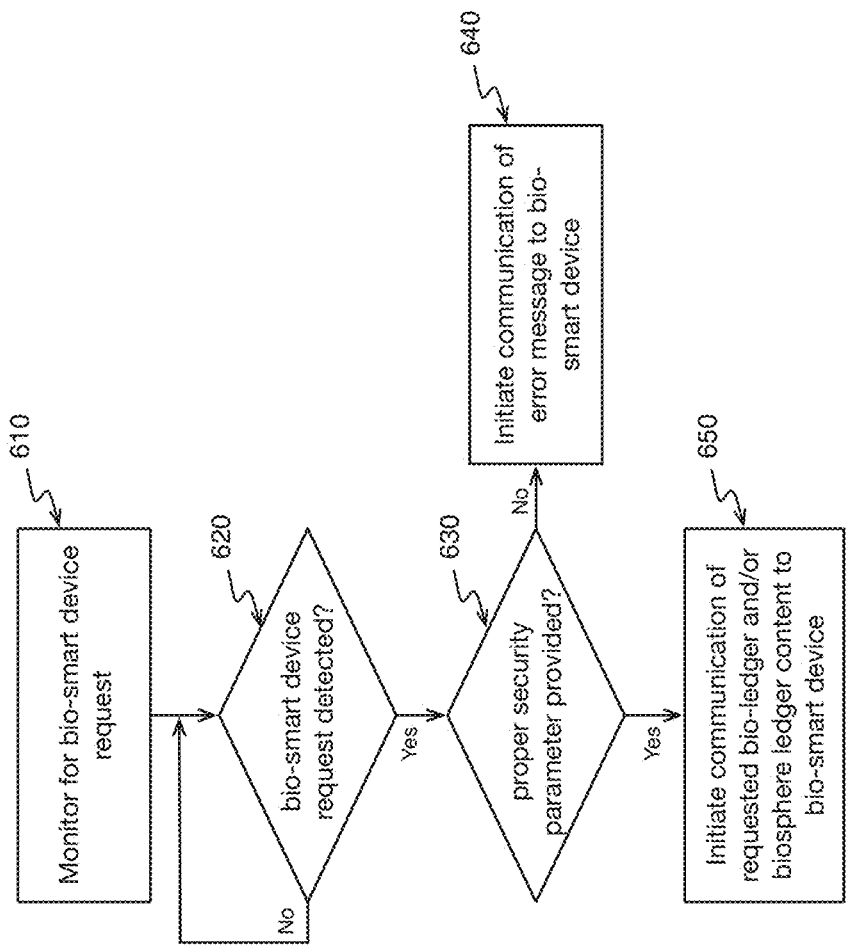
FIG. 6 is an illustration of an example process for initiating communication of epigenetic content parameters, in accordance with an embodiment.

FIG. 6 is an illustration of an embodiment 600 of an example process for initiating communication of epigenetic content parameters, in accordance with an embodiment. Embodiments in accordance with claimed subject matter may include all of blocks 610-650, fewer than blocks 610-650, and/or more than blocks 610-650. Further, the order of blocks 610-650 is merely an example order, and subject matter is not limited in scope in these respects. In an embodiment, an example process for initiating communication of omic and/or other epigenetic content parameters may be implemented, at least in part, via utilization of a secure storage device, such as secure storage device 400, although the scope of subject matter is not limited in scope in this respect.

In an embodiment, an electronic device, such as secure storage device 400, may monitor for requests from one or more bio-smart devices, such as bio-smart device 900, as indicated at block 610. In an embodiment, a request from a bio-smart device, such as bio-smart device 900, may be received as one or more signals and/or states via a wireless and/or wired network interface, such as communications interface 420, for example. For example, bio-smart device 900 may transmit a request to communicate with secure storage device 400 via one or more signal packets over a wired and/or wireless connection. Example wired and/or wireless interconnect technologies are mentioned below, although claimed subject matter is not limited in scope in these respects. In an embodiment, bio-smart device 900 may transmit a request to communicate with secure storage device 400 via one or more signal packets over a wired Ethernet connection and/or via a WLAN connection, for example. In an embodiment, bio-smart device 900 may communicate with secure storage device 400 via a network, such as the Internet. Further, in an embodiment, a request from a bio-smart device, such as bio-smart device 900, may include one or more parameters, such as one or more security parameters. In an embodiment, a security parameter, such as may be provided to a bio-smart device by an intermediary device, such as intermediary device 700, may indicate, for example, a particular individual and/or may identify a particular intermediary device. As mentioned, an intermediary device, such as intermediary device 700, may be utilized to relatively securely communicate parameters, such as one or more security parameters, communication parameters, and/or cryptographic parameters, between a secure storage device, such as secure storage device 400, and another device, such as bio-smart device 900. In an embodiment, parameters, such as one or more security parameters, communication parameters, and/or cryptographic parameters, may allow a device, such as bio-smart device 900, to request access to content, such as particular bio-ledger and/or biosphere ledger content pertaining to a particular individual, from a secure storage device, such as secure storage device 400.

As indicated at blocks 620 and/or 630, at least in part in response to a detection of a request from a bio-smart device, such as bio-smart device 900, a processor, such as processor 410, may determine whether an appropriate security parameter has been provided by the bio-smart device. In an embodiment, for example, a comparison may be made utilizing a processor, such as processor 410, to determine whether a security parameter provided by a bio-smart device, such as bio-smart device 900, matches a security parameter previously expected for a particular individual, such as user 310, and/or to a particular user device, such as intermediary device 700, for example. Alternatively, in an embodiment, a secure storage device, such as secure storage device 400, may determine whether bio-smart device 900 has been pre-certified to access the requested content. As depicted at block 640, at least in part in response to a determination that no appropriate security parameter was provided by a bio-smart device, such as bio-smart device 900 (e.g., bio-smart device 900 is determined to not be pre-certified), at least one processor, such as processor 410, of a secure storage device, such as secure storage device 400, may initiate communication of an error message to a bio-smart device, such as bio-smart device 900. In an embodiment, an error message may be generated by a communications interface, such as communications interface 420, as one or more signals and/or signal packets for example.

Further, as depicted at block 650, at least in part in response to a determination that an appropriate security parameter has been provided by a bio-smart device, such as bio-smart device 900 (e.g., by comparing a security token with a certificate and/or other parameter maintained by secure storage device 400), at least one processor, such as processor 410, of a secure storage device, such as secure storage device 400, may initiate communication of requested bio-ledger and/or biosphere ledger content, such as one or more requested entries from bio-ledger 492 and/or biosphere ledger 494, to a bio-smart device, such as bio-smart device 900. In an embodiment, bio-ledger content and/or biosphere ledger content may be transmitted by a communication interface, such as communication interface 420, at least in part by generating one or more signals and/or signal packets for transfer via a wired and/or wireless connection, examples of which are found below. In this manner, a bio-smart device, such as bio-smart device 900, may obtain particular bio-ledger and/or biosphere ledger content pertaining to a particular individual from a secure storage device, such as secure storage device 400. Similarly, in an embodiment, a bio-smart device, such as bio-smart device 900, may be permitted, if determined by secure storage device 400 to be authorized, to write and/or record entries to a particular individual's bio-ledger and/or biosphere ledger entries stored at secure storage device 400. Further, in this manner, a secure storage device, such as secure storage device 400, may deny read and/or write opportunities to particular bio-ledger and/or biosphere content to particular devices, such as particular bio-smart devices, that provide inappropriate and/or insufficient security parameters. As mentioned, a bio-smart device, such as bio-smart device 900, may obtain such security parameters from via an intermediary device, such as intermediary device 700. Utilization of an intermediary device, such as intermediary device 700, to communicate security parameters allows for an individual, such as user 310, to determine which bio-smart devices, for example, have access to confidential and/or personal bio-ledger and/or biosphere ledger content.

Figure 7:
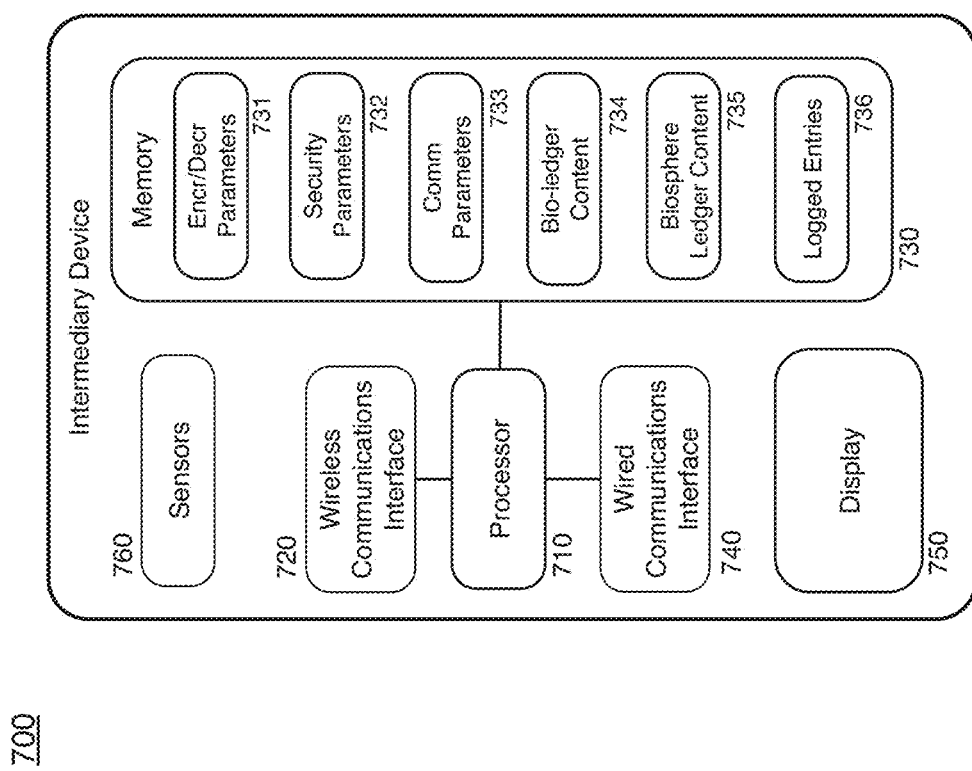
FIG. 7 is an illustration of an example intermediary device, in accordance with an embodiment.

FIG. 7 is an illustration of an embodiment 700 of an example intermediary device. As utilized herein, "intermediary device" and/or the like refers to an electronic device to facilitate, at least in part, communication of particular parameters between a storage device, such as secure storage device 400, and another electronic device, such as bio-smart device 900, at least in part via storage of particular signals and/or states associated with a particular individual. In embodiments, an intermediary device, such as intermediary device 700, may be implemented as any of a variety of device types. In embodiments, intermediary device types may include wearable and/or portable electronic devices. For example, and not by way of limitation, an intermediary device types may include cellular phones, tablet devices, notebook computing devices, electronic watches, personal display devices, personal digital assistants, key fobs, portable storage devices (e.g., USB non-volatile storage stick), personal fitness devices, etc. In other embodiments, an intermediary device, such as intermediary device 700, may be incorporated into one or more vehicles (e.g., car, bicycle, motorcycle, etc.). Further, in embodiments, intermediary devices, such as intermediary device 700, may be incorporated into articles of clothing, purses, wallets, shoes, other accessories, etc. Of course, subject matter is not limited in scope in these respects.

In an embodiment, an intermediary device, such as intermediary device 700, may comprise one or more processors, such as processor 710, and/or may comprise one or more communications interfaces, such as communications interfaces 720 and/or 740. In an embodiment, one or more communications interfaces, such as communications interface 720, may enable, at least in part, wireless communications between an intermediary device, such as intermediary device 700, and one or more other electronic devices, such as secure storage device 400 and/or bio-smart device 900, for example. Further, in an embodiment, one or more communications interfaces, such as communications interface 740, may enable wired communications, at least in part, between an intermediary device, such as intermediary device 700, and one or more other electronic devices, such as secure storage device 400 and/or bio-smart device 900, for example. In an embodiment, wired and/or wireless communications may occur substantially in accordance any of a wide range of communication protocols, such as those mentioned herein, for example. For example, intermediary device 700 may communicate with secure storage device 400 by way of a wired USB connection. In an embodiment, external device interface 440 of secure storage device 400 may transmit one or more signal packets to intermediary device 700 by way of a USB interconnect, for example. Similarly, communication between intermediary device 700 and bio-smart device 900 may include wired communication, such as via a USB interconnect, and/or wireless communication, such as via WLAN and/or Bluetooth, for example.

In an embodiment, an intermediary device, such as intermediary device 700, may include a memory, such as memory 730. In an embodiment, memory 730 may comprise a non-volatile memory, for example. Further, in an embodiment, a memory, such as memory 730, may have stored therein executable instructions, such as for one or more operating systems, communications protocols, applications, etc., for example. Further, in an embodiment, an intermediary device, such as intermediary device 700, may comprise a display, such as display 750, one or more sensors, such as one or more sensors 760. In an embodiment, sensors may include, to name a few non-limiting examples, one or more radio frequency sensors/transceivers, cameras, microphones, accelerometers, altimeters, gyroscopes, compasses, thermometers, magnetometers, barometers, light sensors, or proximity sensors, or any combination thereof. Of course, these are merely example types of components that may be included in a mobile device, and subject matter is not limited in scope to these particular examples.

In an embodiment, a memory, such as memory 730, of an intermediary device, such as intermediary device 700, may store varied types of digital content. For example, an intermediary device, such as intermediary device 700, may store one or more parameters obtained, for example, from a secure storage device, such as secure storage device 400. In an embodiment, an intermediary device, such as intermediary device 700, may store communications parameters, such as communications parameters 733, security parameters, such as security parameters 732, and/or cryptographic parameters, such as encryption and/or decryption parameters 731.

As mentioned, an intermediary device, such as intermediary device 700, may obtain parameters, such as one or more security, communications, and/or cryptographic parameters, from a secure storage device, such as secure storage device 400. For example, an intermediary device, such as intermediary device 700, may obtain encryption and/or decryption parameters 731, security parameters 732, and/or communications parameters 733, or any combination thereof, from a computing device, such as secure storage device 400. Further, in an embodiment, an intermediary device, such as intermediary device 700, may be utilized by an individual, such as user 310, to enable a bio-smart device, such as bio-smart device 900, to obtain parameters, such as encryption and/or decryption parameters 731, security parameters 732, and/or communications parameters 733, or any combination thereof, from an intermediary device, such as intermediary device 700.

For example, an individual may physically bring an intermediary device, such as intermediary device 700, into proximity with an electronic device, such as bio-smart device 900, and/or may physically connect an intermediary device, such as intermediary device 700, to an electronic device, such as bio-smart device 900. At least in part in response to a wired and/or wireless connection of intermediary device 700 to bio-smart device 900, for example, one or more security parameters 732, communication parameters 733, and/or encryption and/or decryption parameters 731, may be communicated between intermediary device 700 and bio-smart device 900. Further, as mentioned, a bio-smart device, such as bio-smart device 900, may utilize one or more communication, security, and/or cryptographic parameters obtained from an intermediary device, such as intermediary device 700, to obtain epigenetic content, such as one or more bio-ledger and/or biosphere ledger entries, for a particular individual, such as user 310, from a secure storage device, such as secure storage device 400.

In some embodiments, bio-smart devices may not be networked, and therefore may not have a capability of communicating with a storage device, such as secure storage device 400, to obtain and/or to contribute bio-ledger and/or biosphere ledger content for a particular individual. In some embodiments, an intermediary device, such as intermediary device 700, may further store actionable biological content (e.g., epigenetic and/or other omic content that may spur action in an individual and/or bio-smart device) related to a particular individual, such as user 310. For example, an intermediary device, such as intermediary device 700, may store particular genetic, epigenetic content, content related to health goals, content representative of doctor directive, etc., to name a few example content types. In an embodiment, an intermediary device, such as intermediary device 700, may store bio-ledger content, such as bio-ledger content 734, and/or may store biosphere ledger content, such as biosphere ledger content 735, for example.

In an embodiment, an intermediary device, such as intermediary device 700, may obtain actionable biological content, such as particular bio-ledger entries, particular biosphere ledger entries, and/or other content types from a secure storage device, such as secure storage device 400. Further, in an embodiment, a non-networked bio-smart device, for example, may obtain actionable biological content, particular bio-ledger entries, particular biosphere ledger entries, and/or other content types, for example, from an intermediary device, such as intermediary device 700. In this manner, an intermediary device, such as intermediary device 700, may support and/or enable non-networked bio-smart devices, in an embodiment.

Additionally, in an embodiment, an intermediary device, such as intermediary device 700, may store parameters, such as logged entries 736, obtained from one or more electronic devices, such as one or more bio-smart devices 900. In an embodiment, a bio-smart device, such as bio-smart device 900, may initiate communication of content, such as particular bio-ledger and/or biosphere ledger entries, to an intermediary device, such as intermediary device 700. At a subsequent point in time, an intermediary device, such as intermediary device 700, may upload stored content, such as logged entries 736, to a secure storage device, such as secure storage device 400, for example. In an embodiment, content, such as logged entries 736, gathered at least in part via an intermediary device, such as intermediary device 700, may be uploaded to a bio-ledger, such as bio-ledger 492, and/or a biosphere ledger, such as biosphere ledger 494, of a database, such as database 490. In an embodiment, content, such as logged entries 736, gathered at least in part via use of an intermediary device, such as intermediary device 700, may be analyzed and/or otherwise processed at least in part by one or more electronic devices, such as secure storage device 400, and/or may be analyzed, for example, by one or more medical professionals.

Further, content, such as one or more of logged entries 736, may include sensitive, personal, and/or confidential content that may be advantageously communicated to an individual, such as user 310, by a medical professional. For example, by having a medical professional communicate sensitive, personal, and/or confidential content, such as one or more of logged entries 736, a situation may be avoided wherein a device, such as bio-smart device 900, could be seen as offering medical advice. Of course, these are merely examples of how content, such as logged entries 736, may be analyzed and/or otherwise processed. As mentioned, at least in part because an individual, such as user 310, may maintain possession and/or control of an intermediary device, such as intermediary device 700, an individual, such as user 310, may, at least in part, control access to particular content, such as one or more entries of bio-ledger 492, biosphere ledger 494, and/or logged entries 736, for example.

Figure 8:
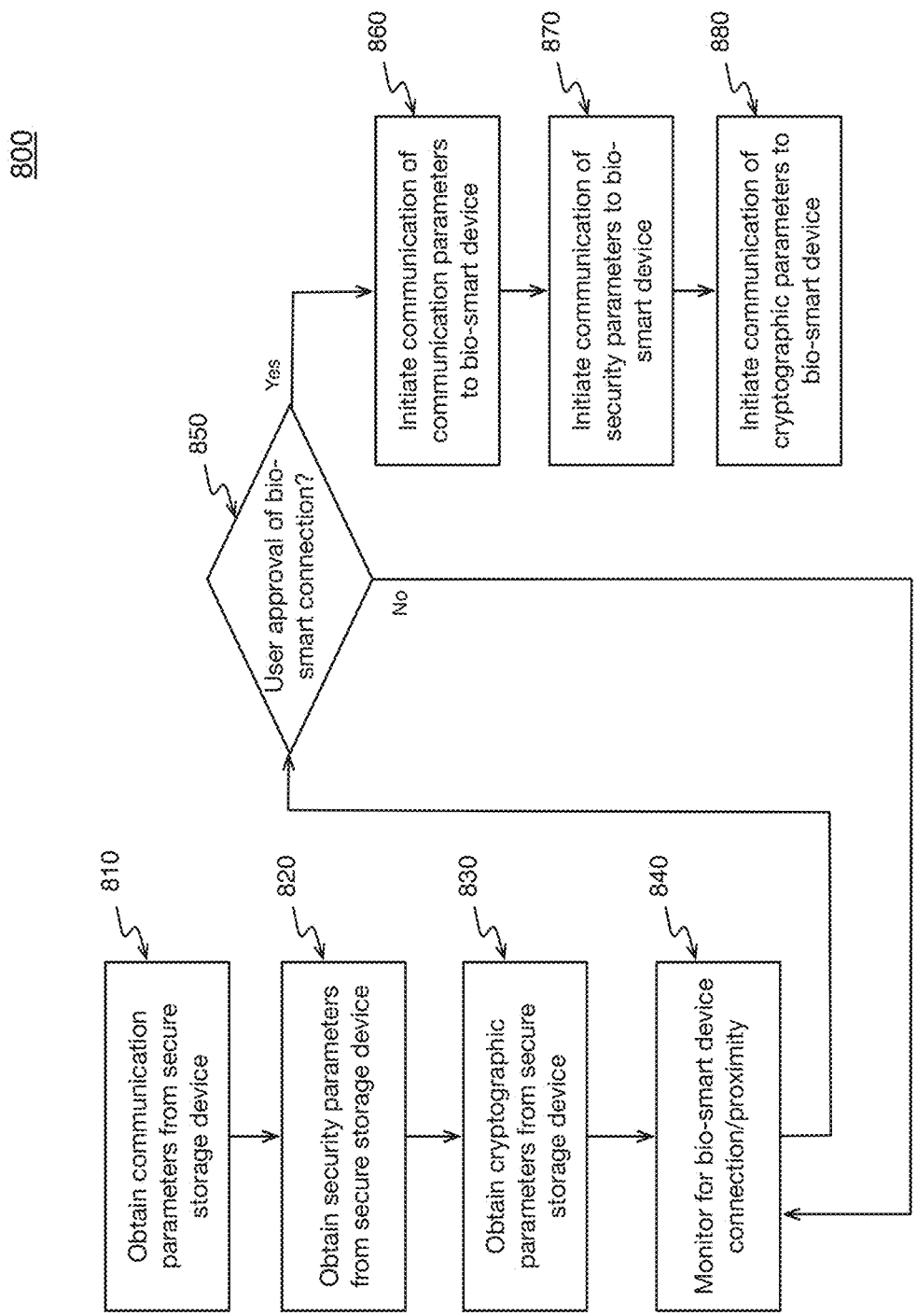
FIG. 8 is an illustration of an example process for initiating communication of parameters to a bio-smart device, in accordance with an embodiment.

FIG. 8 is an illustration of an embodiment 800 of an example process for initiating communication of parameters to a bio-smart device, such as bio-smart device 900. Embodiments in accordance with claimed subject matter may include all of blocks 810-880, fewer than blocks 810-880, and/or more than blocks 810-880. Further, the order of blocks 810-880 is merely an example order, and subject matter is not limited in scope in these respects. In an embodiment, an example process for initiating communication of one or more parameters, such as communication, security, and/or cryptographic parameters, to an electronic device, such as a bio-smart device (e.g., bio-smart device 900), may be implemented, at least in part, via utilization of an intermediary device, such as intermediary device 700, although the scope of subject matter is not limited in scope in this respect.

As depicted at block 810, an apparatus, such as intermediary device 700, may obtain one or more communication parameters from a storage device, such as secure storage device 400. For example, as mentioned, intermediary device 700 may receive signal packets and/or signal frames via a USB interconnect from external device interface 440 of secure storage device 400. Additionally, as depicted at block 820, an apparatus, such as intermediary device 700, may obtain one or more security parameters from a storage device, such as secure storage device 400. Further, as depicted at block 830, an apparatus, such as intermediary device 700, may obtain one or more cryptographic parameters from a storage device, such as secure storage device 400. Examples of communication, security, and/or cryptographic parameters are mentioned above. Further, as mentioned, communication, security, and/or cryptographic parameters may be transferred from external device interface 440 of secure storage device 400 to a wired communications interface 740 of intermediary device 700 at least in part in response to intermediary device 700 becoming physically and/or electrically connected to secure storage device 400 via an external device interface, such as a USB connection.

In an embodiment, an apparatus, such as intermediary device 700, may monitor for proximity and/or connection to a bio-smart device, such as bio-smart device 900, as indicated at block 840. For example, an intermediary device, such as intermediary device 700, may detect a physical and/or electrical connection of an intermediary device, such as intermediary device 700, to an communication interface, such communication interface 920, of a bio-smart device, such as bio-smart device 900. For another example, an apparatus, such as intermediary device 700, may detect a wireless signal transmitted by a bio-smart device, such as bio-smart device 900. For example, a wireless communication interface 720 of intermediary device 700 may receive one or more wireless, radio-frequency signals from communication interface 920 of bio-smart device 900. In an embodiment, an apparatus, such as intermediary device 700, may connect via a wireless connection to a bio-smart device, such as bio-smart device 900.

Further, in an embodiment, at least in part in response to detection of a user approval of a wired and/or wireless connection between an apparatus, such as intermediary device 700, and a bio-smart device, such as bio-smart device 900, an apparatus, such as intermediary device 700, may initiate communication of one or more communication parameters to a bio-smart device, such as bio-smart device 900, as indicated at blocks 850 and/or 860. In an embodiment, a wireless communication interface 720 and/or wired communication interface 740 may transmit signal packets and/or signal frames, for example, to communication interface 920, for example. Additionally, an apparatus, such as intermediary device 700, may initiate communication of one or more security parameters to a bio-smart device, such as bio-smart device 900, as indicated at block 870. Wireless communication interface 720 and/or wired communication interface 740 may transmit signal packets and/or signal frames comprising one or more security parameters, for example, to communication interface 920. Further, as indicated at block 880, an apparatus, such as intermediary device 700, may initiate communication of one or more cryptographic parameters to a bio-smart device, such as bio-smart device 900. Wireless communication interface 720 and/or wired communication interface 740 may transmit signal packets and/or signal frames comprising one or more cryptographic parameters, for example, to communication interface 920, in an embodiment.

In an embodiment, "user approval" may be inferred from an individual, such as user 310, physically connecting an intermediary device, such as intermediary device 700, to a particular bio-smart device, such as bio-smart device 900. In other embodiments, user approval may include an individual explicitly indicating through a user interface located on an intermediary device, such as intermediary device 700, and/ or on a bio-smart device, such as bio-smart device 900. For example, an individual may interact with a fingerprint scanner and/or some other bio-authentication device to confirm identity and/or to explicitly approve communication between an intermediary device, such as intermediary device 700, and a bio-smart device, such as bio-smart device 900. Additionally, in embodiments, an individual, such as user 310, may provide prior approval to connections with one or more particular bio-smart devices. For example, one or more security parameters, such as security parameters 732, may identify, at least in part, one or more particular bio-smart devices, such as bio-smart device 900, with which an intermediary device, such as intermediary device 700, may interact without obtaining additional approvals from an individual, such as user 310.

Figure 9:
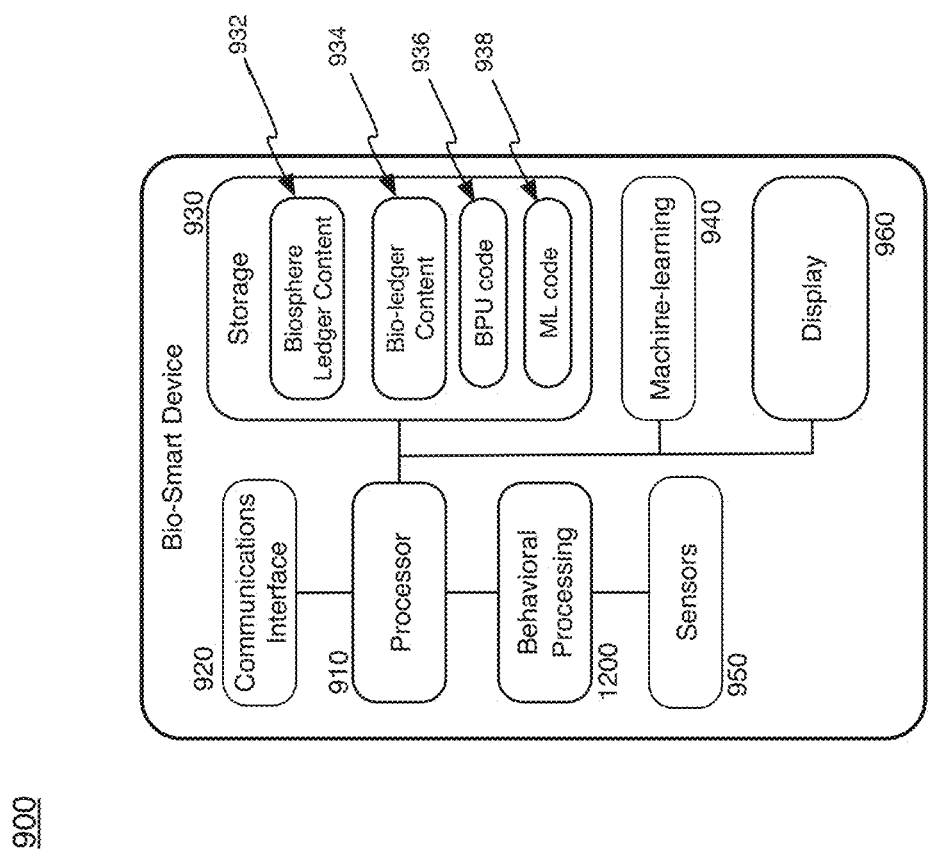
FIG. 9 is an illustration of an example bio-smart device, in accordance with an embodiment.

FIG. 9 is an illustration of an embodiment 900 of an example bio-smart device. In an embodiment, a bio-smart device, such as bio-smart device 900, may analyze and/or otherwise process epigenetic content, such as one or more entries obtained from bio-ledger 492 and/or biosphere ledger 494, and/or behavioral profile content, such as may be derived from one or more sensors, for example, to help manage and/or improve a biological, behavioral, and/or emotional state of an individual, such as user 310. For example, and as described in more detail below, a bio-smart device, such as bio-smart device 900, may, in an embodiment, generate one or more recommendations directed to improvement of a current and/or future epigenetic state of an individual, such as particular user 310, based at least in part on entries obtained from bio-ledger 492 and/or biosphere ledger 494 and/or based at least in part on behavioral profile content, such as may be generated, at least in part, by a behavioral processing unit (BPU), such as BPU 1200, for example.

For example, in an embodiment, a bio-smart device, such as bio-smart device 900, may include at least one processor, such as processor 910. Further, in an embodiment, a bio-smart device, such as bio-smart device 900, may obtain signals and/or states representative of epigenetic content, such as one or more entries from bio-ledger 492 and/or one or more entries from biosphere ledger 494, from a networked device, such as secure storage 400, via a wired and/or wireless network connection utilizing, at least in part, a communications interface, such as communications interface 920. In an embodiment, wireless and/or wired communications may occur substantially in accordance any of a wide range of communication protocols, such as those mentioned herein, for example. In other embodiments, a bio-smart device, such as bio-smart device 900, may not be networked. In embodiments utilizing non-networked bio-smart devices, epigenetic content, such as one or more entries from bio-ledger 492 and/or one or more entries from biosphere ledger 494, may be obtained from an intermediary device, such as intermediary device 700, as explained more fully below.

In an embodiment, a bio-smart device, such as bio-smart device 900, may include a memory, such as memory 930. In an embodiment, memory 930 may comprise a non-volatile memory, for example. Further, in an embodiment, a memory, such as memory 930, may have stored therein executable instructions, such as for one or more operating systems, communications protocols, and/or applications, for example. A memory, such as memory 930, may further store particular instructions, such as BPU code 936, executable by a behavioral processing unit, such as 1200, to generate, at least in part, behavioral profile content. A memory, such as memory 930, may also store particular instructions, such as machine learning (ML) code 938, executable at least in part by a machine-learning device, system, and/or process 940 and/or at least in part by a processor, such as processor 910 and/or BPU 1200, for example. Additionally, in an embodiment, a memory, such as memory 930, may store one or more entries of biosphere ledger content, such as biosphere ledger content 932, and/or one or more entries of bio-ledger content, such as bio-ledger content 934. For example, one or more entries of biosphere ledger content, such as biosphere ledger content 932, and/or one or more entries of bio-ledger content, such as bio-ledger content 934, may be obtained from a secure storage device, such as secure storage device 400, and/or may be generated by a bio-smart device, such as bio-smart device 900. In an embodiment, for a situation in which bio-ledger and/or biosphere ledger content is generated by a bio-smart device, such as bio-smart device 900, bio-ledger and/or biosphere ledger content may be transmitted, such as via communications interface 920, to a secure storage device, such as secure storage device 400, for storage in a particular individual's bio-ledger and/or biosphere ledger. In other embodiments, bio-ledger and/or biosphere ledger content, such as one or more entries of biosphere ledger content 932 and/or one or more entries of bio-ledger content 934, may be transferred from bio-smart device 900 to an intermediary device, such as intermediary device 700.

Although BPU 1200 and/or ML 940 is described as executing instructions, such as BPU code 936 and/or ML code 938, other embodiments of BPUs and/or ML units may not fetch and execute code. In an embodiment, a BPU may include dedicated and/or specialized circuitry for processing sensor content and/or for generating behavioral profile content, as described more fully below. Further, an ML unit may include dedicated and/or specialized circuitry for processing epigenetic content, sensor content, and/or behavioral profile content, for example.

Further, in an embodiment, a bio-smart device, such as bio-smart device 900, may include a display, such as display 960, and/or may also include one or more sensors, such as one or more sensors 950. As utilized herein, "sensors" and/or the like refer to a device and/or component that may respond to physical stimulus, such as, for example, heat, light, sound pressure, magnetism, particular motions, etc., and/or that may generate one or more signals and/or states in response to physical stimulus. Example sensors may include, but are not limited to, one or more cameras, microphones, accelerometers, altimeters, gyroscopes, compasses, thermometers, magnetometers, barometers, light sensors, proximity sensors, hear-rate monitors, perspiration sensors, hydration sensors, breath sensors, etc., and/or any combination thereof. In an embodiment, one or more sensors may monitor one or more aspects of a particular operator's biological and/or behavioral state. Further, in an embodiment, one or more sensors may monitor one or more environmental aspects.

In an embodiment, to generate behavioral profile content for a particular individual, such as user 310, a computing device, such as bio-smart device 900, may obtain signals and/or states representative of content from one or more sensors, such as one or more of sensors 950. Also, in an embodiment, a processor, such as BPU 1200, may process sensor content, such as content from one or more of sensors 150, to generate behavioral profile content for a particular individual. In an embodiment, a processor, such as BPU 1200, may include behavioral content processing circuitry. For example, a processor, such as BPU 1200, may include machine learning acceleration circuitry and/or may operate in conjunction with machine learning circuitry, such as ML unit 940, in an embodiment. BPU 1200 and/or ML unit 940 may also be utilized, at least in part, to process genetic and/or epigenetic content, such as bio-ledger content 934 and/or biosphere ledger content 932, such as, for example, to identify one or more relationships and/or correlations between particular bio-ledger/biosphere content, such as bio-ledger content 934 and/or biosphere ledger content 932, and particular behavioral profile content that may be gleaned, at least in part, from signals and/or states obtained from one or more sensors, such as sensors 950. BPU 1200 and/or ML unit 940 may also be utilized, at least in part, to detect and/or predict changes in an epigenetic state of a particular individual, such as user 310, and/or to generate one or more recommendations directed to improvement of a current and/or future epigenetic state of an individual, such as particular user 310.

For example, a processor, such as BPU 1200 and/or ML 940, may include one or more arithmetic units directed to operations involving relatively larger parameter sets, such as parameter sets that may be employed in machine learning, such as neural networks. In an embodiment, a general-purpose processor, such as processor 910, and/or another processor, such as BPU 1200 and/or ML 940, may comprise separate integrated circuit devices. In other embodiments, a general-purpose processor, such as processor 910, and another processor, such as BPU 1200 and/or ML 940, may be formed on the same integrated circuit die and/or integrated circuit package. Further, in an embodiment, a processor, such as BPU 1200 and/or ML 940, may comprise one or more co-processors that may operate in cooperation with a general-purpose processor, such as 910.

In an embodiment, behavioral profile content, such as may be generated by a BPU, such as BPU 1200, may be communicated between a BPU, such as BPU 1200, and any of a wide range of devices, systems, and/or processes. For example, behavioral profile content generated by BPU 1200 may be stored in a memory, such as memory 930, and/or may be pushed and/or otherwise made available to processor 910, to ML 940, and/or to other devices and/or systems. In an embodiment, behavioral profile content may be communicated via one or more wired and/or wireless communication networks between a computing device, such as bio-smart device 900, and one or more other devices, such as secure storage device 400 and/or intermediary device 700. Of course, subject matter is not limited in scope in these respects.

In an embodiment, behavioral profile content may include a particular specified set of parameters representative of a particular individual's behavioral and/or biological state that may be utilized, at least in part, by any of a wide range of devices, systems, and/or processes for any of a wide range of applications and/or purposes. In an embodiment, by generating a specified set of parameters comprising behavioral profile content, other devices, systems, applications, and/or processes, for example, may be relieved of responsibility for generating behavioral profile content and may, instead, concentrate on particular areas of expertise and/or specialization. For example, application developers may design applications to take advantage of one or more parameters of behavioral profile content for one or more particular operators without having to incur the costs (time, money, resources, etc.) of developing circuitry, code, etc. for gathering and/or processing sensor content and/or for generating behavioral profile content. In an embodiment, a bio-smart device, such as bio-smart device 900, may utilize behavioral profile content at least in part to identify one or more relationships and/or correlations between particular bio-ledger/biosphere content, such as bio-ledger content 934 and/or biosphere ledger content 932, and particular behavioral profile content. Behavioral profile content may also be utilized, at least in part, by a bio-smart device, such as bio-smart device 900, to detect and/or predict changes in an epigenetic state of a particular individual, such as user 310, and/or to generate one or more recommendations directed to improvement of a current and/or future epigenetic state of an individual, such as particular user 310.

In general, bio-smart devices, such as bio-smart device 900, may comprise a relatively "intelligent" bio-smart device. In an embodiment, a bio-smart device may advantageously process and/or otherwise analyze behavioral profile content generated by the bio-smart device with omic content, such as content from a particular individual's bio-ledger and/or biosphere ledger entries, to improve operation and/or output generated by the device and/or to improve resource allocation within the device.

Other embodiments may include a "logging" type device. In an embodiment, a logging-type device may log particular content to one or more particular individual's biosphere ledger and/or bio-ledger. For example, a logging-type device, such as logging-type device 1500 depicted in FIG. 15a and as discussed below, may include a sensor, such as an air quality sensor, and/or may log measurements to a memory store, wherein the memory store includes one or more biosphere ledger entries and/or one or more bio-ledger entries for one or more particular individuals. As discussed more fully below, such logging-type devices may, in an embodiment, be employed across a geographical area and/or may help track particular environmental conditions across a population of individuals, for example. In an embodiment, a logging-device intended to log biosphere and/or bio-ledger entries for a particular individual may comprise a "personal" and/or "private" logging device. In an embodiment, biosphere and/or bio-ledger entries logged by personal logging devices may not generally be shared. On the other hand, for example, a "public" logging device may log biosphere ledger and/or bio-ledger entries intended to be shared among a number of individuals and/or across a population of individuals. Example logging-type devices are discussed more fully, below.

In further embodiments, a bio-smart device may comprise an industrial scale-type bio-smart device. For example, some devices may be too expensive for individuals, in many case, to individually purchase. Industrial-scale type bio-smart devices may process epigenetic and/or behavioral profile content related to multiple particular individuals, and/or may access/write to bio-ledgers and/or biosphere ledgers pertaining to multiple particular individuals. In an embodiment, some logging-type bio-smart devices may also comprise industrial scale-type devices. For example, one or more air quality type of bio-smart devices may be utilized by a number of individuals across a geographical area, as mentioned above. Ownership of a number of air quality sensors would be prohibitive for many individuals. Thus, embodiments that allow for multiple individuals to take advantage of one or more shared bio-smart devices may be desirable. Similarly, bio-smart gymnasium equipment may comprise industrial scale-type and/or intelligent-type bio-smart devices. Other examples of bio-smart devices and/or device types are provided below.

In other embodiments, a particular individual's bio-smart device may operate in conjunction with public devices to write and/or record appropriate content to an individual's biosphere ledger. For example, a bio-smart home water faucet may communicate, such as via a network connection, with a bio-smart water testing device employed at a neighborhood level (e.g., testing device located in water pipe serving a particular neighborhood). A bio-smart faucet may measure a quantity of water flowing into an individual's home and a neighborhood-level bio-smart water testing device may measure water quality and/or particulates. Content generated by both bio-smart devices may be utilized to generate content for one or more individual's biosphere ledgers, in an embodiment. In this manner, a more detailed and/or more comprehensive picture of water purity and/or safety may be established, thereby helping to improve the wellbeing of a number of people.

For another example, a bio-smart refrigerator device may detect a number of containers of a particular product to have been consumed by one or more particular individuals. Bio-smart devices may be located, for example, at a manufacturer of a particular food product. A bio-smart device may, for example, measure aspects related to the food product, and content obtained from the bio-smart device located at the food product manufacturer may be written to and/or recorded in a particular individual's biosphere ledger. Further, for example, a bio-smart refrigerator may detect and/or record an amount of the particular food product removed from the refrigerator by the particular individual. The bio-smart refrigerator may write and/or record the amount of the particular food product to the particular individual's biosphere ledger, in an embodiment. By maintain a ledger, such as a biosphere ledger, containing details related to the particular food product and the amount removed from the refrigerator, for example, a bio-smart device, such as a bio-smart refrigerator, may detect patterns between particular consumed foods and particular changes in epigenetic and/or other omic state for the particular individual, and/or may make recommendations to the individual with respect to dietary intake with the goal of improving the epigenetic and/or other omic state of the individual. In short, a bio-smart device, such as an example bio-smart refrigerator, may help improve the health and/or wellbeing of the individual in ways that conventional refrigerators and/or other devices are not able. Further, coordination of multiple bio-smart type devices may provide opportunities for third-party services to connect content from industrial-type devices with private-device content to generate relatively more comprehensive biosphere ledger entries.

Examples of other types of bio-smart devices that may utilize biological content, sensor content, and/or machine learning, for example, may include, for example, an epigenetics-aware smart scale. For example, a bio-smart weight scale, such as may be designated for human use, may identify pre-diabetic conditions. In an embodiment, a bio-smart weight scale may monitor weight changes and/or may notify an individual at least in part in response to weight changes and/or at least in part due to changes in bio-ledger content (e.g., epigenetic and/or other omic content) indicating a risk of being permanent and/or affecting future offspring at various points in time. In another embodiment, an epigenetics-aware air quality monitor may identify specific sensitives based at least in part on air pollutants and/or epigenetic changes. Further, in an embodiment, an epigenetics-aware breathalyzer/gas sensor may relate epigenetic changes to levels of tobacco, alcohol, and/or other detected chemical compounds. Additionally, in an embodiment, an epigenetics-aware refrigerator may relate epigenetic changes to dietary changes, for example. In another embodiment, an epigenetics-aware alarm clock and/or sleep tracker may warn an individual of damaging changes from repeated sleep patterns. Of course, subject matter is not limited in scope in these respects. In general, embodiments of bio-smart devices, such as bio-smart device 900, may provide improved offerings as compared with non-bio smart counterparts. For example, a conventional scale is not going to be able to indicate when a weight change might affect the health of future offspring and/or indicate when new dietary habits may have adverse and/or positive effects on an individual's health, such as measured by epigenetic and/or other omic changes.

In an embodiment, bio-smart devices may operate with limited computing resources, for example. In an embodiment, it may be advantageous to manage resource allocation to help ensure a device, such as bio-smart device 900, operates within specified storage, computational, and/or energy budgets, and/or to maintain competitive pricing. In an embodiment, bio-ledger content may provide a guide for improved resource allocation techniques and/or for improved content compression techniques. For example, improved content compression techniques may maintain content more relevant to a specified task based, at least in part, on particular bio-ledger content, for example.

In an embodiment, a bio-smart mirror, for example, may utilize epigenetic and/or genetic content to identify, at least in part, mental health issues, disorders, and/or disease. "Bio-smart mirror" refers to a mirror, such as may be used in a bathroom and/or bedroom for personal grooming, for example, that may incorporate one or more sensors (e.g., camera, microphone, etc.) and one or more processors, such as a behavioral processing unit. In an embodiment, a bio-smart mirror may include one or more cameras that may operate in a substantially always-on mode in at least some circumstances. In an embodiment, due at least in part to the sensitive nature of what may be captured by a mirror (e.g., nudity), a bio-smart mirror may not include network connectivity, in an embodiment. In an embodiment, a bio-smart mirror may access bio-ledger and/or biosphere content pertaining to a particular individual via an intermediary device, such as intermediary device 700. From an intermediary device, such as intermediary device 700, a bio-smart device, such as a bio-smart mirror, may obtain a subset of omic content, such as relevant genetic single nucleotide polymorphisms (SNP), epigenetic markers, and/or doctor-described objectives, for example. In an embodiment, an individual, for example, may utilize an intermediary device, such as intermediary device 700, to transfer omic content, such as one or more bio-ledger and/or biosphere ledger entries, from a secure storage device, such as secure storage device 400, to a bio-smart device, such as a non-networked bio-smart mirror.

Further, in an embodiment, a bio-smart mirror may collect sensor content from which an individual's behavior may be inferred, at least in part. For example, a bio-smart mirror may generate two-dimensional image content, three-dimensional image content, etc. In an embodiment, a bio-smart mirror may generate one or more control signals as part of a resource allocation operation based, at least in part, on bio-ledger and/or biosphere ledger content obtained from an intermediary device, such as intermediary device 700. For example, if bio-ledger and/or biosphere ledger content obtained from an intermediary device indicates a genetic mutation at BRCA1 and/or BRCA2 (markers determined to be associated with breast cancer), a bio-smart mirror may focus computing, storage, and/or energy resources, for example, on a task of monitoring and/or predicting breast cancer. Further, for example, if the bio-ledger and/or biosphere content indicates genetic and/or epigenetic markers related to depression, resources may be focused on monitoring depression and/or risk of suicide. In an embodiment, when focusing on breast-cancer identification, a bio-smart mirror may store a few nude images that may be useful for that specific task. When focusing on depression and/or risk of suicide, for example, the mirror might forgo storage of nude images and/or may store content related to wardrobe color and/or tone. That is, in embodiments, resources may be allocated to improve accuracy for personalized, bio-ledger content-guided and/or prioritized tasks. Further, privacy may be promoted due at least in part to non-utilized content being discarded, in an embodiment.

In an embodiment, determinations and/or predictions made by a bio-smart device, such as bio-smart device 900, may be logged directly to an intermediary device, such as intermediary device 700, for later interpretation at a secure storage location, such as at a healthcare provider location, for example, without sharing personal, confidential, and/or sensitive content over a network. In this manner, direct bio-smart device-to-doctor communication may be supported, for example.

Embodiments may provide a number of advantages over other technologies. For example, it may be unrealistic to expect individuals to manually input relatively large amounts of content, such as epigenetic content, and/or to understand which content might be relevant for particular tasks and/or operations that may be accomplished via an electronic device. Therefore, rather than having individuals input epigenetic content to any number of various electronic devices that may seek to operate on such epigenetic content, embodiments may obtain epigenetic content from a centralized storage facility, such as secure storage device 400, for example, and/or from an intermediary device, such as intermediary device 700. Additionally, because a individual's epigenetic and/or other omic content may change over time, it would be unfeasible to expect an individual to input entries whenever additional epigenetic and/or other omic content is generated and/or otherwise available. Also, because, for at least some embodiments, user input of epigenetic content may not be implemented, some embodiments may not include a user interface and/or may include a relatively more simple interface. Further, embodiments may limit epigenetic content communicated to an electronic device to an actionable subset of content, thus maintaining improved levels of privacy.

Issues related to security of personal, sensitive, and/or confidential content, such as epigenetic content, may provide motivation for one or more aspects of various embodiments. For example, improved and/or additional measures may be taken to help ensure legitimate and/or responsible utilization and/or communication of personal, sensitive, and/or confidential content. In an embodiment, an electronic device, such as a secure storage device 400, a bio-smart device 900, and/or an intermediary device 700, may undergo a certification process prior to distribution in the field. For example, by pre-certifying a device and/or by assigning a certified identifier to a device and/or by permitting access to personal, sensitive, and/or confidential content at a certification time, a mechanism may be implemented to restrict access to a subset of content for a particular purpose. In an embodiment, a certification process may include agreements in the use of particular content. For example, a certification process may include an agreement not to sell and/or distribute specified content. Further, in an embodiment, a tokenized security parameter, such as may be communication via an intermediary device, for example, may expire and/or may be become unavailable to a device, such as a bio-smart device, upon disconnection of an intermediary device, thereby terminating a device's ability to further access stored content. Of course, subject matter is not limited in scope in these respects.

Figure 10:
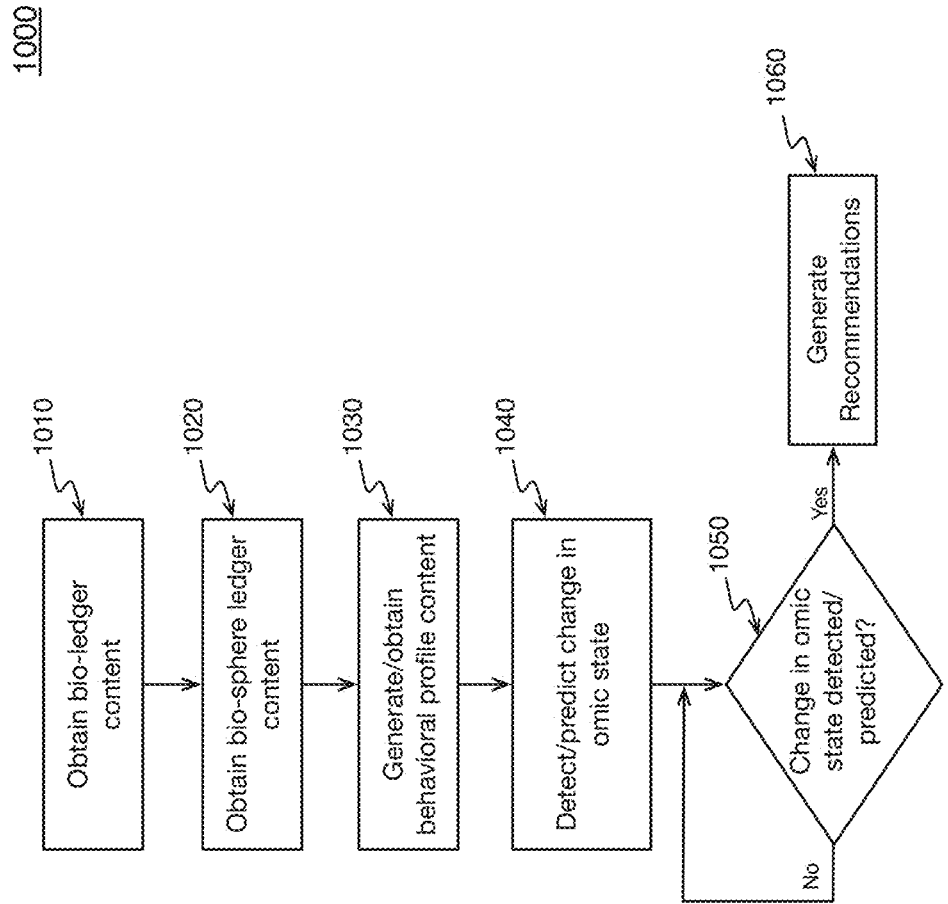
FIG. 10 is an illustration of an example process for detecting and/or predicting a change in epigenetic state, in accordance with an embodiment.

FIG. 10 is an illustration of an embodiment 1000 of an example process for detecting and/or predicting a change in omic state utilizing, at least in part, a bio-smart device, such as bio-smart device 900, with a goal of identifying one or more steps an individual may take to help avoid and/or to help reduce adverse consequences of detected and/or predicted omic state changes in the individual. Embodiments in accordance with claimed subject matter may include all of blocks 1010-1060, fewer than blocks 1010-1060, and/or more than blocks 1010-1060. Further, the order of blocks 1010-1060 is merely an example order, and subject matter is not limited in scope in these respects. As depicted at blocks 1010, epigenetic and/or other omic content, such as in the form of bio-ledger content, may be gathered, generated, and/or otherwise obtained for one or more individuals. Biosphere ledger content may also be gathered, generated, and/or otherwise obtained for one or more individuals, as depicted at block 1020. Embodiments may further employ environmental sensors and/or medical (e.g., genetic, biological, etc.) testing to gather, over a period of time, epigenetic content, such as bio-ledger, and/or content representative of environmental factors, such as one or more biosphere ledger entries, for one or more individuals. Epigenetic and/or environmental content for one or more individuals may be configured in a manner relatively more conducive to identification of relationships, correlations, etc. between epigenetic changes and/or environmental factors. As mentioned, a bio-smart device, such as bio-smart device 900 may obtain bio-ledger and/or biosphere ledger content pertaining to a particular individual at least in part via communication with an electronic device, such as secure storage device 400 and/or intermediary device 700. For example, bio-ledger and/or biosphere content may be transmitted over a network, such as the Internet, via wired and/or wireless communication of signal packets and/or signal frames, such as between communication interface 420 of secure storage device 400 and communication interface 920 of bio-smart device 900. Further, for example, bio-ledger and/or biosphere content obtained from a secure storage device, for example, may be stored as signals and/or states in one or more non-transitory memories, such as memory 930.

Further, as depicted at block 1030, behavioral profile content may be generated and/or otherwise obtained. As mentioned, a bio-smart device, such as bio-smart device 900, may generate behavioral profile content based at least in part on content, such as signals and/or states, obtained from one or more sensors, such as sensors 950. For example, content obtained from one or more sensors, such as sensors 950, may be processed by particular hardware circuitry, such as BPU 1200 and/or ML 940, to generate behavioral profile content representative of a particular individual's physical, mental, and/or emotional state. In an embodiment, behavioral profile content may include a plurality of parameters representative of focal point, excitement, anger, fear, fatigue, dehydration, or focus/distraction, or any combination thereof, in relation to a particular individual. Behavioral profile content may further include, by way of additional non-limiting examples, parameters representative of pre-breakthrough, silent like (e.g., implied satisfaction by an individual with respect to particular consumed content), regret, error acknowledgment, hunger, sloppiness/precision, empathy, and/or social engagement level, or any combination thereof. Particular circuitry, such as BPU 1200, is described below in connection with generation of behavioral profile content and/or with processing of sensor content.

As depicted at block 1040, for example, epigenetic and/or other omic content, such as bio-ledger content and/or biosphere ledger content for one or more particular individuals, along with behavioral profile content for one or more particular individuals, may be analyzed and/or otherwise processed at least in part to detect and/or predict changes in epigenetic state for one or more individuals. In an embodiment, epigenetic and/or behavioral profile content, for example, may be analyzed and/or otherwise processed at least in part utilizing BPU 1200, processor 910, and/or ML 940. In an embodiment, machine learning and/or other analytic techniques may process time-stamped entries from a bio-ledger and/or biosphere ledger for one or more particular individuals and/or may process behavioral profile content corresponding at particular points in time to one or more time-stamped bio-ledger and/or biosphere ledger entries, such as content 932 and/or 934, to identify relationships and/or correlations, for example, between bio-ledger and/or biosphere ledger content and behavioral profile content. Further, a bio-smart device, such as bio-smart device 900, may detect and/or predict, at least in part, a change in epigenetic and/or other omic state for one or more particular individuals. In an embodiment, a detection and/or prediction of a change in epigenetic and/or other omic state for a particular individual may be based, at least in part, on one or more identified relationships and/or correlations between changes in epigenetic and/or other omic state and changes in environmental influencers and/or changes in behavioral profile content. Further, detection and/or prediction of a change in epigenetic and/or other omic state for a particular individual may be accomplished at least in part utilizing BPU 1200, processor 910, and/or ML 940.

As depicted at block 1050, a determination may be made utilizing BPU 1200, processor 910, and/or ML 940 as to whether a change in epigenetic and/or other omic state for one or more particular individuals has been detected and/or predicted. At least in part in response to a determination that a change in epigenetic and/or other omic state has been detected and/or predicted, one or more recommendations directed to improving a current and/or future epigenetic and/or other omic state of one or more particular individuals may be generated utilizing, at least in part, BPU 1200, processor 910, and/or ML 940, as indicated at block 1060. In an embodiment, generated recommendations may be communicated to one or more particular individuals and/or to one or more other authorized individuals and/or entities, such as relatives, caregivers, health professionals, insurance companies, etc. In an embodiment, authorization for dissemination of generated recommendations may be made by one or more particular individuals, such as user 310.

In an embodiment, a device, such as bio-smart device 900, may periodically, regularly, and/or occasionally, for example, present an individual, such as user 310, with one or more brain-game type problems via an interface, such as via display 960 and/or via other interfaces that may interact with bio-smart device 900. For example, audio and/or video content may be presented to an individual via a television, phone, tablet, etc., by way of communications interface 920, in an embodiment. In an embodiment, one or more sensors, such as sensors 950, may be utilized to collect behavioral content. A processor, such as BPU 1200, may generate behavioral profile content for a particular individual, such as user 310, based, at least in part, on signals and/or states obtained from one or more sensors, such as sensors 950. For example, during presentation of a brain-game to an individual (e.g., an individual may read a passage of text and/or answer particular questions), sensor content, such as from one or more cameras, for example, may be gathered, and/or behavioral profile content may be generated. In an embodiment, behavioral profile content may indicate eye movement, such as blink duration, darting, blinking rate, ability to focus, pupil dilation, etc. Additional behavioral profile content may be generated based, at least in part, on signals and/or states obtained from a microphone sensor. For example, behavioral profile content may indicate speech tonality, sentiment, volume, frequency, etc.

As mentioned, behavioral profile content, such as may be generated in response to brain-game type interactions with an individual, for example, may be gathered over a period of time. In an embodiment, over a period of time, behavioral profile content may be monitored and/or tracked. Changes in epigenetic markers (e.g., as indicated by bio-ledger content) may also be monitored and/or tracked. In an embodiment, monitored and/or tracked changes in epigenetic content and/or monitored and/or tracked behavioral profile content may be provided to machine-learning devices, systems, and/or processes, and/or may be provided to other analysis devices, systems, and/or processes. For example, via machine-learning training, correlations and/or relationships between behavioral profile content and epigenetic state and/or changes in epigenetic markers may be determined. In an embodiment, behavioral profile content may comprise machine learning inputs, and epigenetic state content may comprise machine learning output classification. In an embodiment, once trained, a machine-learning device, system, and/or process may detect and/or predict changes in epigenetic state based at least in part on behavioral content. In some embodiments, changes in epigenetic state may be predicted and/or detected based solely on behavioral profile content, although subject matter is not limited in scope in this respect. Further, as mentioned, embodiments may involve additional and/or other types of omic content, such as, for example, microbiome, proteome, metabolome, and/or transcriptome content.

Although embodiments described herein may utilize behavioral profile content, such as may be generated via a behavioral processing unit, such as BPU 1200, subject matter is not limited in this respect. Content representative of behavior for an individual may be utilized in various embodiments regardless of show such content may be generated and/or otherwise obtained. Further, although some embodiments described herein describe generating behavioral profile content via a behavioral processing unit, such as BPU 1200, embodiments may also make use of behavioral processing units, such as BPU 1200, to detect and/or predict changes in omic state. For example, machine learning units in a BPU, such as BPU 1200, may be utilized to identify relationships and/or correlations between behavioral profile content and changes in omic state and/or to detect and/or predict changes in omic state based at least in part on behavioral profile content.

As mentioned, embodiments including personal bio-ledgers and/or biosphere ledgers may provide recommended, standardized, and/or otherwise specified manners of tracking, monitoring, storing, and/or representing, for example, an individual's epigenetic content and/or environmental influencers such that science and/or analytics, for example, may continue to determine relationships and/or correlations between an individual's environmental factors and changes in personal biological content, for example. In embodiments, more frequent behavioral monitoring to detect and/or predict changes in epigenetic state, such as via one or more bio-smart devices, may result in a shorter time-to-identification of such changes. Further, behavioral monitoring, such as via one or more bio-smart devices, may be utilized to guide relatively more limited, and therefore relatively less expensive, epigenetic testing due, at least in part, to indications by bio-smart devices that such testing may be advisable.

Further, embodiments may be implemented not only with human beings in mind, but may also be implemented with an eye to agriculture. For example, plants may undergo epigenetic changes as they develop, and/or may be relatively more heavily dependent on changes in gene expression in order to respond to environmental stimuli. Further, other epigenetic phenomena may be plant-specific and/or may be agriculturally important. For example, an induction of flowering in plants in response to an experience of prolonged cold temperatures (e.g., winter) may include a physiological phenomenon referred to as vernalization, which may have an epigenetic basis. In embodiments, behavioral indicators for a plant, such as a crop, may be measured (e.g., via one or more cameras) relatively less expensively. Behavioral indicators may be utilized, at least in part, to predict and/or detect changes in a plant's epigenetic state. In embodiments, predictions and/or detections of changes in epigenetic state may allow farmers, for example, to determine more appropriate time to harvest, time to fertilize, when to shade, state of dormancy, etc., to name a few non-limiting examples. In embodiments, a bio-smart device, such as bio-smart device 900, may generate recommendations based on monitored behavioral content pertaining to a particular crop, for example, with a goal of improving yield, improving quality, reducing costs, etc.

Figure 11:
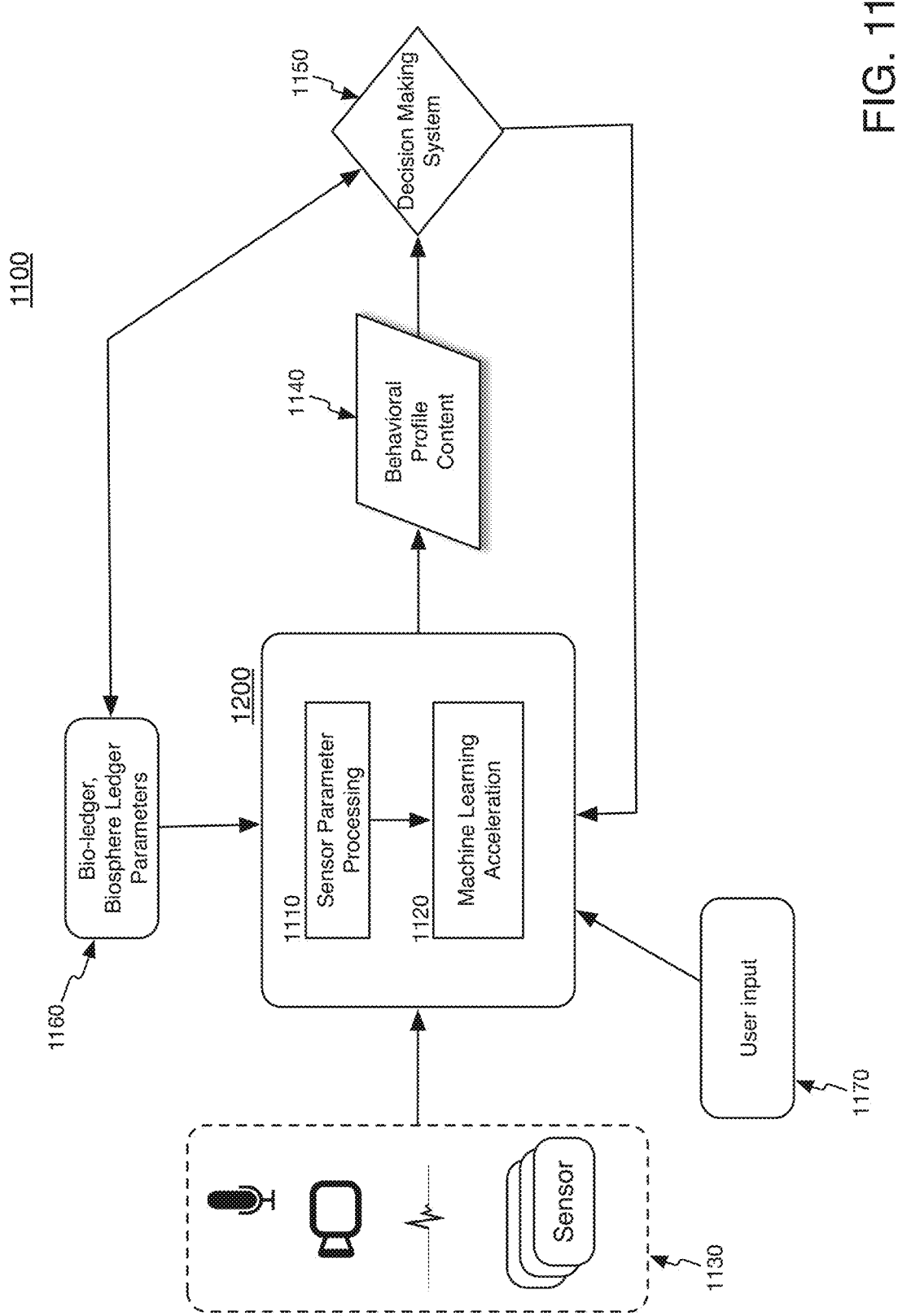
FIG. 11 is an illustration of an example device, system, and/or process for processing signals and/or states representative of epigenetic content and/or behavioral content, in accordance with an embodiment.

FIG. 11 is an illustration of an embodiment 1100 of an example device, system, and/or process for processing signals and/or states representative of epigenetic content and/or behavioral content, in accordance with an embodiment. In an embodiment, to generate behavioral profile content, such as behavioral profile content 1140, for a particular individual, a processor, such as behavioral processing unit 1200, may obtain signals and/or states representative of content from one or more sensors, such as one or more of sensors 1130. Also, in an embodiment, a processor, such as behavioral processing unit 1200, may process sensor content, such as content from one or more of sensors 1130, to generate behavioral profile content, such as behavioral profile content 1140, for a particular individual. In an embodiment, a processor, such as behavioral processing unit 1200, may include behavioral content processing circuitry. For example, a processor, such as behavioral processing unit 1200, may include sensor parameter processing circuitry, such as circuitry 1110, and/or may include machine learning acceleration circuitry, such as circuitry 1120, in an embodiment.

In an embodiment, a processor, such as behavioral processing unit 1200, may provide circuitry to generate, at least in part, behavioral profile content, such as behavioral profile content 1140, for a particular individual to be utilized for any of a wide range of possible applications, such as example applications described herein. For example, in an embodiment, behavioral profile content may be provided to a decision-making device, process, and/or system, such as decision-making device, system, and/or process 1150. In an embodiment, a processor, such as behavioral processing unit 1200, may relatively more efficiently process signals and/or states obtained from one or more behavioral, biological, and/or environmental sensors, or a combination thereof, associated with a particular individual and/or a particular environment, for example. In an embodiment, a processor, such as behavioral processing unit 1200, may calculate probabilities for "hidden" (e.g., emotional and/or biological) states of a particular operator at least in part by generating behavioral profile content, such as behavioral profile content 1140, that may be utilized by one or more devices, systems, and/or processes, such as decision-making device, system, and/or process 1150, for any of a wide range of possible purposes.

For example, as mentioned, behavioral profile content for a particular individual may be tracked, wherein the behavioral profile content may include a plurality of parameters representative of a current behavioral state or biological state, or a combination thereof, of the particular individual. Further, in an embodiment, one or more relationships and/or correlations between tracked behavioral profile content and bio-ledger and/or biosphere content 1160 may be determined, for example. An embodiment may further include generating one or more recommendations for actions that may be taken, such as by a user and/or by other individuals, for example, to improve of a current and/or future epigenetic state of a particular individual. In an embodiment, a decision-making system, device, and/or process, such as system 1150, may generate one or more recommendations based, at least in part, on bio-ledger and/or biosphere content 1160 and/or based, at least in part, on behavioral profile content 1140. Further, in an embodiment, recommendations may be made, at least in part, utilizing behavioral processing unit 1200. Additionally, in an embodiment, user input 1170 may be obtained for any of a range of purposes. For example, an individual, such as user 310, may provide explicit content related to particular activities and/or substances consumed, for example. Further, an individual, such as user 310, may provide input, such as user input 1170, to configure, guide, and/or focus one or more aspects of epigenetic and/or behavioral profile content processing, in an embodiment. Of course, subject matter is not limited in scope in these respects.

In an embodiment, machine-based decision-making, such as decision-making device, system, and/or process 1150, may, for example, include dynamic recommendation of particular activities, dietary supplementation and/or modification, etc., for a particular individual with a goal of improving a current and/or subsequent state of the particular individual. In an embodiment, dynamic recommendation of particular activities, dietary supplementation and/or modification, etc., for a particular individual may be based, at least in part, on behavioral profile content and/or may be based, at least in part, on bio-ledger and/or biosphere ledger content 1160. In an embodiment, sensor content may comprise content from any of a wide range of possible sources and/or that may be variable. In an embodiment, a processor, such as behavioral processing unit 1200, may incorporate machine-learning (e.g., neural networks, etc.) at least in part to adapt to the presence and/or absence of one or more particular sensors while providing probabilities, for example, represented at least in part by behavioral profile content.

In an embodiment, machine-based decision-making, such as may be performed by decision-making device, system, and/or process 1150, for example, may depend at least in part on a individual's current state and/or a individual's ability to relatively quickly respond to changes in the individual's state. A wide range of possible sensor types may provide content representative of various aspects of a particular operator's biological and/or behavioral state, and/or representative of one or more environmental factors and/or other external factors. In an embodiment, a processor, such as behavioral processing unit 1200, may include a sensor parameter processing unit, such as sensor parameter processing unit 1110. In an embodiment, a sensor parameter processing unit, such as sensor parameter processing unit 1110, may obtain signals and/or states from one or more sensors, such as sensors 1130, and/or may process signals and/or states from one or more sensors to combine, coordinate, normalize and/or otherwise condition signals and/or states from one or more sensors.

Further, a sensor parameter processing unit, such as sensor parameter processing unit 1110, may prepare sensor content for further processing, such as via machine learning operations. In an embodiment, machine learning acceleration circuitry, such as machine learning acceleration circuitry 1120, may, at least in part, process sensor content to infer a substantially current biological and/or behavioral state of a particular operator. For example, a camera sensor and/or the like may provide one or more signals and/or states to a sensor parameter processing unit, such as sensor parameter processing unit 1110. Sensor parameter processing unit 1110 may generate one or more parameters representative of pupil dilation, focal point, blink duration, and/or blink rate, or any combination thereof, for example.

In an embodiment, machine learning acceleration circuitry, such as machine learning acceleration circuitry 1120, may generate, at least in part, a representation of a particular operator's biological and/or behavioral state, such as behavioral profile content 1140. In an embodiment, behavioral profile content, such as behavioral profile content 1140, may comprise a specified set of parameters that may be utilized by any of a wide range of machine-based (e.g., computing device-based) decision making systems, devices, and/or processes, such as decision-making device, system, and/or process 1150. In an embodiment, behavioral profile content may include a plurality of parameters representative of focal point, excitement, anger, fear, fatigue, dehydration, or focus/distraction, or any combination thereof, in relation to a particular individual. Behavioral profile content may further include, by way of additional non-limiting examples, parameters representative of pre-breakthrough, silent like, regret/error acknowledgment, hunger, sloppiness/precision, empathy, and/or social engagement level, or any combination thereof.

In an embodiment, behavioral profile content may comprise a specified set of parameters, such as at least a subset of those mentioned above, for example. In an embodiment, a processor, such as behavioral processing unit 1200, may generate a set of parameters representative of behavioral profile content specified in a manner so as to provide content regarding a particular individual's behavioral and/or biological state to any of a wide range of devices, systems, and/or processes for any of a wide range of purposes and/or applications. Further, such a set of specified behavioral profile content parameters may be utilized concurrently by any number of devices, systems, and/or processes.

In an embodiment, a processor, such as behavioral processing unit 1200, may repetitively obtain sensor content and/or may repetitively generate behavioral profile content for a particular individual. For example, sensor content may be gathered and/or otherwise obtained at regular and/or specified intervals, and/or behavioral profile content may be generated at regular and/or specified intervals. In an embodiment, one or more devices, systems, and/or processes may track behavioral profile content over a period of time, for example, such as to detect changes in behavioral profile content, for example. Similarly, in an embodiment, one or more devices, systems, and/or processes may track bio-ledger and/or biosphere content over a period of time, for example.

In an embodiment, a processor, such as behavioral processing unit 1200, may be advantageously utilized at least in part by dedicating computing resources to process sensor content, for example, and/or to generate behavioral profile content, such as 1140, for a particular individual. Further, by generating a specified set of parameters comprising behavioral profile content, such as 1140, systems, devices, and/or processes may be relieved of responsibility for generating behavioral profile content and may, for example, concentrate on particular areas of expertise and/or specialization, for example. Further, development costs may be reduced for systems, devices, and/or processes at least in part due to having a specified set of behavioral profile content parameters available from a processor, such as behavioral processing unit 1200.

In an embodiment, a processor, such as behavioral processing unit 1200, may merge substantially real-time sensor content (e.g., behavioral and/or biological sensor content, or a combination thereof) with representations of prior relationships (e.g., known and/or determined connections between that which may be measured and/or human states). Also, in an embodiment, a processor, such as behavioral processing unit 1200, may utilize machine learning techniques (e.g., neural networks, etc.) to map incoming sensor content representative of one or more aspects of an operator's biological and/or behavioral state. In an embodiment, a processor, such as behavioral processing unit 1200, may include support for relatively more efficient coordination and/or processing of content obtained from a wide range of possible sources (e.g., combination of content from biological and/or behavioral sensors and/or content representative of other factors) to generate a specified set of parameters, such as behavioral profile content 1140. Further, in an embodiment, one or more memory devices may be provided to store operator-dependent and/or operator-independent content to enable relatively quicker identification of state changes in a particular individual.

In an embodiment, machine learning operations such as may be performed by a processor, such as behavioral processing unit 1200, for example, may store user-specific content in one or more memory devices and/or may also store user-generic content (e.g., determined and/or substantially known relationships between sensor content and/or user states). In an embodiment, user-specific content and/or user-generic content may be processed, such as via machine learning operations, to generate one or more output state vectors, such as behavioral profile content 1140.

In an embodiment, one or more external factors may come in to play with respect to generating behavioral profile content and/or decision-making. For example, one or more parameters indicative of one or more external factors may be obtained by a behavioral profile unit, such as BPU 1200, and/or by a decision-making device, system, and/or process, such as decision-making system 1150. Parameters representative of external factors may include, for example, parameters representative of location, time of day, presence and/or identity of external individual, and/or general sentiment.

Figure 12:
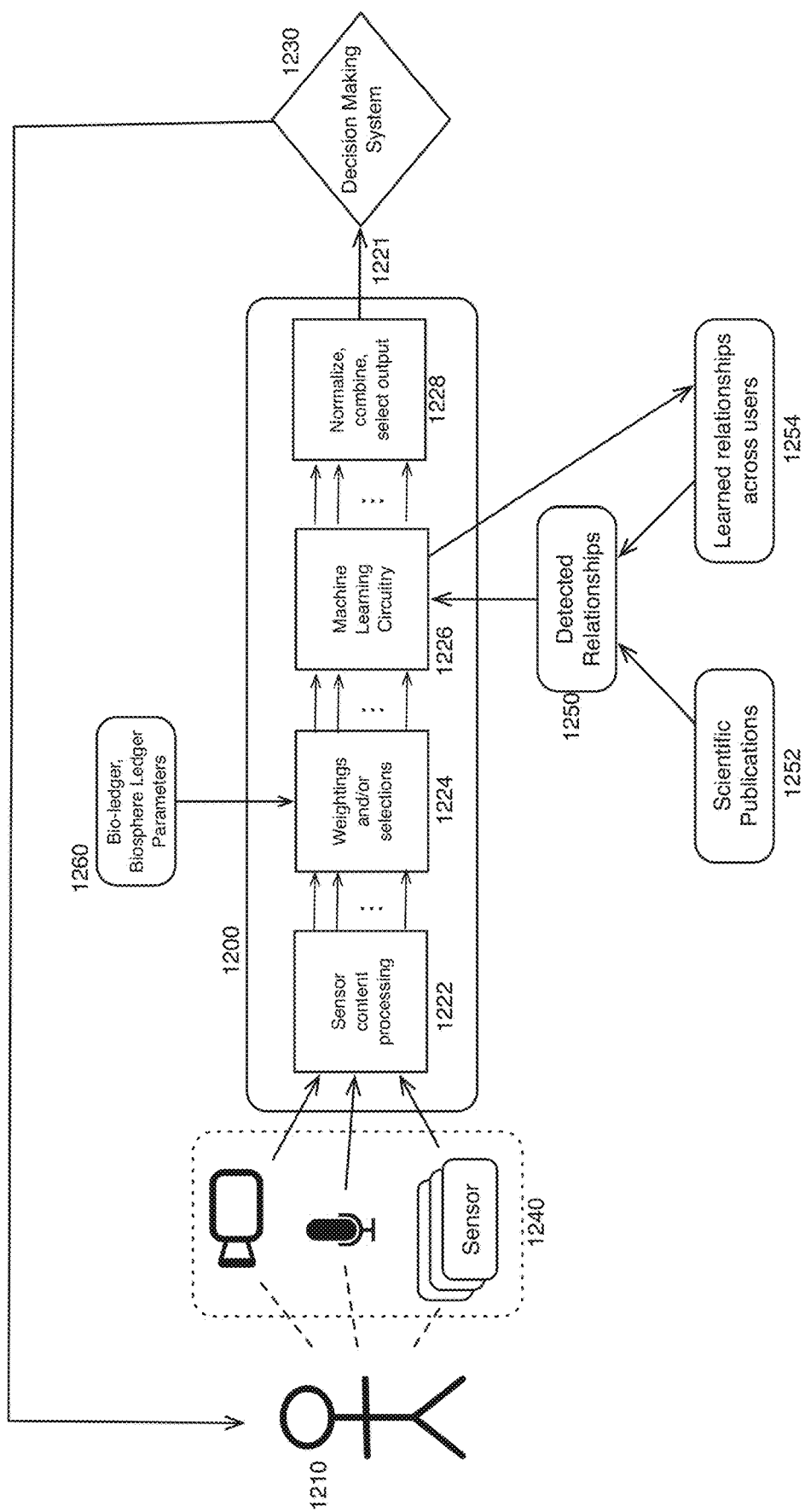
FIG. 12 is an illustration of an example device, system, and/or process for processing signals and/or states representative of epigenetic content and/or behavioral content, in accordance with an embodiment.

FIG. 12 is an illustration of an embodiment 1200 of an example device, system, and/or process, such as a behavioral processing unit (BPU), for processing signals and/or states representative of epigenetic content and/or behavioral content. An embodiment, such as BPU 1200, may include a processor, such as a BPU 1200, to process signals and/or states representative of behavioral content in a computing device. In an embodiment, to generate behavioral profile content, such as behavioral profile content 1221, for a particular individual, such as user 1210, a processor, such as behavioral processing unit 1200, may obtain signals and/or states representative of content from one or more sensors, such as one or more of sensors 1240. Also, in an embodiment, a processor, such as behavioral processing unit 1200, may process sensor content, such as content from one or more of sensors 1240, to generate behavioral profile content, such as behavioral profile content 1221, for a particular individual. In an embodiment, a processor, such as behavioral processing unit 1200, may include behavioral content processing circuitry. For example, a processor, such as behavioral processing unit 1200, may include sensor content processing circuitry, such as circuitry 1222, and/or may include machine learning circuitry, such as circuitry 1224 and/or 1226, in an embodiment. In an embodiment, a processor, such as BPU 1200, may further obtain content from sensors, such as sensors 1240, to track one or more environmental aspects (e.g., environmental sound, temperature, barometric pressure, altitude, location, etc.).

In an embodiment, a processor, such as behavioral processing unit 1200, may provide circuitry to generate, at least in part, behavioral profile content, such as behavioral profile content 1221, for a particular individual, such as user 1210, to be utilized for any of a wide range of possible applications and/or purposes. For example, a processor, such as behavioral processing unit 1200, may generate behavioral profile content, such as behavioral profile content 1221, to, at least in part, to identify changes in epigenetic state within a human body, for example. In an embodiment, behavioral profile content, such as behavioral profile content 1221, may include one or more parameters indicative of eye movement, voice and/or speech aspects, environmental sounds, etc. Of course, subject matter is not limited in scope in these respects.

In an embodiment, one or more sensors, such as sensors 1240, may provide content representative of various aspects of a particular operator's biological and/or behavioral state, and/or representative of one or more environmental factors and/or other external factors. In an embodiment, sensors 1240 may include one or more sensors of one more sensor types, as previously mentioned. Further, in an embodiment, a processor, such as behavioral processing unit 1200, may include circuitry, such as circuitry 1222, to process content obtained from one or more sensors, such as sensors 1240. In an embodiment, content obtained from sensors, such as sensors 1240, may include digital signals and/or states, analog signals and/or states, or any combination thereof. For example, circuitry 1222 may include digital circuitry, analog circuitry, or a combination thereof. In an embodiment, sensor content processing circuitry, such as circuitry 1222, may convert one or more analog signals to digital signals, although subject matter is not limited in scope in this respect. In an embodiment, circuitry, such as circuitry 1222, may process signals and/or states from one or more sensors, such as sensors 1240, to combine, coordinate, normalize, amplify, filter, and/or otherwise condition signals and/or states from one or more sensors, such as sensors 1240, although subject matter is not limited in scope in these respects.

Further, in an embodiment, a processor, such as behavioral processing unit 1200, may include circuitry for determining and/or selecting weighting parameters and/or for determining and/or selecting particular machine learning devices, systems, and/or processes. For example, circuitry 1224 may determine and/or select one or more particular machine learning techniques, such as one or more particular neural networks and/or including one or more weighting parameters, for example, for use in machine learning operations. In an embodiment, determination and/or selection of weighting parameters and/or machine learning operations, including one or more neural networks, for example, may be based, at least in part, on content, such as parameters 1260, representative of bio-ledger and/or biosphere content pertaining to a particular individual, such as user 1210.

In an embodiment, machine learning circuitry such as machine learning circuitry 1226 may, at least in part, process content, such as content that may be obtained from circuitry 1222 and/or 1224, to determine, estimate, and/or infer, for example, one or more parameters representative of a substantially current biological and/or behavioral state of a particular individual. In an embodiment, machine learning circuitry, such as machine learning circuitry 1226, may generate, at least in part and/or with contribution from output generation circuitry 1228, a representation of a particular individual's biological and/or behavioral state, such as behavioral profile content 1221. In an embodiment, behavioral profile content, such as 1221, may include a plurality of parameters representative of focal point, excitement, anger, fear, fatigue, dehydration, or focus/distraction, pre-breakthrough, silent like, regret/error acknowledgment, hunger, sloppiness/precision, empathy, or social engagement level, or any combination thereof, for example. In an embodiment, a processor, such as behavioral processing unit 1200, may repetitively and/or substantially periodically obtain sensor content and/or may repetitively and/or substantially periodically generate behavioral profile content, such as behavioral profile content 1221, for a particular individual, such as user 1210. Further, as mentioned, behavioral profile content, such as behavioral profile content 1221, may include one or more parameters indicative of voice tonality, voice sentiment, volume, frequency, pitch, timbre, etc. Further, as also mentioned, behavioral profile content, such as behavioral profile content 1221, may include one or more parameters representative of eye darting, blinking rate, ability to focus, and/or pupil dilation, to name a few additional non-limiting examples.

In an embodiment, a processor, such as behavioral processing unit 1200, may determine appropriate weights for various sensor combinations and/or for particular parameters, such as bio-ledger and/or biosphere ledger content 1260, during offline training operations, for example. In another embodiment, during online operation, for example, a set of inputs may be logged and/or later used as training parameters. For example, an individual, such as user 1210, may explicitly provide inputs related to supplementation and/or consumption of particular substances and/or may provide inputs related to particular behaviors for a particular individual, for example. Further, in an embodiment, determined and/or substantially known relationships, such as relationships represented by parameters 1250, may include relationships between behavioral profile content and/or user states and/or may include scientifically determined relationships. For example, scientific publications may provide research results indicative of relationships between changes in epigenetic and/or other omic state and particular environmental and/or behavioral factors. In an embodiment, parameters 1254 representative of other relationships may be determined across multiple individuals and/or across populations, for example.

Figure 13:
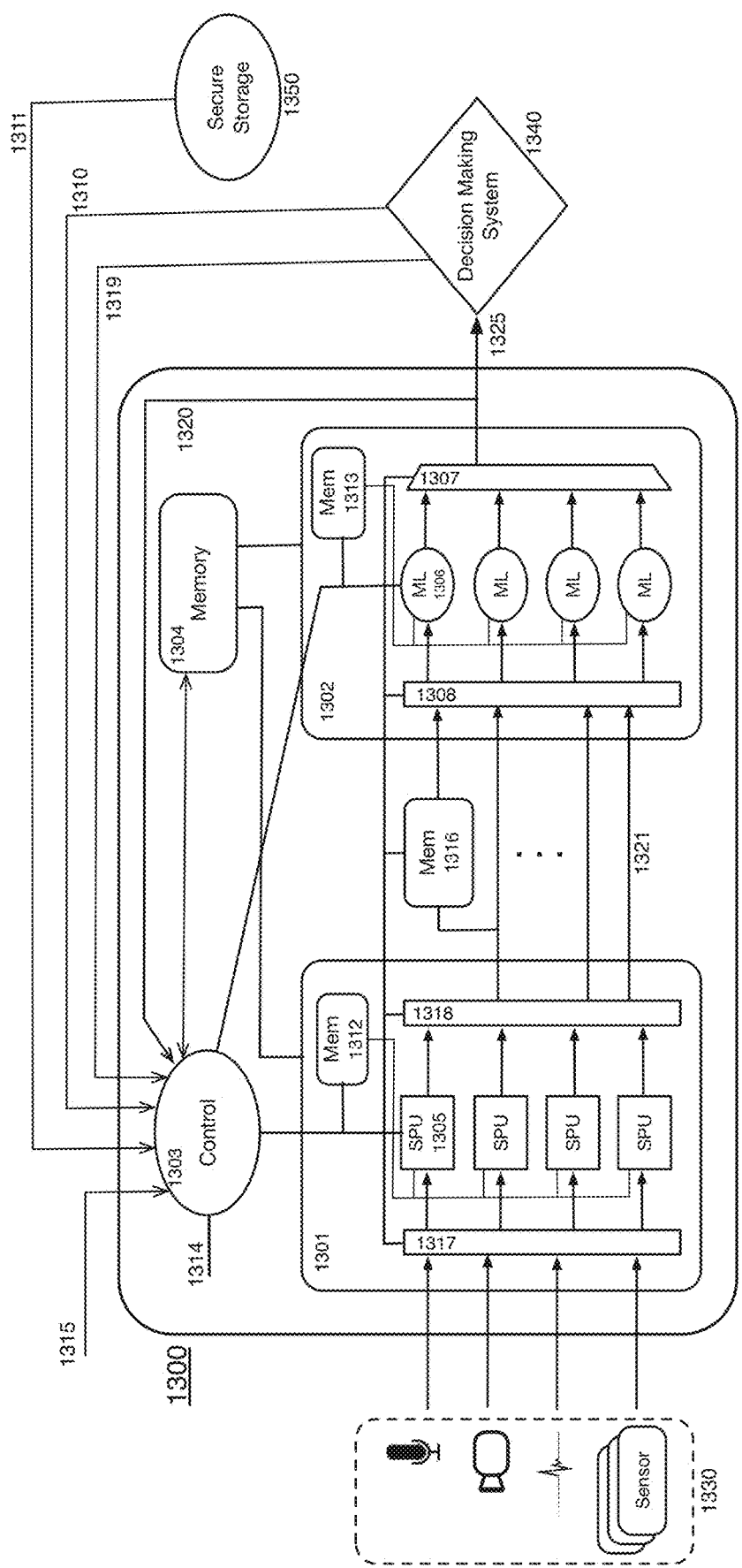
FIG. 13 is an illustration of an example device, system, and/or process for processing signals and/or states representative of epigenetic content and/or behavioral content, in accordance with an embodiment.

FIG. 13 is an illustration of an embodiment 1300 an example device, system, and/or process for processing signals and/or states representative of epigenetic content and/or behavioral content, in accordance with an embodiment. For example, FIG. 13 includes a schematic block diagram depicting an embodiment 1300 of an example device, such as a behavioral processing unit, for processing content, such as content obtained from sensors 1330, to generate signals and/or states representative of behavioral content in a computing device. In an embodiment, a behavioral processing unit, such as BPU 1300, may be implemented in a bio-smart device, such as bio-smart device 900, in a secure storage device, such as secure storage device 400, and/or in any of a wide range of electronic device types, for example. Further, in an embodiment, a behavioral processing unit, such as BPU 1300, may be utilized to process epigenetic content in connection with behavioral profile content, while in other embodiments a behavioral processing unit, such as BPU 1300, may operate on epigenetic content in the absence behavioral content.

In an embodiment, a processor, such as behavioral processing unit 1300, may process digital signals and/or states or analog signals and/or states, or a combination thereof (e.g., mixed-signal). Any of a wide range of digital and/or analog circuit types may be utilized to process digital, analog, and/or mixed-signal signals and/or states, as explained more fully below. In an embodiment, one or more aspects of a processor, such as behavioral processing unit 1300, may be implemented to operate in an analog domain, while one or more other aspects may be implemented to operate in a digital domain. In other embodiments, a processor, such as behavioral processing unit 1300, may be implemented to operate substantially wholly in the digital domain and/or the analog domain.

In an embodiment, a processor, such as behavioral processing unit 1300, may, in general, substantially continuously obtain content from sensors, such as one or more sensors 1330, and/or may substantially continuously generate output signals and/or states, such as behavioral profile content 1325. Generated output signals and/or states, such as behavioral profile content 1325, may be made available to one or more decision-making systems, such as decision-making system 1340, for example. In an embodiment, a decision-making device, system, and/or process, such as decision-making system 1340, may determine, at least in part via at least one processor performing one or more machine learning operations, one or more relationships between tracked behavioral profile content, such as behavioral profile content 1325 and bioavailability and/or balance, or a combination thereof, of one or more particular substances within a particular individual's body. An embodiment may further include a decision-making device, system, and/or process, such as decision-making system 1340, to analyze and/or otherwise process behavioral profile content, such as content 1325, in combination with epigenetic content, such as bio-ledger and/or biosphere content 1311, for example, to detect and/or predict changes in epigenetic state for one or more individuals. Further, in embodiments, content, such as behavioral profile content for one or more individuals, may be analyzed and/or otherwise processed in combination with epigenetic content, for example, to generate recommendations with respect to one or more individuals. In embodiments, recommendations may be directed at improving a current and/or future epigenetic state of one or more individuals. In other embodiments, content, such as behavioral profile content for a particular individual, may be analyzed and/or otherwise processed in combination with epigenetic content, for example, to generate recommendations for a particular individual directed to the particular individual's behavioral and/or biological state.

In an embodiment, a sensor parameter processing stage, such as sensor parameter processing stage 1301, may obtain signals and/or states (e.g., digital, analog, and/or mixed-signal) from one or more sensors, such as sensors 1330. In an embodiment, a sensor parameter processing stage, such as sensor parameter processing stage 1301, may process signals and/or states from one or more sensors at least in part by combining content, adjusting timing, performing noise reductions and/or other signal reduction operations, normalizing content, or any combination thereof, for example. However, subject matter is not limited in scope in this respect.

Further, in an embodiment, sensor content steering circuitry, such as sensor content steering circuitry 1317, may direct signals and/or states obtained from sensors, such as from sensors 1330, to one or more sensor processing units, such as one or more of sensor processing units (SPU) 1305. In an embodiment, sensor processing units, such as SPUs 1305, may be configured via one or more control signals, such as control signals communicated between a control unit, such as control unit 1303, and sensor processing units, such as SPUs 1305. Sensor processing units, such as SPUs 1305, may prepare sensor content, such as signals and/or stated obtained from one or more sensors, such as sensors 1330, for further processing by, for example, a machine-learning processing stage, such as machine-learning processing stage 1302. In an embodiment, sensor content steering circuitry, such as sensor content steering circuitry 1317, may direct content based, at least in part, on one or more control signals obtained from a control unit, such as control unit 1303, and/or from a memory, such as memory 1312, for example.

In an embodiment, a sensor processing stage, such as sensor processing stage 1301, may include one or more sensor processing units, such as sensor processing units 1305, that may be configured to operate individually or in one or more various combinations. Sensor processing units, such as SPUs 1305, may perform, individually and/or in cooperation, any of a variety of operations that may be specified and/or implemented. Such operations may include, for example, combining signals and/or states, adjusting timing of signals and/or states, performing noise reductions and/or other signal reduction operations, and/or normalizing content, to list but a few examples.

One or more sensor processing units, such as SPUs 1305, may be implemented to operate in an analog domain and/or one or more units may be implemented to operate in a digital domain. In an embodiment, sensors, such as sensors 1330, may provide signals and/or states comprising analog signals and/or comprising digital content (e.g., signals and/or states). Further, in an embodiment, one or more analog signals obtained by one or more sensors, such as 1330, may be converted to digital content using analog-to-digital conversion circuitry. In other embodiments, analog signals obtained from sensors, such as sensors 1330, for example, may be maintained as analog signals for processing by one or more sensor processing units, such as SPUs 1305. Further, in an embodiment, individual sensor processing units, such as SPUs 1305, may be implemented in analog and/or digital based, at least in part, on particular tasks to be performed by a particular SPU and/or based, at least in part, on particular signal types to be obtained from sensors, such as sensors 1330. In an embodiment, one or more of a variety of filters, signal amplifiers, and/or signal damping circuits, ranging from relatively more simple to relatively more complex, for example, may be performed by one or more particular sensor processing units, such as SPUs 1305. Sensor processing unit operations, such as example operations mentioned herein, may have particular relevance in a larger context of behavioral profile content generation in connection with one or more machine-learning units. For example, sensor processing unit operations may be performed with an end-goal of behavioral profile content generation in mind.

In an embodiment, a particular sensor processing unit, such as SPU 1305, may include noise reduction, filtering, dampening, combining, amplifying circuitry, etc., for example, implemented to operate in the analog domain. Analog circuitry may include, for example, one or more op-amps, transistors, capacitors, resistors, etc., although subject matter is not limited in scope in this respect. Circuitry, such as noise reduction, filtering, dampening, combining, amplifying circuitry, etc., for example, may also be implemented in the digital domain, or in a combination of analog and/or digital. For another example, a particular sensor processing unit, such as a particular SPU 1305, may be implemented in analog and/or digital to combine signals and/or states. In an embodiment, a unit to combine signals and/or states may be implemented in the analog domain or in the digital domain, or a combination thereof. In an embodiment, analog hysteretic "winner-take-all" circuits may be implemented at least in part to improve noise robustness and/or to mitigate, at least in part, timing difference between sensor input streams, for example. Of course, subject matter is not limited in scope in these respects. Further, noise reduction, filtering, dampening, combining, and/or amplifying are merely example tasks that may be performed by one or more sensor processing units, such as SPUs 1305, and, again, subject matter is not limited in scope in these respects.

Further, in an embodiment, sensor processing units, such as SPU 1305, may be implemented to generate outputs that may exhibit a range of approximation, imprecision, and/or non-replicability. In an embodiment, machine-learning units, such as ML 1306, may help mitigate consequences that might otherwise occur due to approximation, imprecision, and/or non-replicability potentially exhibited by sensor processing units, such as SPU 1305. As utilized herein, "replicable" in the context of sensor processing units, such as SPU 1305, refers to an ability to generate the same output for a given duplicate set of inputs. "Non-replicability" in this context refers to one or more senor processing units, such as SPU 1305, not necessarily generating the same output for a given duplicate set of inputs. That is, in an embodiment, one or more sensor processing units, such as SPU 1305, may be implemented in a manner so as to not guarantee similar outputs for similar sets of inputs.

In an embodiment, content steering circuitry, such as content steering circuitry 1318, may direct content, such as signals and/or states, generated by one or more sensor processing units, such as SPUs 1305, to a machine-learning stage, such as machine-learning stage 1302. Content, such as signals and/or states 1321, generated by one or more sensor processing units, such as SPUs 1305, may also be stored, at least temporarily, in a memory, such as memory 1316, for example. In an embodiment, memory 1316 may comprise a buffer, such as a first-in, first-out buffer, for example, although subject matter is not limited in scope in this respect. In an embodiment, content steering circuitry, such as content steering circuitry 1318, may direct content based, at least in part, on one or more control signals obtained from a control unit, such as control unit 1303, and/or from a memory, such as memory 1312, for example.

A machine-learning stage, such as machine-learning stage 1302, may include content steering circuitry, such as content steering circuitry 1308, that may direct content, such as signals and/or states 1321, obtained from a sensor processing stage, such as sensor processing stage 1301, to one or more machine-learning units (ML), such as machine-learning units 1306, for example. In an embodiment, content steering circuitry, such as content-steering circuitry 1308, may direct content, such as signals and/or states 1321, based, at least in part, on one or more control signals obtained from a control unit, such as control 1303, and/or from a memory, such as memory 1313.

In an embodiment, machine-learning units, such as machine-learning units 1306, may be configured via one or more control signals, such as control signals communicated between a control unit, such as control unit 1303, and machine-learning units, such as machine-learning units 1306. In an embodiment, one or more machine-learning units, such as machine-learning units 1306, may be configured to operate individually or in one combination with one or more other machine-learning units. In an embodiment, individual machine-learning units, such as machine-learning units 1306, may implement particular machine-learning techniques. Further, one or more machine-learning units, such as machine-learning units 1306, may be implemented to operate in the analog domain or in the digital domain, or a combination thereof. For example, a machine-learning unit operating in the analog domain may include voltage and/or current summing circuits to sum a number of signals and/or states and/or may include devices, such as variable impedance devices, that may apply weighting factors to individual signals and/or states. Of course, subject matter is not limited in scope in these respects.

Content steering/selecting circuitry, such as content steering/selecting circuitry 1307, may select and/or combine content generated by one or more machine-learning units, such as machine-learning units 1306, in an embodiment. Further, content steering/selecting circuitry, such as content steering/selecting circuitry 1307, may direct output, such as signals and/or states representative of behavioral profile content 1325, to a decision-making system, such as decision-making system 1340. In an embodiment, a control unit, such as control unit 1303, may obtain at least a portion of the output generated by machine-learning units, such as machine-learning units 1306.

In an embodiment, control unit, such as control unit 1303, may configure and/or control one or more aspects of behavioral processing unit 1300. In an embodiment, a control unit, such as control unit 1303, may obtain inputs from a variety of sources and/or may control various aspects of behavioral processing unit 1300 based, at least in part, on the obtained inputs. In an embodiment, control unit inputs may be obtained from units within behavioral processing unit 1300 unit itself and/or from one or more other sources. For example, control unit 1303 may obtain user parameters 1315 (e.g., user ID or other parameters descriptive of a particular user). In an embodiment, user parameters, such as parameters 1315, may be obtained from an individual and/or from one or more external sources and/or may be obtained from one or more memories within behavioral processing unit 1300. For example, user parameters for one or more particular users may be stored in a memory, such as memory 1304. In an embodiment, one or more parameters, such as parameters 1315, may be obtained, for example, from an intermediary device, such as intermediary device 700. Further, in an embodiment, one or more parameters, such as parameters 1315, may be obtained, for example, from a secure storage device, such as secure storage device 400.

Various aspects of behavioral processing unit 1300 may be configured and/or reconfigured based at least in part on parameters that may be stored on an individual user basis in a memory, such as memory 1304. For example, a control unit, such as control unit 1303, may communicate with a memory, such as memory 1304, to obtain configuration content for a particular user from memory 1304, and/or may configure behavioral processing unit 1300 based at least in part on the obtained configuration content. Further, in an embodiment, a control unit, such as control unit 1303, may obtain content from a decision-making system, such as decision-making system 1340, or from one or more external sources, such as secure storage system 1350. In an embodiment, one or more bio-ledger and/or biosphere entries may be obtained, for example, from a secure storage device, such as secure storage 1350.

Although example behavioral processing unit 1300 is depicted having particular memory devices, such as memories 1304, 1312, 1314, and/or 1316, other embodiments may include memory elements distributed in various areas of the processing unit. For example, memory elements may be included in one or more sensor processing units 1305 and/or in one or more machine-learning units 1306. Additionally, a memory, such as memory 1304, may be implemented as a hierarchy of memory devices and/or technologies that may allow for various sizes and/or memory access speeds. Further, a memory, such as memory 1304, may store machine-learning weighting parameters and/or other machine-learning parameters, and/or may also store control signals, for example.

In an embodiment, a control unit, such as control unit 1303, may generate one or more output signals and/or states, such as one or more control signal, based, at least in part, on inputs obtained by the control unit. Control signal output generation may be a function of one or more inputs that may include, for example, user identification parameters, content type parameters, contextual parameters, task parameters, sensor availability parameters, or behavioral profile content specification parameters, bio-ledger and/or biosphere content, such as content 1311, or any combination thereof. Of course, these are merely example types of inputs that may be obtained by a control unit, such as control unit 1303, and subject matter is not limited in scope to these particular examples.

As mentioned, a control unit, such as control unit 1303, may obtain user parameters 1315 that may include user identification content and/or other parameters descriptive of a particular user). Further, in an embodiment, a control unit, such as control unit 1303, may obtain parameters, such as parameters 1314, descriptive of substances ingested and/or otherwise consumed by a user (e.g., foods, vitamins, medicines, lotions, creams, cosmetics, soaps, shampoo, etc.). Control unit 1303 may further obtain parameters descriptive of a task being performed by a user, or parameters descriptive of context and/or environment, or any combination thereof, for example. Further, in an embodiment, content and/or task parameters 1310 may be provided by and/or obtained from a decision-making system, such as decision-making system 1340. For example, parameters descriptive of user and/or task may indicate a type of task being performed (e.g., walking, flying, driving, performing surgery, etc.) and/or may indicate a particular user. Also, for example, parameters descriptive of context and/or environment may indicate a particular setting (e.g., location, time of day, date, etc.), presence of other individuals, or other contextual information, or any combination thereof.

A control unit, such as control unit 1303, may also obtain parameters, such as parameters 1314, that may be indicative of sensor availability, for example. Additionally, a control unit, such as control unit 1303, may obtain parameters, such as parameters 1319, that may indicate one or more particular parameters and/or parameter types of behavioral profile content, such as behavioral profile content 1325, to be generated on a relative priority basis, for example, by machine-learning stage 1302, for example. Further, one or more parameters 1320 representative of one or more aspects of behavioral profile content 1325 generated by machine-learning stage 1302 may be provided to and/or obtained by a control unit, such as control unit 1303. For example, parameters 1320 may include feedback to control unit 1303 that may influence behavioral processing unit operations, in an embodiment.

As mentioned, a control unit, such as control unit 1303, may generate one or more control signals based, at least in part, on inputs that may be obtained from any of a range of sources. For example, inputs obtained by control unit 1303 may allow for selecting particular content from one or more memory elements, such as one or more of memories 1304, 1312, 1314, and/or 1316, to be utilized in configuring sensor processing stage 1301 and/or machine-learning stage 1302 for processing. For example, sensor processing stage 1301 and/or machine-learning stage 1302 may be configured based on a particular user, a particular task, or a particular context, or a combination thereof. By tailoring processing in this manner, improved behavioral profile content may be generated, and/or efficiency may be improved (e.g., improved confidence of behavioral profile content while utilizing relatively fewer resources). Further, in an embodiment control unit 1303 may steer outputs of sensor processing stage 1301 (e.g., intermediary results) to particular machine-learning units 1305 via control of steering circuitry 1308 based, at least in part, on inputs obtained by control unit 1303. Similarly, control unit 1303 may select output from one or more particular machine-learning units 1306 via control of steering/selecting circuitry 1307 based, at least in part, on obtained inputs. Further, weighting of inputs for machine-learning units 1306 may be determined at least in part based on obtained inputs. For example, a control unit, such as control unit 1303, may steer, select, and/or weight intermediary results (e.g., content generated by sensor processing stage 1301) as a function of user identification, task type, environmental context, or sensor availability, or any combination thereof, in an embodiment. Of course, subject matter is not limited in scope in these respects.

Further, in an embodiment, resource allocation within a processor, such as behavioral processing unit 1300, may be based, at least in part, on behavioral profile content specification parameters, such as parameters 1319. In an embodiment, a control unit, such as control unit 1303, may obtain behavioral profile content specification parameters 1319 that may indicate one or more behavioral profile parameters to be relatively prioritized, for example, and may select particular sensor processing units 1305 and/or particular machine-learning units 1306 based, at least in part, on the specified behavioral profile content parameters. "Relatively prioritized" in the context of behavioral profile content specification parameters, such as parameters 1319, refers to one or more particular parameters to be processed on a priority basis over other parameters. For example, behavioral profile content specification parameters 1319 may indicate an "anger" parameter. Resources (e.g., SPUs 1305, machine-learning units 1306, memory, etc.) sufficient to process the "anger" parameter to a particular confidence level, for example, may be allocated, even at the expense of resources that may otherwise be allocated to generating other behavioral profile content parameters. Control unit 1303 may, via one or more control signals, select resources from sensor processing stage 1301 and/or machine-learning stage 1302 to generate behavioral profile content in accordance with the specified parameters. In this manner, relatively prioritized content may be generated relatively more efficiently. Behavioral profile content specification parameters, such as parameters 1319, may also indicate relative priorities related to trade-offs between power consumption and generation of particular behavioral profile content, in an embodiment. Further, in an embodiment, relatively prioritized content may be generated at the relative expense of other behavioral profile content. For example, behavioral profile parameters indicating anger and/or fatigue may be relatively prioritized over excitement and/or hunger parameters, and control unit 1303 may configure sensor processing stage 1301 and/or machine-learning stage 1302 accordingly. Further, in an embodiment, self-feedback and/or output monitoring content, such as content 1320, may allow for control adjustments, such as selecting additional/different machine-learning units and/or sensor processing units and/or otherwise adjusting resource utilization within behavioral processing unit 1300. Such adjustments may be made, for example, to meet specified relative priorities, specified levels of confidence in generated output, etc.

In addition to allocating resources based, at least in part, on particular parameters related to behavioral profile content processing, other embodiments may allocate resources based, at least in part, on particular bio-ledger and/or biosphere parameters, such as particular parameters from bio-ledger and/or biosphere content 1311, for example.

Although some embodiments described herein mention neural network techniques for machine learning, subject matter is not limited in scope in this respect. Other embodiments may incorporate other machine learning techniques either presently existing or to be developed in the future. Further, for embodiments implementing neural networks, for example, sensors may be removed from a system during offline pre-deployment training operations such that a neural network may determine appropriate weights for various sensor combinations. In another embodiment, during online operation, for example, a set of input biomarkers may be logged and/or later used as training parameters, wherein a predicted behavioral processing unit output may be utilized at least in part to train one or more networks that may lack some subset of the initial inputs. For online inference, an appropriate neural network may be selected based at least in part on available sensor inputs. Such an arrangement may be advantageous in situations wherein an operator may remove one or more sensors from a system, device, and/or process. For example, during surgery, a surgeon may remove his or her glasses that may have been tracking eye movement. In an embodiment, a different neural network configuration may be selected at least in part in response to such a change in available sensor input, for example. For example, a control unit, such as control unit 1303, may detect a change in sensor availability (e.g., signified by sensor availability input 1314), and/or may reconfigure senor processing units 1305 and/or machine-learning units 1306 based at least in part on the detected change in sensor availability.

FIG. 14 is an illustration of an embodiment 1400 of an example process for generating recommendations directed to improvement of a future epigenetic fitness state of a particular individual. Embodiments in accordance with claimed subject matter may include all of blocks 1410-1430, fewer than blocks 1410-1430, and/or more than blocks 1410-1430. Further, the order of blocks 1410-1430 is merely an example order, and subject matter is not limited in scope in these respects. In embodiments, an individual's bio-ledger and/or biosphere ledger content may have value beyond a single lifetime. For example, epigenetic and/or other omic markers may be inherited by future offspring, epigenetic and/or other omic content may be relevant to those with similar health landscapes and/or situations (e.g., family members, relatives, etc.), and/or epigenetic and/or other omic content may be useful for population-level science and/or for future study and/or analysis, to name but a few non-limiting examples. Therefore, benefits of omic and/or behavioral content processing have a potential to span generations. In an embodiment, a potential benefit of epigenetic and/or other omic content processing and/or behavioral content processing may include an ability to measure progress toward "Epigenetic Fitness" goals. For example, a prospective parent may desire to set one or more goals related to epigenetic fitness.

With an increased knowledge of epigenetic, epigenetic inheritance, and/or transgenerational epigenetic inheritance, and/or with decreases in costs of epigenetic testing, individuals may be motivated to change one or more habits to improve their epigenetic state. For example, individuals may desire to improve their intelligence markers and/or to remove addiction markers, not only for themselves, but also for the benefit of future offspring, for example. Similar to the industry around physical fitness, an emergence of "epigenetic fitness" in the general population and/or among prospective parents may occur, particularly since physical fitness and fertility represent relatively very large markets. In an embodiment, an example device, system, and/or process for providing an epigenetic fitness score may allow for an individual to monitor progress toward a particular specified epigenetic fitness goal.

As depicted at block 1410, one or more particular epigenetic parameters determined to be indicative of a particular epigenetic fitness state may be identified. For example, a processor, such as BPU 1200, processor 910, and/or ML 940, may obtain an input from an individual, for example, wherein the input may indicate a particular fitness goal of interest to the individual. That is, in an embodiment, a particular individual may specify a particular goal. For example, an individual may indicate a desire for increased athletic performance abilities. An individual may interact with a user interface of a computing device, such as bio-smart device 900 and/or secure storage device 400, for example, although claimed subject matter is not limited in scope in these respects. Further, as depicted at block 1420, one or more particular omic parameters for a particular individual may be compared with the identified one or more particular epigenetic parameters determined to be indicative of a particular fitness goal. In an embodiment, the comparison may be performed, for example, by a processor, such as BPU 1200, processor 910, and/or ML 940. For example, a subset of epigenetic markers having a determined and/or known relationship to the individual's specified goal (e.g., epigenetic markers associated with athletic performance), may be extracted and/or otherwise obtained from the individual's bio-ledger. For example, a computing device, such a bio-smart device 900, may receive signal packets and/or signal frames comprising bio-ledger content, for example, over a network from a secure storage device, such as secure storage device 400. Further, in an embodiment, the individual's epigenetic markers may be compared to the desired markers based at least in part on the specified goal. Again, for example, a processor, such as BPU 1200, processor 910, and/or ML 940, may perform the comparison. In an embodiment, a score may be generated by a processor, such as BPU 1200, processor 910, and/or ML 940, based, at least in part, on a measure of similarity between the individual's particular markers and the desired markers. In an embodiment, a determination of a measure of similarity may be based, at least in part, on any of a number of possible distance metrics. Various parameters and/or markers may be weighted based, at least in part, on a determined importance factor for a particular marker, in an embodiment.

In an embodiment, as indicated at block 1430, one or more recommendations for a particular individual may be generated based, at least in part, on a comparison of the individual's markers and the desired markers, and/or based at least in part on one or more behavioral profile parameters, or a combination thereof, wherein one or more recommendations are substantially directed to improvement of a future epigenetic fitness state of the particular individual. For example, in an embodiment, an individual's biosphere ledger may be analyzed by a processor, such as BPU 1200, processor 910, and/or ML 940, to provide recommendations for influencing desired markers. In an embodiment, analyzation of an individual's biosphere ledger may be based, at least in part, on machine learning-identified relationships via population science. Further, in an embodiment, this example process may continue at specified intervals to provide an individual with updated epigenetic fitness scores and/or with updated recommendations.

In some situations, progress towards health and/or fitness goals for individuals may be measured according, at least in part, to relatively inferior metrics such as weight, body-mass index, exercise time, and so forth. Embodiments described herein introduce utilization of epigenetic markers to monitor progress towards fitness and/or health goals. Further, embodiments may provide relatively more refined metrics that may provide improved accuracy with respect to progress, as well as provide content regarding health predispositions that may be passed on to future offspring.

Figure 15A:
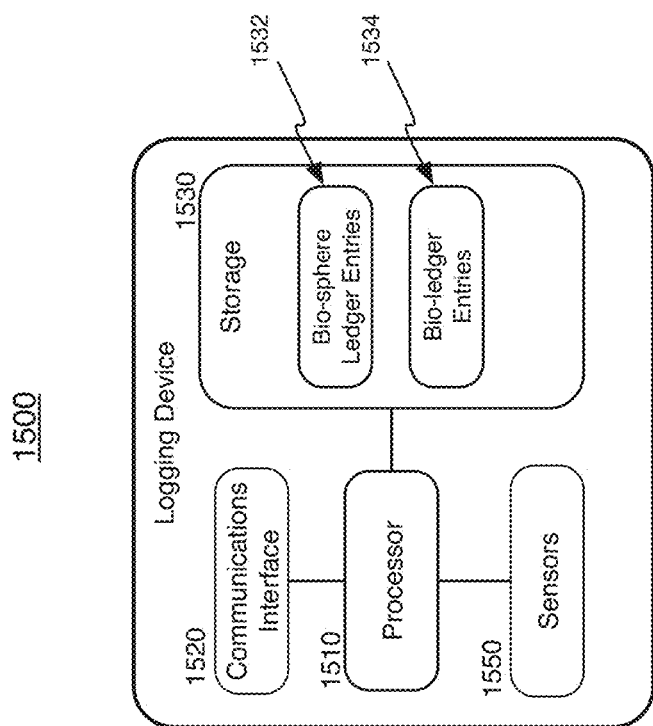
FIG. 15a is an illustration of an example logging-type device, in accordance with an embodiment.

FIG. 15a is an illustration of an embodiment 1500 of an example logging-type device. As mentioned, devices may comprise a "logging" type device, wherein particular content may be logged to one or more particular individual's biosphere ledger and/or bio-ledger. As mentioned, a public logging-type device may log biosphere and/or bio-ledger content intended to be shared across a population of individuals, in an embodiment. On the other hand, a private logging device may log bio-ledger and/or biosphere entries pertaining to a particular individual. In an embodiment, a logging-type device, such as logging-type device 1500, may include one or more sensors, such as sensors 1550, that may log measurements pertaining to one or more particular individuals to a memory, such as memory 1530. A memory, such as memory 1530, may store, for example, bio-ledger entries 1534 and/or biosphere entries 1532.

In an embodiment, logging of content to a particular individual's biosphere ledger and/or bio-ledger may occur at least in part in response to an individual, such as user 310, coming into proximity of the logging-type device and/or at least in part in response to an intermediary device, such as intermediary device 700, being electrically connected to a logging-type device, such as logging-type device 1500. For example, an individual, such as user 310, may carry an intermediary device, such as intermediary device 700, within a specified distance of a logging-type device, such as logging-type device 1500. Also, in an embodiment, a logging-type device, such as logging-type device 1500, may identify a particular intermediary device and/or a particular individual based, at least in part, on one or more wireless signals communicated between an intermediary device, such as intermediary device 700, and a logging-type device, such as logging-type device 1500.

Figure 15B:
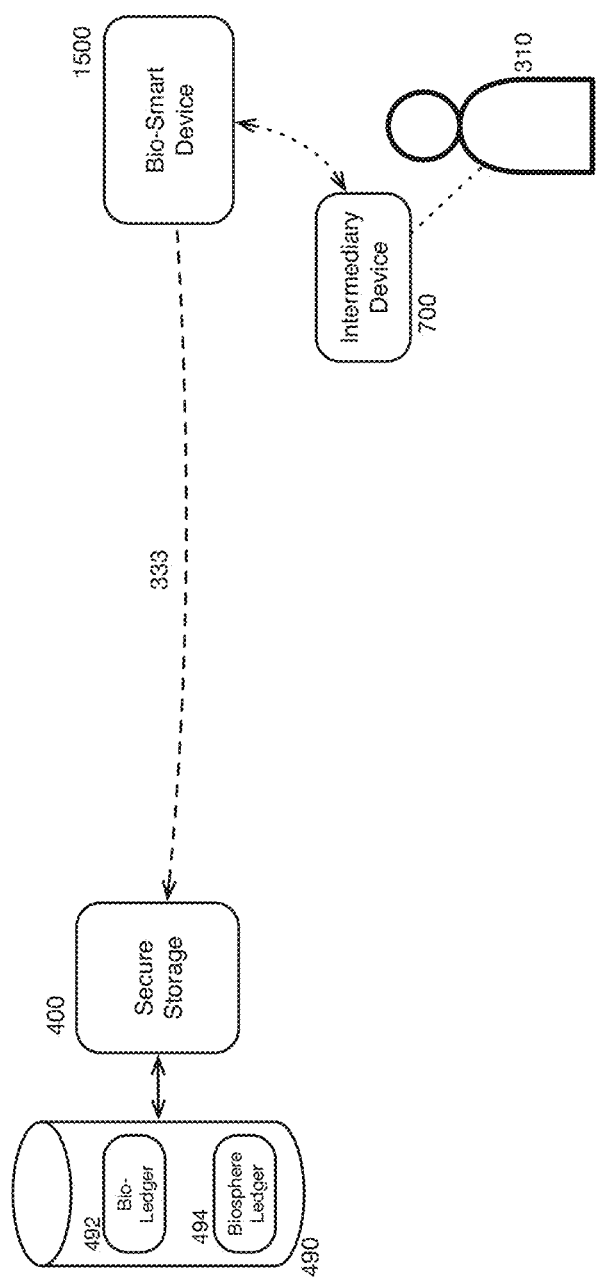
FIG. 15b is an illustration of an example communication of epigenetic content between a logging-type device and a storage device, in accordance with an embodiment.

FIG. 15b depicts an example communication of bio-ledger and/or biosphere ledger content. In an embodiment, bio-ledger content, such as entries 1534, and/or biosphere ledger content, such as entries 1532, may be communicated between a logging-type device, such as logging-type device 1500, and any of a wide range of devices, systems, and/or processes. For example, content, such as content 333 including one or more bio-ledger entries 1534 and/or one or more biosphere entries 1532, may be communicated via one or more wired and/or wireless communication networks between a computing device, such as logging-type device 1500, and one or more other devices, such as secure storage device 400 and/or intermediary device 700. In an embodiment, a logging-type device, such as device 1500, may include a communications interface, such as communication interface 1520, and may further include a processor, such as processor 1510. In an embodiment, logged entries, such as entries 1532 and/or 1534, may be communicated via utilization of a processor, such as processor 1510, and/or a communication interface, such as communication interface 1520. Of course, subject matter is not limited in scope in these respects.

In further embodiments, a logging-type device, such as logging-type device 1500, may comprise an industrial-scale logging-type device. As mentioned, industrial-scale logging-type devices may process epigenetic and/or other omic content, behavioral profile content, and/or environmental content related to multiple particular individuals, and/or may access/write to bio-ledgers and/or biosphere ledgers pertaining to multiple particular individuals, for example.

Figure 16:
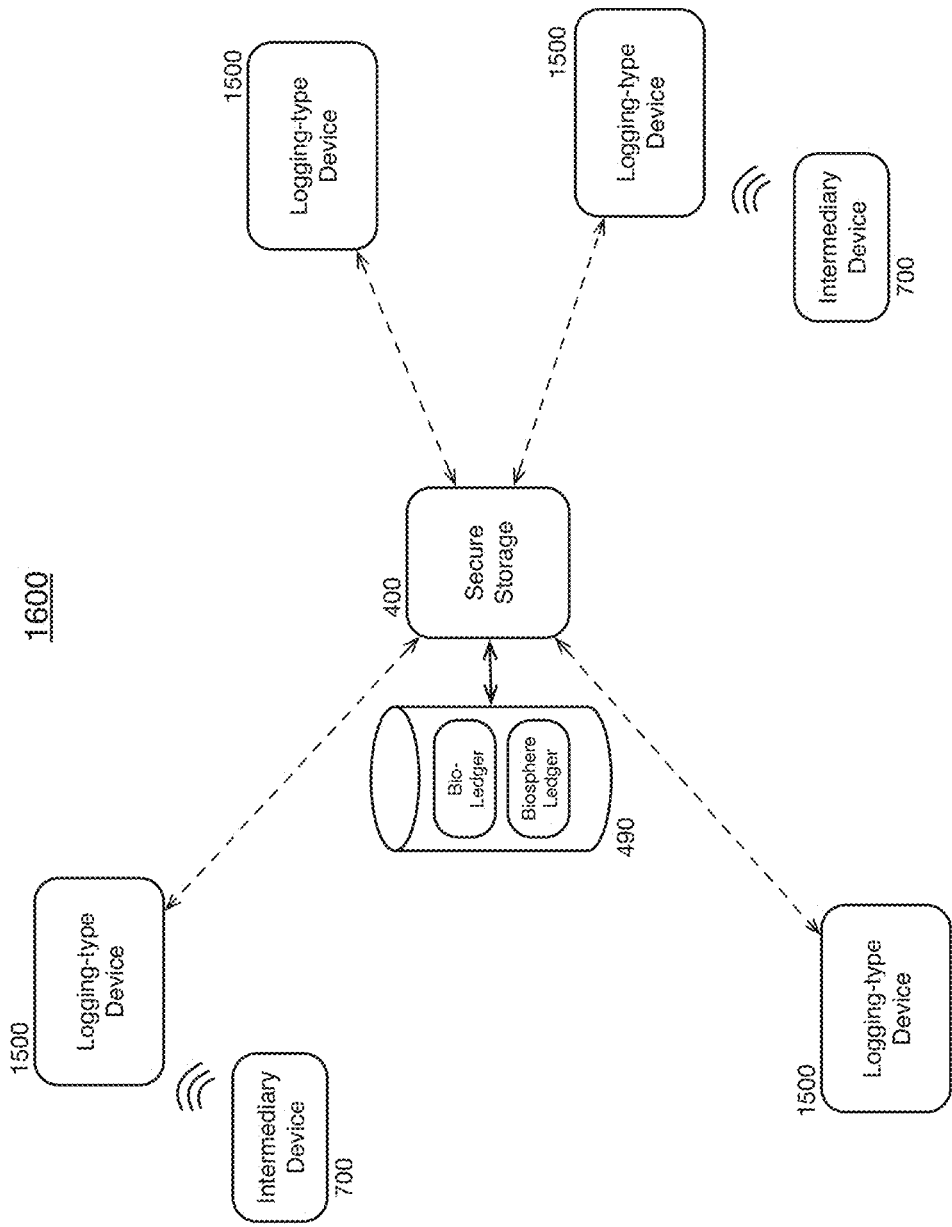
FIG. 16 is an illustration of an example device, system, and/or process for processing signals and/or states representative of epigenetic content, in accordance with an embodiment.

FIG. 16, for example, is an illustration of an embodiment 1600 of an example system for processing signals and/or states representative of epigenetic and/or other omic content across a population of individuals. In an embodiment, a system, such as example system 1600, may include a plurality of logging-type devices, such as logging-type devices 1500, for example. In an embodiment, logging-type devices, such as logging-type devices 1500, may communicate via wired and/or wireless network signals with a storage device, such as secure storage 400. For example, one or more logging-type devices, such as logging-type devices 1500, may transfer one or more parameters indicative of bio-ledger and/or biosphere content for one or more particular individuals from logging-type devices 1500 to secure storage device 400. For example, logging-type devices 1500 may write bio-ledger content and/or biosphere content for one or more individuals to storage 490, in an embodiment. In another embodiment, biosphere ledger entries, for example, may not pertain to particular individuals but may instead pertain across a population of individuals. In an embodiment, a storage device, such as secure storage device 400, may store copies of public and/or general biosphere ledger entries in particular biosphere ledgers for particular individuals based at least in part on the particular individual's GPS location content, for example. In an embodiment, a logging-type device, such as logging-type device 1500, may store an identifier for intermediary devices detected to have come within a particular proximity of the logging-type device, for example. Based at least in part on the stored identifiers, a logging-type device, such as logging-type device 1500, for example, may facilitate communication of appropriate biosphere ledger entries from a logging-type device, such as logging-type device 1500, and a secure storage device, such as secure storage device 400, such that a secure storage device, such as secure storage device 400, may store the appropriate biosphere ledger entries in appropriate individuals' biosphere ledgers, in an embodiment.

In an embodiment, one or more individuals, such as user 310, may carry and/or wear, for example, one or more respective intermediary devices, such as intermediary devices 700. One or more intermediary devices 700 may come into proximity with one or more logging-type bio-smart devices, such as bio-smart devices 1500. At least in part in response to a detection of one or more intermediary devices 700, one or more logging-type bio-smart devices 1500 may store one or more measurements, for example, in an onboard memory, such as memory 1530. Further, in an embodiment, one or more logging-type bio-smart devices 1500 may initiate communication of one or more measurements, for example, between the one or more bio-smart devices 1500 and secure storage 400 so that measurement content may be stored in database 490. Further, as intermediary devices 700 are transported around a geographical area, for example, multiple logging-type devices may be encountered, and/or multiple measurement parameters may be communicated and/or stored. Over a period of time, for example, a number of measurements for a number of individuals may be gathered and/or may be stored, for example, at a secure storage device, such as secure storage device 400. Further, particular changes to epigenetic and/or other omic markers for particular individuals may be detected, and/or patterns involving larger numbers of individuals may be detected, at least in part via a processor, such as processor 410 of secure storage device 400, in an embodiment.

Figure 17:
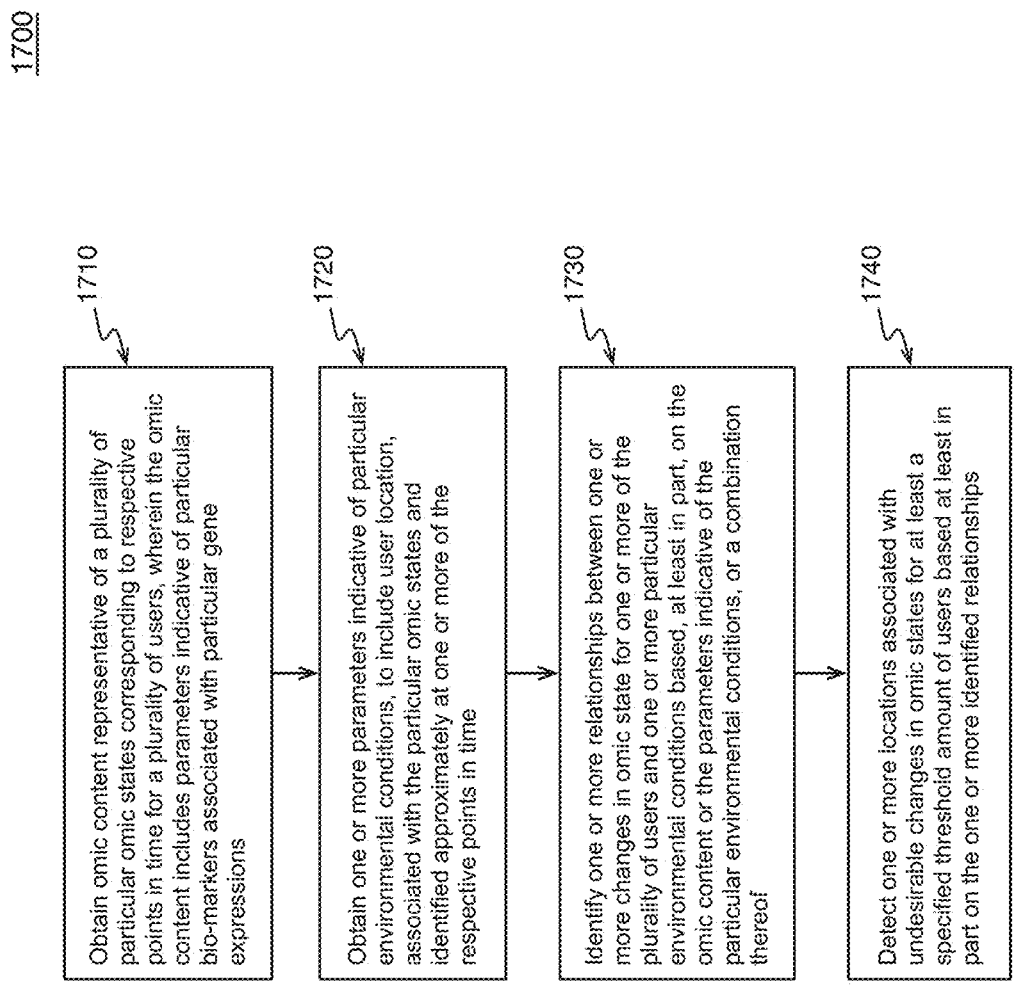
FIG. 17 is an illustration of an example process for detecting locations associated with undesirable changes in epigenetic state, in accordance with an embodiment.

FIG. 17 is an illustration of an embodiment 1700 of an example process for detecting locations associated with undesirable changes in epigenetic state. Embodiments in accordance with claimed subject matter may include all of blocks 1710-1740, fewer than blocks 1710-1740, and/or more than blocks 1710-1740. Further, the order of blocks 1710-1740 is merely an example order, and subject matter is not limited in scope in these respects.

Devices, systems, and/or processes, such as bio-smart devices 900 and/or other types of devices, may be utilized, in an embodiment, to monitor, track, and/or otherwise gather bio-ledger and/or biosphere ledger content across a population of individuals. In an embodiment, location parameters associated with biosphere ledger entries, for example, may be utilized in conjunction, at least in part, with bio-ledger content over a group of individuals to identify and/or predict geographically-significant events. For example, trends in changes to epigenetic state for a plurality of individuals may be tracked within a particular geographical area. In an embodiment, content representative of changes in epigenetic state for particular individuals within a population (e.g., bio-ledger content) may be correlated and/or otherwise associated with particular content identifying particular locations within a geographical area (e.g., biosphere ledger content) to detect and/or predict geo-graphically significant events. By linking relatively fine-grained location parameters to epigenetic content, example devices, systems, and/or processes may identify and/or predict societally-significant events such as, for example, an introduction of environmental toxins (e.g., lead contamination, air pollutants, etc.), an introduction of food supply contaminations (e.g., via identification of early-onset puberty), and/or an increase in addiction rates (e.g., opioid over-distribution). Of course, these are merely examples, and subject matter is not limited in scope in these respects.

Herein, a particular location determined to be associated with a trend and/or pattern of adverse changes in epigenetic state over a population of individuals may be referred to as a "geographic hotspot." In an embodiment, bio-smart devices, such as bio-smart device 900, may be utilized, at least in part, to determine geographic hotspots. For example, machine-learning, such as ML 940 and/or BPU 1200 and/or BPU 1300, may be utilized to identify, at least in part, a trend and/or pattern of changes in epigenetic state for individuals of a population of individuals, wherein the trend and/or pattern of changes in epigenetic state are associated with one or more particular locations within a geographical area. However, although some embodiments may utilize bio-smart devices, such as bio-smart device 900, and/or behavioral processing units, such as BPUs 1200 and/or 1300, to identify geographical hotspots, other embodiments may utilize, at least in part, other types of electronic devices. In some embodiments, machine-learning, such as performed by ML 940, BPU 1200, and/or BPU 1300, for example, may be utilized, at least in part, to identify geographic hotspots. However, in other embodiments, other types of processing and/or analysis may be utilized, at least in part, to identify geographical hotspots.

In general, to identify epigenetic geographic hotspots, a computing device, such as secure storage device 400 and/or bio-smart device 900, may attach relatively fine-grained location parameters to an individual's omic content (e.g., epigenetic test content, environmental influencer content, etc.) at least in part by accessing an individual's bio-ledger and/or biosphere ledger. In an embodiment, a bio-smart device, such as bio-smart device 900, may read from and/or write to an individual's bio-ledger and/or biosphere ledger at least in part via wired and/or wireless communication of signal packets and/or signal frames over a network. In an embodiment, location parameters may represent locations which an individual may have visited and/or at which an individual may have resided, for example. In an embodiment, location parameters may be based, at least in part, on satellite positioning system location content (e.g., GPS location content). In an embodiment, attaching and/or otherwise associating location parameters to epigenetic content may be performed by a processor, such as processor 410, for a number of individuals across a population of individuals. Further, in general, trends in epigenetic and/or other omic state changes across individuals of a population may be monitored. In an embodiment, individuals of a population may be related according to location. That is, for example, individuals located, either temporarily and/or more regularly, in a particular geographic region may be considered a population of individuals, in an embodiment. Additionally, in general, prior knowledge regarding epigenetic markers (e.g., epigenetic markers associated with addiction, environmental toxins, etc.) and their relationships to health may be utilized to identify societally-relevant phenomena occurring in a geographic region. In an embodiment, such prior knowledge may be gleaned, at least in part, from bio-ledger and/or biosphere ledger content for a number of individuals. In an embodiment, geographic hotspots may be determined for one or more particular locations (e.g., particular factory, restaurant, park, home, office, etc.). In other embodiments, geographic hotspots may be determined for a location representative of a geographic area (e.g., particular neighborhood, city, county, etc.). Of course, subject matter is not limited in scope in these respects.

Returning to FIG. 17, an embodiment 1700 of an example process for detecting geographical hotspots is illustrated. As depicted at block 1710, omic content representative of a plurality of particular epigenetic states corresponding to respective points in time for a plurality of individuals may be obtained, wherein the omic content includes parameters indicative of particular bio-markers associated with particular gene expressions. In an embodiment, omic and/or epigenetic content may be obtained by a secure storage device, such as secure storage device 400, at least in part by receiving, at communications interface 420, signal packets and/or signal frames, for example, transmitted over a network, such as the Internet. In an embodiment, epigenetic and/or other omic content may be obtained at least in part by receiving signal packets and/or signal frames from test lab computing devices, doctor office computing devices, etc. In an embodiment, omic and/or other epigenetic content may be stored as one or more bio-ledger entries and/or one or more biosphere entries, for example. In an embodiment, bio-ledger entries and/or biosphere entries may be stored, for example, as signals and/or states in one or more non-transitory media and/or memories and/or mass storage devices of a secure storage device, such as secure storage device 400. Further, as indicated at block 1720, one or more parameters indicative of particular environmental conditions, including user location, associated with the particular omic states and identified approximately at one or more of the respective points in time may also be obtained. In an embodiment, omic and/or epigenetic content may be obtained by a secure storage device, one or more parameters indicative of particular environmental conditions, including user location, associated with the particular omic states may be obtained, at least in part by receiving, at communications interface 420, for example, signal packets and/or signal frames transmitted over a network, such as the Internet.

Further, in an embodiment, as indicated at block 1730, one or more relationships between one or more changes in epigenetic state for one or more of the plurality of individuals and one or more particular environmental conditions may be identified utilizing a processor, such as BPU 1200, processor 910, and/or ML 940, based, at least in part, on the epigenetic content or the parameters indicative of the particular environmental conditions, or a combination thereof. Also, in an embodiment, one or more locations associated with undesirable changes in epigenetic states for at least a specified threshold number of individuals may be detected based at least in part on the one or more identified relationships, as performed at least in part by a processor, such as BPU 1200, processor 910, and/or ML 940.

In some situations, problems such as environmental toxins may be discovered to occur, for example, based on sufficient numbers of people becoming ill, exhibiting symptoms, seeking help, etc. Embodiments described herein may be advantageously utilized to identify location-based trends relatively more quickly. Further, embodiments may allow for identification of trends that may ordinarily go unnoticed by an individual (e.g., early-onset puberty, inability to concentrate in children, etc.). Further, embodiments wherein location parameters may be associated and/or otherwise linked with epigenetic content may allow for relatively more directed and/or efficient allocation of resources aimed at addressing societally-relevant issues related to a geographic region. For example, a problem of resource allocation for addiction and/or suicide prevention may be addressed, in an embodiment. Also, for example, embodiments may support identification of geographical regions having increasing addiction rates, thereby allowing for relatively more accurate identification of regions for increased resource allocation. Again, subject matter is not limited in scope in these respects.

Figure 18:
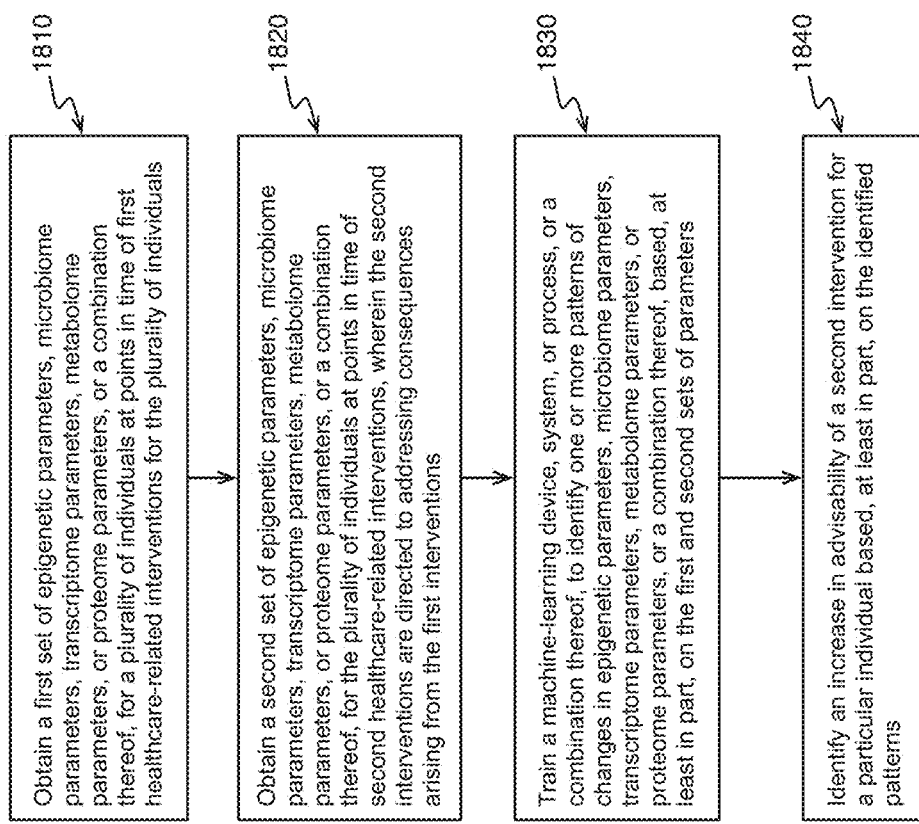
FIG. 18 is an illustration of an example process for identifying patterns of changes in epigenetic, microbiome, and/or proteome parameters, in accordance with an embodiment.

FIG. 18 is an illustration of an example process for identifying patterns of proteome changes, microbiome changes, metabolome, transcriptome, and/or epigenetic changes that may lead to adverse iatrogenic consequences. As utilized herein, "proteome" refers to a set of proteins expressed by a genome, cell, tissue, and/or organism at a particular point in time. "Proteome content" and/or the like refers to digital content, such as signals and/or states, representative of one or more aspects of proteome. Further, "microbiome" refers to combined genetic material of a community. In humans, for example, microbiome refers to genes of microbes that may exist within a particular individual. "Microbiome content" and/or the like refers to content, such as signals and/or states, representative of one or more aspects of microbiome. "Transcriptome" refers to a set of messenger RNA molecules expressed from the genes of an organism and/or "metabolome" refers to a set of metabolites present within an organism, for example. Additionally, "iatrogenic" relates to illness caused, at least in part, by medical examination and/or treatment.

In general, for an embodiment, content, such as proteome, microbiome, metabolome, transcriptome, and/or epigenetic content, may be collected and/or otherwise obtained at a point of an initial healthcare-related intervention and again at a point of a secondary point of healthcare-related intervention wherein the secondary intervention was directed at addressing a negative consequence of the prior intervention. Machine learning and/or other analysis techniques may be utilized to identify patterns of epigenetic and/or microbiome changes associated with adverse and/or negative iatrogenic consequences. Examples of initial healthcare-related interventions may include, but are not limited to, dental implantation, newly administered medication within a psychiatric and/or medical situation, and/or recommendation of a particular behavioral regiment, such as an elite athletic training routine. Again, subject matter is not limited in scope in these respects.

In some situations, some patients may suffer from negative and/or occasionally irreversible effects that may manifest over time due to an interaction with a healthcare provider. Iatrogenic effects such as these may be of particular concern to healthcare providers. For example, healthcare providers may wish to avoid situations where second interventions may be needed to address negative consequences of an earlier intervention. By collecting proteome, microbiome, metabolome, transcriptome, and/or epigenetic content at the point of and/or substantially immediately prior to an initial intervention and again at a point of secondary intervention, for example, machine learning and/or other analysis techniques may be utilized, at least in part, to identify a pattern of epigenetic and/or other omic changes associated with an advisability for a secondary intervention. Once trained, a machine-learning device, system, and/or process, for example, may signal to a healthcare professional, for example, that a secondary intervention may be advisable in a for a particular individual based at least in part on an identification of similar patterns in changes to epigenetic, microbiome, and/or proteome content. In an embodiment, proteome, microbiome, metabolome, transcriptome, and/or epigenetic content may be stored as bio-ledger entries, for example.

Embodiments may provide any of several example advantages, including a potential to identify a situation before a damaging consequence may occur, a possibility of identification a situation without additional healthcare professional invention (e.g. via mail-in epigenetic testing) in situations wherein a subsequent intervention may be beneficial, and/or a possibility of identification without reliance on subjective (e.g., patient-reported) content. In many situations, doctors, for example, may manage responsibility for iatrogenic consequences through follow-up visits in which subjective patient reporting of undesirable consequences and/or diagnostic testing, such as blood testing, provides content related to an advisability for a secondary intervention. Additional situations may arise wherein iatrogenic consequences may not be actively managed. In such situations, for example, handling of iatrogenic responsibilities via subjective reporting and/or other diagnostic tests may lead to an undesirable situation of identifying advisability for secondary intervention after, rather than prior, to an onset of undesirable consequences. Additionally, additional proteome, microbiome, metabolome, transcriptome, and/or epigenetic testing between a first intervention and a second intervention may allow for tracking a more detailed progression of changes which may lead to even earlier identification of an advisability for a secondary intervention.

In embodiments, epigenetic testing, for example, may present an opportunity to track additional patient-related content due at least in part to epigenetic changes having been shown to occur at least in part in response to changes in environment, including environmental changes due to healthcare provider intervention. In some situations, however, the sheer number of possibilities related to such changes may limit identification of particular epigenetic patterns to well-researched disease states. Embodiments, such as one or more of those described herein, may provide an opportunity to monitor an individual's body's reaction to environmental changes associated with a healthcare-related intervention, and/or to identify a desirability for a secondary intervention prior to onset of negative and/or otherwise undesirable consequences.

Returning to FIG. 18, an embodiment 1800 of an example process for identifying patterns of proteome changes, microbiome changes, metabolome changes, transcriptome changes, and/or epigenetic changes that may lead to adverse iatrogenic consequences is depicted. Embodiments in accordance with claimed subject matter may include all of blocks 1810-1840, fewer than blocks 1810-1840, and/or more than blocks 1810-1840. Further, the order of blocks 1810-1840 is merely an example order, and subject matter is not limited in scope in these respects. As depicted at block 1810, a first set of epigenetic parameters, microbiome parameters, metabolome, transcriptome, or proteome parameters, or a combination thereof, may be obtained for a plurality of individuals at points in time of first healthcare-related interventions for the plurality of individuals. For example, omic test results for a plurality of individuals may be stored as signals and/or states in a database, such as a bio-ledger and/or biosphere ledger, for one or more individuals at a secure storage device, such as secure storage device 400. Additionally, as indicated at block 1820, a second set of epigenetic parameters, microbiome parameters, or proteome parameters, or a combination thereof, may be obtained for a plurality of individuals at points in time of second healthcare-related interventions, wherein the second interventions may be directed to addressing consequences arising from first interventions. Again, in an embodiment, omic test results for a plurality of individuals may be stored as signals and/or states in a database, such as a bio-ledger and/or biosphere ledger, for one or more individuals at a secure storage device, such as secure storage device 400.

In an embodiment, a machine-learning device, system, or process, or a combination thereof, such a processor 410, BPU 1200, BPU 1300, and/or ML 940, for example, may be trained to identify one or more patterns of changes in epigenetic parameters, microbiome parameters, metabolome parameters, transcriptome parameters, or proteome parameters, or a combination thereof, based, at least in part, on the first and second sets of parameters, as indicated at block 1830. Further, as indicated at block 1840, an increase in advisability and/or need of a second intervention for a particular individual may be identified based, at least in part, on the identified patterns. In an embodiment, identification of an increase in advisability of a second intervention may be performed, at least in part, by processor, such as BPU 1200, processor 910, and/or ML 940. As mentioned, by identifying situations in which a second intervention may be advisable, a healthcare professional may take steps to either avoid situations that tend to lead to second interventions, and/or may more quickly take steps to reduce negative and/or otherwise adverse consequences arising from a prior intervention.

Below, various example embodiment are reviewed. As noted, claimed subject matter is not limited in scope to these specific examples. As described herein, embodiments may include obtaining epigenetic content for a particular individual, wherein the epigenetic content is representative of a plurality of particular epigenetic states corresponding to respective points in time. Embodiments may further include tracking behavioral profile content for the particular individual over a period of time including the respective points in time, training a machine-learning device, system, or process, or a combination thereof, to identify one or more relationships between one or more particular behaviors and one or more changes in epigenetic state for the particular individual based, at least in part, on the epigenetic content and the behavioral profile content, and identifying a further change in epigenetic state for the particular individual based at least in part on a detected change in behavioral profile content.

In an embodiment, epigenetic content representative of a plurality of particular epigenetic states for a particular individual may include one or more entries from a bio-ledger for the particular individual, wherein the bio-ledger includes one or more parameters indicative of particular bio-markers associated with particular gene expression. Epigenetic content representative of the plurality of particular epigenetic states for a particular individual may also include one or more entries from a biosphere ledger for the particular individual, wherein the biosphere ledger includes one or more parameters indicative or particular environmental conditions identified approximately at one or more of the respective points in time.

In an embodiment, an apparatus may include at least one processor to obtain signals and/or states representative of behavioral profile content for a particular individual, the behavioral profile content to include a plurality of parameters representative of a current behavioral state or biological state, or a combination thereof, of the particular individual. In an embodiment, at least one processor may further obtain signals and/or states representative of epigenetic content for a particular individual, and/or may, at least in part via one or more machine learning operations, generate one or more recommendations for the particular individual based at least in part on the behavioral profile content or based at least in part on the epigenetic content, or a combination thereof. In an embodiment, the one or more recommendations may be directed to improvement of a future epigenetic state of the particular individual.

In an embodiment, epigenetic content for a particular individual may include one or more parameters representative of one or more particular epigenetic states to correspond to one or more particular points in time. Further, one or more parameters representative of the plurality of particular epigenetic states may include one or more entries from a bio-ledger for the particular individual, wherein the bio-ledger may include one or more parameters indicative of particular bio-markers associated with particular gene expressions. Also, in an embodiment, at least one processor may initiate communication of the epigenetic content for the particular individual between a server computing device and the at least one processor at least in part via an exchange of one or more security tokens. Further, at least one processor may obtain one or more security tokens from a portable electronic device of the particular individual.

In other embodiments, an apparatus may include at least one processor to obtain signals and/or states representative of epigenetic content for one or more individuals, wherein the epigenetic content to include one or more parameters indicative of particular bio-markers associated with particular gene expressions. An apparatus may also include at least one memory to store the epigenetic content for the one or more individuals, wherein the epigenetic content to be indexed at least in part on a per-user basis. In an embodiment, at least one processor may obtain signals and/or states representative of environmental factor content associated with epigenetic content, wherein at least one memory further to store the environmental factor content, and wherein the environmental factor content to be indexed at least in part on a per-user basis. Also, in an embodiment, at least one processor may initiate transmission of a particular security token to a portable computing device of a particular individual to allow for access to one or more entries of epigenetic content associated with the particular individual. Additionally, the at least one processor to initiate transmission of one or more decryption keys to a portable computing device of a particular individual to allow for decryption of the one or more entries of epigenetic content associated with the particular individual.

In an embodiment, an apparatus may further include an external device port, wherein at least one processor to initiate transmission of one or more security tokens at least in part in response to a physical attachment of the portable computing device to the external device port. At least one processor may further initiate transmission of a specified subset of epigenetic content associated with the particular individual to a networked device at least in part in response to a request from the networked device, wherein the request to include the particular security token.

In a further embodiment, an apparatus may include at least one processor to obtain a security token from a server computing device, wherein the security token to provide particular permission to access one or more particular entries of epigenetic content associated with a particular individual stored at the server computing device. An apparatus may also include at least one memory to store the security token, and at least one sensor to detect proximity to a particular external device, wherein the at least one processor to initiate transmission of the security token to the external device at least in part in response to the detection of proximity. Further, in an embodiment, at least one processor may obtain one or more particular entries of epigenetic content from the server computing device, and the at least one memory may store the one or more particular entries. Also, at least one processor may initiate transmission of at least a subset of the one or more entries to the external device at least in part in response to the detection of proximity. In an embodiment, at least one sensor may include a local wireless network transceiver, and at least one processor may initiate transmission of the security token via the local wireless network transceiver.

An additional embodiment may include identifying one or more particular epigenetic parameters determined to be indicative of a particular fitness state, storing signals and/or states representative of the identified one or more particular epigenetic parameters in at least one memory, comparing, utilizing at least one processor, one or more particular epigenetic parameters for a particular individual with the identified one or more particular epigenetic parameters determined to be indicative of a particular fitness goal, and generating, via the at least one processor based at least in part on one or more machine learning operations, one or more recommendations for the particular individual based at least in part on the comparing or based at least in part on one or more behavioral profile parameters, or a combination thereof, wherein the one or more recommendations are substantially directed to improvement of a future epigenetic fitness state of the particular individual.

Further, embodiments may include obtaining, utilizing at least one processor, epigenetic content representative of a plurality of particular epigenetic states corresponding to respective points in time for a plurality of individuals, wherein the epigenetic content to include parameters indicative of particular bio-markers associated with particular gene expressions, obtaining, utilizing the at least one processor, one or more parameters indicative of particular environmental conditions, including user location, associated with the particular epigenetic states and identified approximately at one or more of the respective points in time, storing the epigenetic content or the parameters indicative of the particular environmental conditions, or a combination thereof, in at least one memory, identifying, via a machine-learning device and/or system, one or more relationships between one or more changes in epigenetic state for one or more of the plurality of individuals and one or more particular environmental conditions based, at least in part, on the epigenetic content or the parameters indicative of the particular environmental conditions, or a combination thereof, and detecting, at least in part via the machine-learning device and/or system, one or more locations associated with undesirable changes in epigenetic states for at least a specified threshold amount of individuals based at least in part on the one or more identified relationships. Embodiments may also include generating, via the machine-learning device and/or system, one or more recommendations based at least in part on the one or more identified relationships, wherein the one or more recommendations are directed to improvement of future epigenetic states of at least the plurality of individuals.

An additional embodiment may include obtaining, utilizing at least one processor, a first set of epigenetic parameters, microbiome parameters, or proteome parameters, or a combination thereof, for a plurality of individuals at points in time of first healthcare-related interventions for the plurality of individuals, storing the first set of parameters in at least one memory, obtaining, utilizing at least one processor, a second set of epigenetic parameters, microbiome parameters, metabolome parameters, transcriptome parameters, or proteome parameters, or a combination thereof, for the plurality of individuals at points in time of second healthcare-related interventions, wherein the second interventions are directed to addressing consequences arising from the first interventions, storing the second set of parameters in at least one memory, training a machine-learning device, system, or process, or a combination thereof, to identify one or more patterns of changes in epigenetic parameters, microbiome parameters, metabolome parameters, transcriptome parameters, or proteome parameters, or a combination thereof, based, at least in part, on the first and second sets of parameters, and identifying an increase in advisability and/or need for a second intervention for a particular individual based, at least in part, on the identified patterns.

An embodiment may also include obtaining one or more additional epigenetic parameters, microbiome parameters, or proteome parameters, or a combination thereof, for the particular individual, wherein the identifying the increase in likelihood of the second intervention is based, at least in part, on the identified patterns and on the additional parameters.

Embodiments may also be employed in agricultural situations. For example, an embodiment may include obtaining epigenetic content representative of a plurality of particular epigenetic states corresponding to respective points in time for a particular crop, obtaining from at least one sensor behavioral content for the particular crop over a period of time including the respective points in time, training a machine-learning device, system, or process, or a combination thereof, to identify one or more relationships between one or more particular behaviors and one or more changes in epigenetic state for the particular crop based, at least in part, on the epigenetic content and the behavioral content, and predicting a further change in epigenetic state for the particular crop based at least in part on a detected change in behavioral content. An embodiment may further include generating, at least in part via the machine-learning device, system, or process, one or more recommendations with respect to time to harvest, time to fertilize, or time to shade, or a combination thereof, for the particular crop based, at least in part, on the predicted change in epigenetic state.

In a further embodiment, an apparatus may include a weight scale to detect weight of a user, and/or may include at least one memory to store parameters indicative of user weight measured at particular points in time. In an embodiment, at least one processor may obtain signals and/or states representative of epigenetic content for a particular user, and may, at least in part via one or more machine learning operations, generate one or more recommendations for the particular user based at least in part on the user weight parameters or based at least in part on the epigenetic content, or a combination thereof, the one or more recommendations to be directed to improvement of a future epigenetic state of the particular user. In an embodiment, at least one processor may further obtain content representative of one or more aspects of one or more scientific publications directed to relationships between particular epigenetic parameters and weight changes, wherein at least one processor may generate the recommendations based, at least in part, on the user weight parameters, the epigenetic content, or the content representative of the one or more aspects of one or more scientific publications, or a combination thereof. In an embodiment, one or more recommendations may include one or more recommendations to avoid a pre-diabetes condition, and/or may include one or more recommendations to avoid potential adverse effects to future offspring.

One or more other embodiments may include one or more sensors to detect proximity of a plurality of uniquely identified personal computing devices, the one or more sensors further to detect one or more particular environmental conditions at one or more particular points in time, and/or may include at least one memory to store one or more parameters representative of the one or more particular environmental conditions at the one or more particular points in time, to store parameters indicative of identities of the plurality of uniquely identified personal computing devices to be detected, and to store time stamp content to indicate times of detection for respective personal computing devices. In an embodiment, at least one processor may initiate transmission of the one or more parameters representative of one or more particular environmental conditions, parameters indicative of identities of the plurality of uniquely identified personal computing devices, and/or the time stamp content to a biosphere ledger database to comprise a networked computing device. In another embodiment, a logging-type device, for example, may log on to an individual's intermediary device at least in part to link a generalized biosphere ledger entry to a particular individual's biosphere ledger, for example. In some embodiments, a logging-type device may transfer a generalize biosphere ledger entry to a particular individual's intermediary device, and/or the intermediary device may be utilized, for example, to transfer biosphere ledger entry content to a secure storage device.

In an embodiment, one or more sensors may include a wireless network receiver to detect the proximity of the plurality of uniquely identified personal computing devices. One or more sensors may also include, for example, an air quality sensor, wherein one or more parameters representative of the one or more particular environmental conditions at the one or more particular points in time may comprise one or more parameters indicative of one or more aspects of air quality measured at the one or more particular points in time.

In the context of the present patent application, the term "connection," the term "component" and/or similar terms are intended to be physical, but are not necessarily always tangible. Whether or not these terms refer to tangible subject matter, thus, may vary in a particular context of usage. As an example, a tangible connection and/or tangible connection path may be made, such as by a tangible, electrical connection, such as an electrically conductive path comprising metal or other conductor, that is able to conduct electrical current between two tangible components. Likewise, a tangible connection path may be at least partially affected and/or controlled, such that, as is typical, a tangible connection path may be open or closed, at times resulting from influence of one or more externally derived signals, such as external currents and/or voltages, such as for an electrical switch. Non-limiting illustrations of an electrical switch include a transistor, a diode, etc. However, a "connection" and/or "component," in a particular context of usage, likewise, although physical, can also be non-tangible, such as a connection between a client and a server over a network, which generally refers to the ability for the client and server to transmit, receive, and/or exchange communications, as discussed in more detail later. Also, the term "connection" may be utilized in a context of a neural network model, and may, in an embodiment, refer to parameters passed between nodes that may include parameters and/or sets of parameters representative of output values, for example. Also, in an embodiment, connections between nodes may include weight parameters. For example, one or more weight parameters may operate in a specified manner on one or more parameters representative of one or more output values to yield a connection, such as between a node of a first layer and a node of a second layer, in an embodiment, for example.

In a particular context of usage, such as a particular context in which tangible components are being discussed, therefore, the terms "coupled" and "connected" are used in a manner so that the terms are not synonymous. Similar terms may also be used in a manner in which a similar intention is exhibited. Thus, "connected" is used to indicate that two or more tangible components and/or the like, for example, are tangibly in direct physical contact. Thus, using the previous example, two tangible components that are electrically connected are physically connected via a tangible electrical connection, as previously discussed. However, "coupled," is used to mean that potentially two or more tangible components are tangibly in direct physical contact. Nonetheless, is also used to mean that two or more tangible components and/or the like are not necessarily tangibly in direct physical contact, but are able to co-operate, liaise, and/or interact, such as, for example, by being "optically coupled." Likewise, the term "coupled" is also understood to mean indirectly connected. It is further noted, in the context of the present patent application, since memory, such as a memory component and/or memory states, is intended to be non-transitory, the term physical, at least if used in relation to memory necessarily implies that such memory components and/or memory states, continuing with the example, are tangible.

Additionally, in the present patent application, in a particular context of usage, such as a situation in which tangible components (and/or similarly, tangible materials) are being discussed, a distinction exists between being "on" and being "over." As an example, deposition of a substance "on" a substrate refers to a deposition involving direct physical and tangible contact without an intermediary, such as an intermediary substance, between the substance deposited and the substrate in this latter example; nonetheless, deposition "over" a substrate, while understood to potentially include deposition "on" a substrate (since being "on" may also accurately be described as being "over"), is understood to include a situation in which one or more intermediaries, such as one or more intermediary substances, are present between the substance deposited and the substrate so that the substance deposited is not necessarily in direct physical and tangible contact with the substrate.

A similar distinction is made in an appropriate particular context of usage, such as in which tangible materials and/or tangible components are discussed, between being "beneath" and being "under." While "beneath," in such a particular context of usage, is intended to necessarily imply physical and tangible contact (similar to "on," as just described), "under" potentially includes a situation in which there is direct physical and tangible contact, but does not necessarily imply direct physical and tangible contact, such as if one or more intermediaries, such as one or more intermediary substances, are present. Thus, "on" is understood to mean "immediately over" and "beneath" is understood to mean "immediately under."

It is likewise appreciated that terms such as "over" and "under" are understood in a similar manner as the terms "up," "down," "top," "bottom," and so on, previously mentioned. These terms may be used to facilitate discussion, but are not intended to necessarily restrict scope of claimed subject matter. For example, the term "over," as an example, is not meant to suggest that claim scope is limited to only situations in which an embodiment is right side up, such as in comparison with the embodiment being upside down, for example. An example includes a flip chip, as one illustration, in which, for example, orientation at various times (e.g., during fabrication) may not necessarily correspond to orientation of a final product. Thus, if an object, as an example, is within applicable claim scope in a particular orientation, such as upside down, as one example, likewise, it is intended that the latter also be interpreted to be included within applicable claim scope in another orientation, such as right side up, again, as an example, and vice-versa, even if applicable literal claim language has the potential to be interpreted otherwise. Of course, again, as always has been the case in the specification of a patent application, particular context of description and/or usage provides helpful guidance regarding reasonable inferences to be drawn.

Unless otherwise indicated, in the context of the present patent application, the term "or" if used to associate a list, such as A, B, or C, is intended to mean A, B, and C, here used in the inclusive sense, as well as A, B, or C, here used in the exclusive sense. With this understanding, "and" is used in the inclusive sense and intended to mean A, B, and C; whereas "and/or" can be used in an abundance of caution to make clear that all of the foregoing meanings are intended, although such usage is not required. In addition, the term "one or more" and/or similar terms is used to describe any feature, structure, characteristic, and/or the like in the singular, "and/or" is also used to describe a plurality and/or some other combination of features, structures, characteristics, and/or the like. Likewise, the term "based on" and/or similar terms are understood as not necessarily intending to convey an exhaustive list of factors, but to allow for existence of additional factors not necessarily expressly described.

Furthermore, it is intended, for a situation that relates to implementation of claimed subject matter and is subject to testing, measurement, and/or specification regarding degree, to be understood in the following manner. As an example, in a given situation, assume a value of a physical property is to be measured. If alternatively reasonable approaches to testing, measurement, and/or specification regarding degree, at least with respect to the property, continuing with the example, is reasonably likely to occur to one of ordinary skill, at least for implementation purposes, claimed subject matter is intended to cover those alternatively reasonable approaches unless otherwise expressly indicated. As an example, if a plot of measurements over a region is produced and implementation of claimed subject matter refers to employing a measurement of slope over the region, but a variety of reasonable and alternative techniques to estimate the slope over that region exist, claimed subject matter is intended to cover those reasonable alternative techniques unless otherwise expressly indicated.

To the extent claimed subject matter is related to one or more particular measurements, such as with regard to physical manifestations capable of being measured physically, such as, without limit, temperature, pressure, voltage, current, electromagnetic radiation, etc., it is believed that claimed subject matter does not fall with the abstract idea judicial exception to statutory subject matter. Rather, it is asserted, that physical measurements are not mental steps and, likewise, are not abstract ideas.

It is noted, nonetheless, that a typical measurement model employed is that one or more measurements may respectively comprise a sum of at least two components. Thus, for a given measurement, for example, one component may comprise a deterministic component, which in an ideal sense, may comprise a physical value (e.g., sought via one or more measurements), often in the form of one or more signals, signal samples and/or states, and one component may comprise a random component, which may have a variety of sources that may be challenging to quantify. At times, for example, lack of measurement precision may affect a given measurement. Thus, for claimed subject matter, a statistical or stochastic model may be used in addition to a deterministic model as an approach to identification and/or prediction regarding one or more measurement values that may relate to claimed subject matter.

For example, a relatively large number of measurements may be collected to better estimate a deterministic component. Likewise, if measurements vary, which may typically occur, it may be that some portion of a variance may be explained as a deterministic component, while some portion of a variance may be explained as a random component. Typically, it is desirable to have stochastic variance associated with measurements be relatively small, if feasible. That is, typically, it may be preferable to be able to account for a reasonable portion of measurement variation in a deterministic manner, rather than a stochastic matter as an aid to identification and/or predictability.

Along these lines, a variety of techniques have come into use so that one or more measurements may be processed to better estimate an underlying deterministic component, as well as to estimate potentially random components. These techniques, of course, may vary with details surrounding a given situation. Typically, however, more complex problems may involve use of more complex techniques. In this regard, as alluded to above, one or more measurements of physical manifestations may be modeled deterministically and/or stochastically. Employing a model permits collected measurements to potentially be identified and/or processed, and/or potentially permits estimation and/or prediction of an underlying deterministic component, for example, with respect to later measurements to be taken. A given estimate may not be a perfect estimate; however, in general, it is expected that on average one or more estimates may better reflect an underlying deterministic component, for example, if random components that may be included in one or more obtained measurements, are considered. Practically speaking, of course, it is desirable to be able to generate, such as through estimation approaches, a physically meaningful model of processes affecting measurements to be taken.

In some situations, however, as indicated, potential influences may be complex. Therefore, seeking to understand appropriate factors to consider may be particularly challenging. In such situations, it is, therefore, not unusual to employ heuristics with respect to generating one or more estimates. Heuristics refers to use of experience related approaches that may reflect realized processes and/or realized results, such as with respect to use of historical measurements, for example. Heuristics, for example, may be employed in situations where more analytical approaches may be overly complex and/or nearly intractable. Thus, regarding claimed subject matter, an innovative feature may include, in an example embodiment, heuristics that may be employed, for example, to estimate and/or predict one or more measurements.

It is further noted that the terms "type" and/or "like," if used, such as with a feature, structure, characteristic, and/or the like, using "optical" or "electrical" as simple examples, means at least partially of and/or relating to the feature, structure, characteristic, and/or the like in such a way that presence of minor variations, even variations that might otherwise not be considered fully consistent with the feature, structure, characteristic, and/or the like, do not in general prevent the feature, structure, characteristic, and/or the like from being of a "type" and/or being "like," (such as being an "optical-type" or being "optical-like," for example) if the minor variations are sufficiently minor so that the feature, structure, characteristic, and/or the like would still be considered to be substantially present with such variations also present. Thus, continuing with this example, the terms optical-type and/or optical-like properties are necessarily intended to include optical properties. Likewise, the terms electrical-type and/or electrical-like properties, as another example, are necessarily intended to include electrical properties. It should be noted that the specification of the present patent application merely provides one or more illustrative examples and claimed subject matter is intended to not be limited to one or more illustrative examples; however, again, as has always been the case with respect to the specification of a patent application, particular context of description and/or usage provides helpful guidance regarding reasonable inferences to be drawn.

With advances in technology, it has become more typical to employ distributed computing and/or communication approaches in which portions of a process, such as signal processing of signal samples, for example, may be allocated among various devices, including one or more client devices and/or one or more server devices, via a computing and/or communications network, for example. A network may comprise two or more devices, such as network devices and/or computing devices, and/or may couple devices, such as network devices and/or computing devices, so that signal communications, such as in the form of signal packets and/or signal frames (e.g., comprising one or more signal samples), for example, may be exchanged, such as between a server device and/or a client device, as well as other types of devices, including between wired and/or wireless devices coupled via a wired and/or wireless network, for example. An example of a distributed computing system comprises the so-called Hadoop distributed computing system, which employs a map-reduce type of architecture. In the context of the present patent application, the terms map-reduce architecture and/or similar terms are intended to refer to a distributed computing system implementation and/or embodiment for processing and/or for generating larger sets of signal samples employing map and/or reduce operations for a parallel, distributed process performed over a network of devices. A map operation and/or similar terms refer to processing of signals (e.g., signal samples) to generate one or more key-value pairs and to distribute the one or more pairs to one or more devices of the system (e.g., network). A reduce operation and/or similar terms refer to processing of signals (e.g., signal samples) via a summary operation (e.g., such as counting the number of students in a queue, yielding name frequencies, etc.). A system may employ such an architecture, such as by marshaling distributed server devices, executing various tasks in parallel, and/or managing communications, such as signal transfers, between various parts of the system (e.g., network), in an embodiment. As mentioned, one non-limiting, but well-known, example comprises the Hadoop distributed computing system. It refers to an open source implementation and/or embodiment of a map-reduce type architecture (available from the Apache Software Foundation, 1901 Munsey Drive, Forrest Hill, Md., 21050-2747), but may include other aspects, such as the Hadoop distributed file system (HDFS) (available from the Apache Software Foundation, 1901 Munsey Drive, Forrest Hill, Md., 21050-2747). In general, therefore, "Hadoop" and/or similar terms (e.g., "Hadoop-type," etc.) refer to an implementation and/or embodiment of a scheduler for executing larger processing jobs using a map-reduce architecture over a distributed system. Furthermore, in the context of the present patent application, use of the term "Hadoop" is intended to include versions, presently known and/or to be later developed.

In the context of the present patent application, the term network device refers to any device capable of communicating via and/or as part of a network and may comprise a computing device. While network devices may be capable of communicating signals (e.g., signal packets and/or frames), such as via a wired and/or wireless network, they may also be capable of performing operations associated with a computing device, such as arithmetic and/or logic operations, processing and/or storing operations (e.g., storing signal samples), such as in memory as tangible, physical memory states, and/or may, for example, operate as a server device and/or a client device in various embodiments. Network devices capable of operating as a server device, a client device and/or otherwise, may include, as examples, dedicated rack-mounted servers, desktop computers, laptop computers, set top boxes, tablets, netbooks, smart phones, wearable devices, integrated devices combining two or more features of the foregoing devices, and/or the like, or any combination thereof. As mentioned, signal packets and/or frames, for example, may be exchanged, such as between a server device and/or a client device, as well as other types of devices, including between wired and/or wireless devices coupled via a wired and/or wireless network, for example, or any combination thereof. It is noted that the terms, server, server device, server computing device, server computing platform and/or similar terms are used interchangeably. Similarly, the terms client, client device, client computing device, client computing platform and/or similar terms are also used interchangeably. While in some instances, for ease of description, these terms may be used in the singular, such as by referring to a "client device" or a "server device," the description is intended to encompass one or more client devices and/or one or more server devices, as appropriate. Along similar lines, references to a "database" are understood to mean, one or more databases and/or portions thereof, as appropriate.

It should be understood that for ease of description, a network device (also referred to as a networking device) may be embodied and/or described in terms of a computing device and vice-versa. However, it should further be understood that this description should in no way be construed so that claimed subject matter is limited to one embodiment, such as only a computing device and/or only a network device, but, instead, may be embodied as a variety of devices or combinations thereof, including, for example, one or more illustrative examples.

A network may also include now known, and/or to be later developed arrangements, derivatives, and/or improvements, including, for example, past, present and/or future mass storage, such as network attached storage (NAS), a storage area network (SAN), and/or other forms of device readable media, for example. A network may include a portion of the Internet, one or more local area networks (LANs), one or more wide area networks (WANs), wire-line type connections, wireless type connections, other connections, or any combination thereof. Thus, a network may be worldwide in scope and/or extent. Likewise, sub-networks, such as may employ differing architectures and/or may be substantially compliant and/or substantially compatible with differing protocols, such as network computing and/or communications protocols (e.g., network protocols), may interoperate within a larger network.

In the context of the present patent application, the term sub-network and/or similar terms, if used, for example, with respect to a network, refers to the network and/or a part thereof. Sub-networks may also comprise links, such as physical links, connecting and/or coupling nodes, so as to be capable to communicate signal packets and/or frames between devices of particular nodes, including via wired links, wireless links, or combinations thereof. Various types of devices, such as network devices and/or computing devices, may be made available so that device interoperability is enabled and/or, in at least some instances, may be transparent. In the context of the present patent application, the term "transparent," if used with respect to devices of a network, refers to devices communicating via the network in which the devices are able to communicate via one or more intermediate devices, such as of one or more intermediate nodes, but without the communicating devices necessarily specifying the one or more intermediate nodes and/or the one or more intermediate devices of the one or more intermediate nodes and/or, thus, may include within the network the devices communicating via the one or more intermediate nodes and/or the one or more intermediate devices of the one or more intermediate nodes, but may engage in signal communications as if such intermediate nodes and/or intermediate devices are not necessarily involved. For example, a router may provide a link and/or connection between otherwise separate and/or independent LANs.

In the context of the present patent application, a "private network" refers to a particular, limited set of devices, such as network devices and/or computing devices, able to communicate with other devices, such as network devices and/or computing devices, in the particular, limited set, such as via signal packet and/or signal frame communications, for example, without a need for re-routing and/or redirecting signal communications. A private network may comprise a stand-alone network; however, a private network may also comprise a subset of a larger network, such as, for example, without limitation, all or a portion of the Internet. Thus, for example, a private network "in the cloud" may refer to a private network that comprises a subset of the Internet. Although signal packet and/or frame communications (e.g. signal communications) may employ intermediate devices of intermediate nodes to exchange signal packets and/or signal frames, those intermediate devices may not necessarily be included in the private network by not being a source or designated destination for one or more signal packets and/or signal frames, for example. It is understood in the context of the present patent application that a private network may direct outgoing signal communications to devices not in the private network, but devices outside the private network may not necessarily be able to direct inbound signal communications to devices included in the private network.

The Internet refers to a decentralized global network of interoperable networks that comply with the Internet Protocol (IP). It is noted that there are several versions of the Internet Protocol. The term Internet Protocol, IP, and/or similar terms are intended to refer to any version, now known and/or to be later developed. The Internet includes local area networks (LANs), wide area networks (WANs), wireless networks, and/or long haul public networks that, for example, may allow signal packets and/or frames to be communicated between LANs. The term World Wide Web (WWW or Web) and/or similar terms may also be used, although it refers to a part of the Internet that complies with the Hypertext Transfer Protocol (HTTP). For example, network devices may engage in an HTTP session through an exchange of appropriately substantially compatible and/or substantially compliant signal packets and/or frames. It is noted that there are several versions of the Hypertext Transfer Protocol. The term Hypertext Transfer Protocol, HTTP, and/or similar terms are intended to refer to any version, now known and/or to be later developed. It is likewise noted that in various places in this document substitution of the term Internet with the term World Wide Web ("Web") may be made without a significant departure in meaning and may, therefore, also be understood in that manner if the statement would remain correct with such a substitution.

Although claimed subject matter is not in particular limited in scope to the Internet and/or to the Web; nonetheless, the Internet and/or the Web may without limitation provide a useful example of an embodiment at least for purposes of illustration. As indicated, the Internet and/or the Web may comprise a worldwide system of interoperable networks, including interoperable devices within those networks. The Internet and/or Web has evolved to a public, self-sustaining facility accessible to potentially billions of people or more worldwide. Also, in an embodiment, and as mentioned above, the terms "WWW" and/or "Web" refer to a part of the Internet that complies with the Hypertext Transfer Protocol. The Internet and/or the Web, therefore, in the context of the present patent application, may comprise a service that organizes stored digital content, such as, for example, text, images, video, etc., through the use of hypermedia, for example. It is noted that a network, such as the Internet and/or Web, may be employed to store electronic files and/or electronic documents.

The term electronic file and/or the term electronic document are used throughout this document to refer to a set of stored memory states and/or a set of physical signals associated in a manner so as to thereby at least logically form a file (e.g., electronic) and/or an electronic document. That is, it is not meant to implicitly reference a particular syntax, format and/or approach used, for example, with respect to a set of associated memory states and/or a set of associated physical signals. If a particular type of file storage format and/or syntax, for example, is intended, it is referenced expressly. It is further noted an association of memory states, for example, may be in a logical sense and not necessarily in a tangible, physical sense. Thus, although signal and/or state components of a file and/or an electronic document, for example, are to be associated logically, storage thereof, for example, may reside in one or more different places in a tangible, physical memory, in an embodiment.

A Hyper Text Markup Language ("HTML"), for example, may be utilized to specify digital content and/or to specify a format thereof, such as in the form of an electronic file and/or an electronic document, such as a Web page, Web site, etc., for example. An Extensible Markup Language ("XML") may also be utilized to specify digital content and/or to specify a format thereof, such as in the form of an electronic file and/or an electronic document, such as a Web page, Web site, etc., in an embodiment. Of course, HTML and/or XML are merely examples of "markup" languages, provided as non-limiting illustrations. Furthermore, HTML and/or XML are intended to refer to any version, now known and/or to be later developed, of these languages. Likewise, claimed subject matter are not intended to be limited to examples provided as illustrations, of course.

In the context of the present patent application, the term "Web site" and/or similar terms refer to Web pages that are associated electronically to form a particular collection thereof. Also, in the context of the present patent application, "Web page" and/or similar terms refer to an electronic file and/or an electronic document accessible via a network, including by specifying a uniform resource locator (URL) for accessibility via the Web, in an example embodiment. As alluded to above, in one or more embodiments, a Web page may comprise digital content coded (e.g., via computer instructions) using one or more languages, such as, for example, markup languages, including HTML and/or XML, although claimed subject matter is not limited in scope in this respect. Also, in one or more embodiments, application developers may write code (e.g., computer instructions) in the form of JavaScript (or other programming languages), for example, executable by a computing device to provide digital content to populate an electronic document and/or an electronic file in an appropriate format, such as for use in a particular application, for example. Use of the term "JavaScript" and/or similar terms intended to refer to one or more particular programming languages are intended to refer to any version of the one or more programming languages identified, now known and/or to be later developed. Thus, JavaScript is merely an example programming language. As was mentioned, claimed subject matter is not intended to be limited to examples and/or illustrations.

In the context of the present patent application, the terms "entry," "electronic entry," "document," "electronic document," "content,", "digital content," "item," and/or similar terms are meant to refer to signals and/or states in a physical format, such as a digital signal and/or digital state format, e.g., that may be perceived by a user if displayed, played, tactilely generated, etc. and/or otherwise executed by a device, such as a digital device, including, for example, a computing device, but otherwise might not necessarily be readily perceivable by humans (e.g., if in a digital format). Likewise, in the context of the present patent application, digital content provided to a user in a form so that the user is able to readily perceive the underlying content itself (e.g., content presented in a form consumable by a human, such as hearing audio, feeling tactile sensations and/or seeing images, as examples) is referred to, with respect to the user, as "consuming" digital content, "consumption" of digital content, "consumable" digital content and/or similar terms. For one or more embodiments, an electronic document and/or an electronic file may comprise a Web page of code (e.g., computer instructions) in a markup language executed or to be executed by a computing and/or networking device, for example. In another embodiment, an electronic document and/or electronic file may comprise a portion and/or a region of a Web page. However, claimed subject matter is not intended to be limited in these respects.

Also, for one or more embodiments, an electronic document and/or electronic file may comprise a number of components. As previously indicated, in the context of the present patent application, a component is physical, but is not necessarily tangible. As an example, components with reference to an electronic document and/or electronic file, in one or more embodiments, may comprise text, for example, in the form of physical signals and/or physical states (e.g., capable of being physically displayed). Typically, memory states, for example, comprise tangible components, whereas physical signals are not necessarily tangible, although signals may become (e.g., be made) tangible, such as if appearing on a tangible display, for example, as is not uncommon. Also, for one or more embodiments, components with reference to an electronic document and/or electronic file may comprise a graphical object, such as, for example, an image, such as a digital image, and/or sub-objects, including attributes thereof, which, again, comprise physical signals and/or physical states (e.g., capable of being tangibly displayed). In an embodiment, digital content may comprise, for example, text, images, audio, video, and/or other types of electronic documents and/or electronic files, including portions thereof, for example.

Also, in the context of the present patent application, the term parameters (e.g., one or more parameters) refer to material descriptive of a collection of signal samples, such as one or more electronic documents and/or electronic files, and exist in the form of physical signals and/or physical states, such as memory states. For example, one or more parameters, such as referring to an electronic document and/or an electronic file comprising an image, may include, as examples, time of day at which an image was captured, latitude and longitude of an image capture device, such as a camera, for example, etc. In another example, one or more parameters relevant to digital content, such as digital content comprising a technical article, as an example, may include one or more authors, for example. Claimed subject matter is intended to embrace meaningful, descriptive parameters in any format, so long as the one or more parameters comprise physical signals and/or states, which may include, as parameter examples, collection name (e.g., electronic file and/or electronic document identifier name), technique of creation, purpose of creation, time and date of creation, logical path if stored, coding formats (e.g., type of computer instructions, such as a markup language) and/or standards and/or specifications used so as to be protocol compliant (e.g., meaning substantially compliant and/or substantially compatible) for one or more uses, and so forth.

Signal packet communications and/or signal frame communications, also referred to as signal packet transmissions and/or signal frame transmissions (or merely "signal packets" or "signal frames"), may be communicated between nodes of a network, where a node may comprise one or more network devices and/or one or more computing devices, for example. As an illustrative example, but without limitation, a node may comprise one or more sites employing a local network address, such as in a local network address space. Likewise, a device, such as a network device and/or a computing device, may be associated with that node. It is also noted that in the context of this patent application, the term "transmission" is intended as another term for a type of signal communication that may occur in any one of a variety of situations. Thus, it is not intended to imply a particular directionality of communication and/or a particular initiating end of a communication path for the "transmission" communication. For example, the mere use of the term in and of itself is not intended, in the context of the present patent application, to have particular implications with respect to the one or more signals being communicated, such as, for example, whether the signals are being communicated "to" a particular device, whether the signals are being communicated "from" a particular device, and/or regarding which end of a communication path may be initiating communication, such as, for example, in a "push type" of signal transfer or in a "pull type" of signal transfer. In the context of the present patent application, push and/or pull type signal transfers are distinguished by which end of a communications path initiates signal transfer.

Thus, a signal packet and/or frame may, as an example, be communicated via a communication channel and/or a communication path, such as comprising a portion of the Internet and/or the Web, from a site via an access node coupled to the Internet or vice-versa. Likewise, a signal packet and/or frame may be forwarded via network nodes to a target site coupled to a local network, for example. A signal packet and/or frame communicated via the Internet and/or the Web, for example, may be routed via a path, such as either being "pushed" or "pulled," comprising one or more gateways, servers, etc. that may, for example, route a signal packet and/or frame, such as, for example, substantially in accordance with a target and/or destination address and availability of a network path of network nodes to the target and/or destination address. Although the Internet and/or the Web comprise a network of interoperable networks, not all of those interoperable networks are necessarily available and/or accessible to the public.

In the context of the particular patent application, a network protocol, such as for communicating between devices of a network, may be characterized, at least in part, substantially in accordance with a layered description, such as the so-called Open Systems Interconnection (OSI) seven layer type of approach and/or description. A network computing and/or communications protocol (also referred to as a network protocol) refers to a set of signaling conventions, such as for communication transmissions, for example, as may take place between and/or among devices in a network. In the context of the present patent application, the term "between" and/or similar terms are understood to include "among" if appropriate for the particular usage and vice-versa. Likewise, in the context of the present patent application, the terms "compatible with," "comply with" and/or similar terms are understood to respectively include substantial compatibility and/or substantial compliance.

A network protocol, such as protocols characterized substantially in accordance with the aforementioned OSI description, has several layers. These layers are referred to as a network stack. Various types of communications (e.g., transmissions), such as network communications, may occur across various layers. A lowest level layer in a network stack, such as the so-called physical layer, may characterize how symbols (e.g., bits and/or bytes) are communicated as one or more signals (and/or signal samples) via a physical medium (e.g., twisted pair copper wire, coaxial cable, fiber optic cable, wireless air interface, combinations thereof, etc.). Progressing to higher-level layers in a network protocol stack, additional operations and/or features may be available via engaging in communications that are substantially compatible and/or substantially compliant with a particular network protocol at these higher-level layers. For example, higher-level layers of a network protocol may, for example, affect device permissions, user permissions, etc.

A network and/or sub-network, in an embodiment, may communicate via signal packets and/or signal frames, such via participating digital devices and may be substantially compliant and/or substantially compatible with, but is not limited to, now known and/or to be developed, versions of any of the following network protocol stacks: ARCNET, AppleTalk, ATM, Bluetooth, DECnet, Ethernet, FDDI, Frame Relay, HIPPI, IEEE 1394, IEEE 802.11, IEEE-488, Internet Protocol Suite, IPX, Myrinet, OSI Protocol Suite, QsNet, RS-232, SPX, System Network Architecture, Token Ring, USB, and/or X.25. A network and/or sub-network may employ, for example, a version, now known and/or later to be developed, of the following: TCP/IP, UDP, DECnet, NetBEUI, IPX, AppleTalk and/or the like. Versions of the Internet Protocol (IP) may include IPv4, IPv6, and/or other later to be developed versions.

Regarding aspects related to a network, including a communications and/or computing network, a wireless network may couple devices, including client devices, with the network. A wireless network may employ stand-alone, ad-hoc networks, mesh networks, Wireless LAN (WLAN) networks, cellular networks, and/or the like. A wireless network may further include a system of terminals, gateways, routers, and/or the like coupled by wireless radio links, and/or the like, which may move freely, randomly and/or organize themselves arbitrarily, such that network topology may change, at times even rapidly. A wireless network may further employ a plurality of network access technologies, including a version of Long Term Evolution (LTE), WLAN, Wireless Router (WR) mesh, 2nd, 3rd, or 4th generation (2G, 3G, or 4G) cellular technology and/or the like, whether currently known and/or to be later developed. Network access technologies may enable wide area coverage for devices, such as computing devices and/or network devices, with varying degrees of mobility, for example.

A network may enable radio frequency and/or other wireless type communications via a wireless network access technology and/or air interface, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, ultra-wideband (UWB), 802.11b/g/n, and/or the like. A wireless network may include virtually any type of now known and/or to be developed wireless communication mechanism and/or wireless communications protocol by which signals may be communicated between devices, between networks, within a network, and/or the like, including the foregoing, of course.

Figure 19:
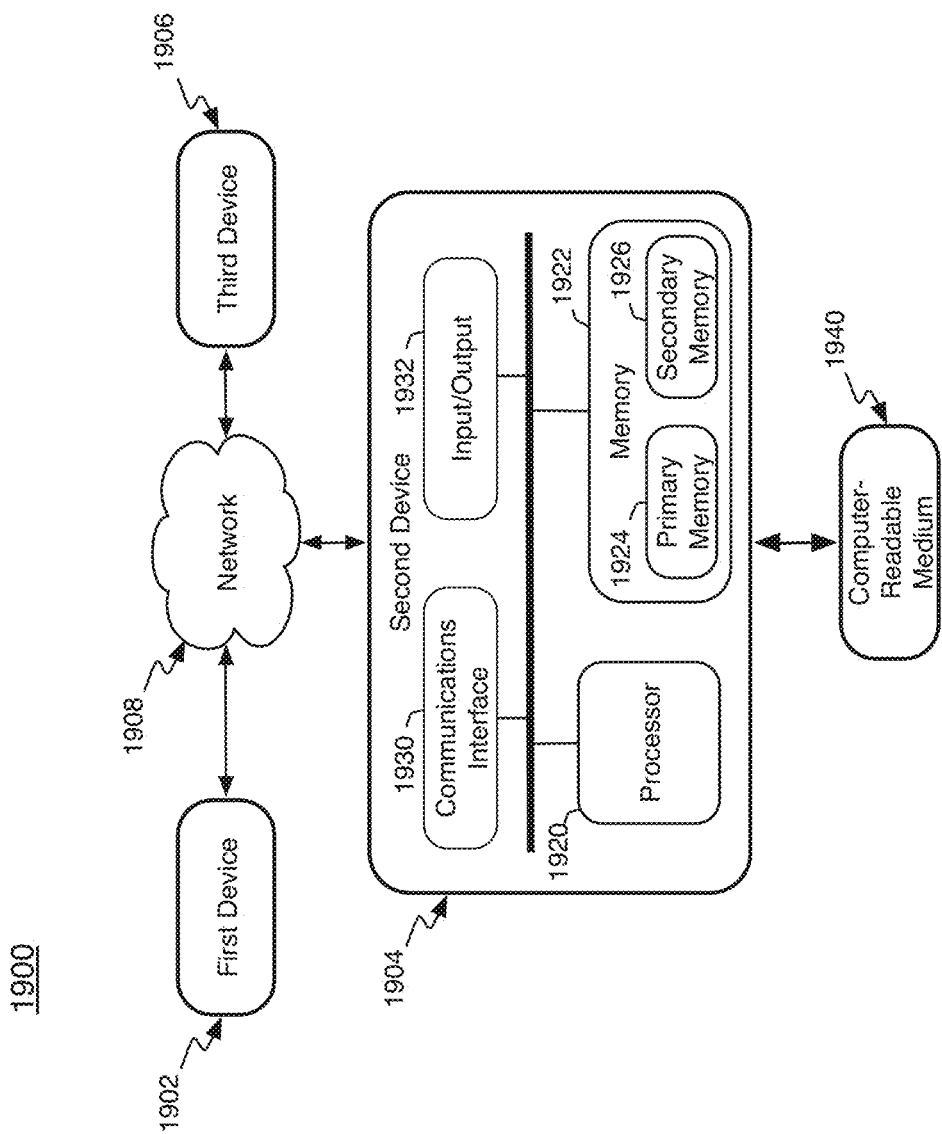
FIG. 19 is a schematic block diagram of an example computing device, in accordance with an embodiment.

In one example embodiment, as shown in FIG. 19, a system embodiment may comprise a local network (e.g., device 904 and medium 940) and/or another type of network, such as a computing and/or communications network. For purposes of illustration, therefore, FIG. 19 shows an embodiment 1900 of a system that may be employed to implement either type or both types of networks. Network 1908 may comprise one or more network connections, links, processes, services, applications, and/or resources to facilitate and/or support communications, such as an exchange of communication signals, for example, between a computing device, such as 1902, and another computing device, such as 1906, which may, for example, comprise one or more client computing devices and/or one or more server computing device. By way of example, but not limitation, network 1908 may comprise wireless and/or wired communication links, telephone and/or telecommunications systems, Wi-Fi networks, Wi-MAX networks, the Internet, a local area network (LAN), a wide area network (WAN), or any combinations thereof.

Example devices in FIG. 19 may comprise features, for example, of a client computing device and/or a server computing device, in an embodiment. One or more computing devices, such as computing devices 1902, 1904, and/or 1906, for example, may be utilized in various embodiments, including example embodiments described herein in connection with FIGS. 1-19. It is further noted that the term computing device, in general, whether employed as a client and/or as a server, or otherwise, refers at least to a processor and a memory connected by a communication bus. Likewise, in the context of the present patent application at least, this is understood to refer to sufficient structure within the meaning of 35 USC § 112 (f) so that it is specifically intended that 35 USC § 112 (f) not be implicated by use of the term "computing device" and/or similar terms; however, if it is determined, for some reason not immediately apparent, that the foregoing understanding cannot stand and that 35 USC § 112 (f), therefore, necessarily is implicated by the use of the term "computing device" and/or similar terms, then, it is intended, pursuant to that statutory section, that corresponding structure, material and/or acts for performing one or more functions be understood and be interpreted to be described at least in FIGS. 1-18, for example, and in the text associated with the foregoing figure(s) of the present patent application.

An embodiment in accordance with claimed subject matter may include a method of executing computer instructions on at least one computing device without further human interaction in which the at least one computing device includes at least one processor and at least one memory. An embodiment may include fetching computer instructions from the at least one memory of the at least one computing device for execution on the at least one processor of the at least one computing device, executing the fetched computer instructions on the at least one processor of the at least one computing device, and storing in the at least one memory of the at least one computing device any results of having executed the fetched computer instructions on the at least one processor of the at least one computing device. In an embodiment, the computer instructions to be executed comprise instructions for processing epigenetic content, wherein executing the fetched instructions further includes obtaining epigenetic content for a particular user representative of a plurality of particular epigenetic states corresponding to respective points in time, tracking behavioral profile content for the particular user over a period of time including the respective points in time, training a machine-learning device, system, or process, or a combination thereof, to identify one or more relationships between one or more particular behaviors and one or more changes in epigenetic state for the particular individual based, at least in part, on the epigenetic content and the behavioral profile content, and identifying a further change in epigenetic state for the particular individual based at least in part on a detected change in behavioral profile content.

In an embodiment, an apparatus may include at least one computing device, the at least one computing device including at least one processor and at least one memory, the at least one computing device to execute computer instructions on the at least one processor without further human intervention. In an embodiment, the computer instructions to be executed may be fetched from the at least one memory for execution on the at least one processor, and the at least one computing device may store in the at least one memory of the at least one computing device any results to be generated from the execution on the at least one processor of the to be executed computer instructions. In an embodiment, the computer instructions to be executed may include instructions for processing epigenetic content wherein the at least one processor to obtain epigenetic content for a particular user representative of a plurality of particular epigenetic states to correspond to respective points in time, track behavioral profile content for the particular user over a period of time to include the respective points in time, train a machine-learning device, system, or process, or a combination thereof, to identify one or more relationships between one or more particular behaviors and one or more changes in epigenetic state for the particular individual based, at least in part, on the epigenetic content and the behavioral profile content, and identify a further change in epigenetic state for the particular individual based at least in part on a detected change in behavioral profile content.

Referring now again to FIG. 19, in an embodiment, first and third devices 1902 and 1906 may be capable of rendering a graphical user interface (GUI) for a network device and/or a computing device, for example, so that a user-operator may engage in system use. Device 1904 may potentially serve a similar function in this illustration. Likewise, in FIG. 19, computing device 1902 ('first device' in figure) may interface with computing device 1904 ('second device' in figure), which may, for example, also comprise features of a client computing device and/or a server computing device, in an embodiment. Processor (e.g., processing device) 1920 and memory 1922, which may comprise primary memory 1924 and secondary memory 1926, may communicate by way of a communication bus 1915, for example. The term "computing device," in the context of the present patent application, refers to a system and/or a device, such as a computing apparatus, that includes a capability to process (e.g., perform computations) and/or store digital content, such as electronic files, parameters, electronic documents, measurements, text, images, video, audio, etc. in the form of signals and/or states. Thus, a computing device, in the context of the present patent application, may comprise hardware, software, firmware, or any combination thereof (other than software per se). Computing device 1904, as depicted in FIG. 19, is merely one example, and claimed subject matter is not limited in scope to this particular example.

As mentioned, for one or more embodiments, a computing device may comprise, for example, any of a wide range of digital electronic devices, including, but not limited to, desktop and/or notebook computers, high-definition televisions, digital versatile disc (DVD) and/or other optical disc players and/or recorders, game consoles, satellite television receivers, cellular telephones, tablet devices, wearable devices, personal digital assistants, mobile audio and/or video playback and/or recording devices, or any combination of the foregoing. Further, unless specifically stated otherwise, a process as described, such as with reference to flow diagrams and/or otherwise, may also be executed and/or affected, in whole or in part, by a computing device and/or a network device. A device, such as a computing device and/or network device, may vary in terms of capabilities and/or features. Claimed subject matter is intended to cover a wide range of potential variations. For example, a device may include a numeric keypad and/or other display of limited functionality, such as a monochrome liquid crystal display (LCD) for displaying text, for example. In contrast, however, as another example, a web-enabled device may include a physical and/or a virtual keyboard, mass storage, one or more accelerometers, one or more gyroscopes, global positioning system (GPS) and/or other location-identifying type capability, and/or a display with a higher degree of functionality, such as a touch-sensitive color 2D or 3D display, for example.

As suggested previously, communications between a computing device and/or a network device and a wireless network may be in accordance with known and/or to be developed network protocols including, for example, global system for mobile communications (GSM), enhanced data rate for GSM evolution (EDGE), 802.11b/g/n/h, etc., and/or worldwide interoperability for microwave access (Wi-MAX). A computing device and/or a networking device may also have a subscriber identity module (SIM) card, which, for example, may comprise a detachable or embedded smart card that is able to store subscription content of a user, and/or is also able to store a contact list. A user may own the computing device and/or network device or may otherwise be a user, such as a primary user, for example. A device may be assigned an address by a wireless network operator, a wired network operator, and/or an Internet Service Provider (ISP). For example, an address may comprise a domestic or international telephone number, an Internet Protocol (IP) address, and/or one or more other identifiers. In other embodiments, a computing and/or communications network may be embodied as a wired network, wireless network, or any combinations thereof.

A computing and/or network device may include and/or may execute a variety of now known and/or to be developed operating systems, derivatives and/or versions thereof, including computer operating systems, such as Windows, iOS, Linux, a mobile operating system, such as iOS, Android, Windows Mobile, and/or the like. A computing device and/or network device may include and/or may execute a variety of possible applications, such as a client software application enabling communication with other devices. For example, one or more messages (e.g., content) may be communicated, such as via one or more protocols, now known and/or later to be developed, suitable for communication of email, short message service (SMS), and/or multimedia message service (MMS), including via a network, such as a social network, formed at least in part by a portion of a computing and/or communications network, including, but not limited to, Facebook, LinkedIn, Twitter, Flickr, and/or Google+, to provide only a few examples. A computing and/or network device may also include executable computer instructions to process and/or communicate digital content, such as, for example, textual content, digital multimedia content, and/or the like. A computing and/or network device may also include executable computer instructions to perform a variety of possible tasks, such as browsing, searching, playing various forms of digital content, including locally stored and/or streamed video, and/or games such as, but not limited to, fantasy sports leagues. The foregoing is provided merely to illustrate that claimed subject matter is intended to include a wide range of possible features and/or capabilities.

In FIG. 19, computing device 1902 may provide one or more sources of executable computer instructions in the form physical states and/or signals (e.g., stored in memory states), for example. Computing device 1902 may communicate with computing device 1904 by way of a network connection, such as via network 1908, for example. As previously mentioned, a connection, while physical, may not necessarily be tangible. Although computing device 1904 of FIG. 19 shows various tangible, physical components, claimed subject matter is not limited to a computing devices having only these tangible components as other implementations and/or embodiments may include alternative arrangements that may comprise additional tangible components or fewer tangible components, for example, that function differently while achieving similar results. Rather, examples are provided merely as illustrations. It is not intended that claimed subject matter be limited in scope to illustrative examples.

Memory 1922 may comprise any non-transitory storage mechanism. Memory 1922 may comprise, for example, primary memory 1924 and secondary memory 1926, additional memory circuits, mechanisms, or combinations thereof may be used. Memory 1922 may comprise, for example, random access memory, read only memory, etc., such as in the form of one or more storage devices and/or systems, such as, for example, a disk drive including an optical disc drive, a tape drive, a solid-state memory drive, etc., just to name a few examples.

Memory 1922 may be utilized to store a program of executable computer instructions. For example, processor 1920 may fetch executable instructions from memory and proceed to execute the fetched instructions. Memory 1922 may also comprise a memory controller for accessing device readable-medium 1940 that may carry and/or make accessible digital content, which may include code, and/or instructions, for example, executable by processor 1920 and/or some other device, such as a controller, as one example, capable of executing computer instructions, for example. Under direction of processor 1920, a non-transitory memory, such as memory cells storing physical states (e.g., memory states), comprising, for example, a program of executable computer instructions, may be executed by processor 1920 and able to generate signals to be communicated via a network, for example, as previously described. Generated signals may also be stored in memory, also previously suggested.

Memory 1922 may store electronic files and/or electronic documents, such as relating to one or more users, and may also comprise a computer-readable medium that may carry and/or make accessible content, including code and/or instructions, for example, executable by processor 1920 and/or some other device, such as a controller, as one example, capable of executing computer instructions, for example. As previously mentioned, the term electronic file and/or the term electronic document are used throughout this document to refer to a set of stored memory states and/or a set of physical signals associated in a manner so as to thereby form an electronic file and/or an electronic document. That is, it is not meant to implicitly reference a particular syntax, format and/or approach used, for example, with respect to a set of associated memory states and/or a set of associated physical signals. It is further noted an association of memory states, for example, may be in a logical sense and not necessarily in a tangible, physical sense. Thus, although signal and/or state components of an electronic file and/or electronic document, are to be associated logically, storage thereof, for example, may reside in one or more different places in a tangible, physical memory, in an embodiment.

Algorithmic descriptions and/or symbolic representations are examples of techniques used by those of ordinary skill in the signal processing and/or related arts to convey the substance of their work to others skilled in the art. An algorithm is, in the context of the present patent application, and generally, is considered to be a self-consistent sequence of operations and/or similar signal processing leading to a desired result. In the context of the present patent application, operations and/or processing involve physical manipulation of physical quantities. Typically, although not necessarily, such quantities may take the form of electrical and/or magnetic signals and/or states capable of being stored, transferred, combined, compared, processed and/or otherwise manipulated, for example, as electronic signals and/or states making up components of various forms of digital content, such as signal measurements, text, images, video, audio, etc.

It has proven convenient at times, principally for reasons of common usage, to refer to such physical signals and/or physical states as bits, values, elements, parameters, symbols, characters, terms, numbers, numerals, measurements, content and/or the like. It should be understood, however, that all of these and/or similar terms are to be associated with appropriate physical quantities and are merely convenient labels. Unless specifically stated otherwise, as apparent from the preceding discussion, it is appreciated that throughout this specification discussions utilizing terms such as "processing," "computing," "calculating," "determining", "establishing", "obtaining", "identifying", "selecting", "generating", and/or the like may refer to actions and/or processes of a specific apparatus, such as a special purpose computer and/or a similar special purpose computing and/or network device. In the context of this specification, therefore, a special purpose computer and/or a similar special purpose computing and/or network device is capable of processing, manipulating and/or transforming signals and/or states, typically in the form of physical electronic and/or magnetic quantities, within memories, registers, and/or other storage devices, processing devices, and/or display devices of the special purpose computer and/or similar special purpose computing and/or network device. In the context of this particular patent application, as mentioned, the term "specific apparatus" therefore includes a general purpose computing and/or network device, such as a general purpose computer, once it is programmed to perform particular functions, such as pursuant to program software instructions.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and/or storage of charge or a release of stored charge. Likewise, in other memory devices, a change of state may comprise a physical change, such as a transformation in magnetic orientation. Likewise, a physical change may comprise a transformation in molecular structure, such as from crystalline form to amorphous form or vice-versa. In still other memory devices, a change in physical state may involve quantum mechanical phenomena, such as, superposition, entanglement, and/or the like, which may involve quantum bits (qubits), for example. The foregoing is not intended to be an exhaustive list of all examples in which a change in state from a binary one to a binary zero or vice-versa in a memory device may comprise a transformation, such as a physical, but non-transitory, transformation. Rather, the foregoing is intended as illustrative examples.

Referring again to FIG. 19, processor 1920 may comprise one or more circuits, such as digital circuits, to perform at least a portion of a computing procedure and/or process. By way of example, but not limitation, processor 1920 may comprise one or more processors, such as controllers, microprocessors, microcontrollers, application specific integrated circuits, digital signal processors, programmable logic devices, field programmable gate arrays, the like, or any combination thereof. In various implementations and/or embodiments, processor 1920 may perform signal processing, typically substantially in accordance with fetched executable computer instructions, such as to manipulate signals and/or states, to construct signals and/or states, etc., with signals and/or states generated in such a manner to be communicated and/or stored in memory, for example.

FIG. 19 also illustrates device 1904 as including a component 1932 operable with input/output devices, for example, so that signals and/or states may be appropriately communicated between devices, such as device 1904 and an input device and/or device 1904 and an output device. A user may make use of an input device, such as a computer mouse, stylus, track ball, keyboard, and/or any other similar device capable of receiving user actions and/or motions as input signals. Likewise, a user may make use of an output device, such as a display, a printer, etc., and/or any other device capable of providing signals and/or generating stimuli for a user, such as visual stimuli, audio stimuli and/or other similar stimuli.

In the preceding description, various aspects of claimed subject matter have been described. For purposes of explanation, specifics, such as amounts, systems and/or configurations, as examples, were set forth. In other instances, well-known features were omitted and/or simplified so as not to obscure claimed subject matter. While certain features have been illustrated and/or described herein, many modifications, substitutions, changes and/or equivalents will now occur to those skilled in the art. It is, therefore, to be understood that the appended claims are intended to cover all modifications and/or changes as fall within claimed subject matter.

What is claimed is:

1. An apparatus, comprising:
   at least one communication interface of a portable computing device to establish a communication connection between the portable computing device and a server computing device; and
   at least one processor of the portable computing device to:
   obtain, at least in part via the at least one communication interface, one or more signal packets representative of one or more communication, security, and/or cryptographic parameters from the server computing device, wherein the one or more communication, security, and/or cryptographic parameters to enable, at least in part, one or more external computing devices to read from and/or write to a database of the server computing device to contain particular omic and/or environmental content associated with a particular user;
   initiate storage of the one or more communication, security, and/or cryptographic parameters in at least one memory of the portable computing device;
   detect, at least in part via the at least one communication interface, a signal transmitted by a particular external device of the one or more external computing devices;
   establish, at least in part via the at least one communication interface, a communication connection between the portable computing device and the particular external device; and
   initiate transmission, at least in part via the at least one communication interface, of one or more additional signal packets representative of the one or more communication, security, and/or cryptographic parameters to the particular external device at least in part in response to a detection of the communication connection between the portable computing device and the particular external device, wherein the one or more communication, security, and/or cryptographic parameters to enable, at least in part, the particular external device to read from and/or write to the database of the server computing device containing the particular omic and/or environmental content associated with the particular user, wherein the particular omic and/or environmental content associated with the particular user is logically and/or physically partitioned within the database of the server computing device as a bio-ledger and a biosphere ledger, and wherein one or more security tokens of the one or more communication, security, and/or cryptographic parameters to provide, at least in part, a first set of particular authorizations with respect to read and/or write access for particular entries of the bio-ledger associated with the particular user, and wherein the one or more security tokens further to provide, at least in part, a second set of particular authorizations with respect to read and/or write access for particular entries of the biosphere ledger associated with the particular user.

2. The apparatus of claim 1, wherein, to obtain the one or more signal packets representative of the one or more communication, security, and/or cryptographic parameters from the server computing device, the at least one processor to obtain, at least in part via the at least one communication interface, the one or more signal packets via a wired connection with the server computing device.

3. The apparatus of claim 1, wherein the at least one communication interface to include a wireless communication interface, wherein, to detect the signal transmitted by the particular external device, the wireless communication interface to acquire one or more wireless signals transmitted by the particular external device.

4. The apparatus of claim 1, wherein the at least one communication interface to include a wired communication interface, wherein, to detect the signal transmitted by the particular external device, the wired communication interface to detect a physical connection of the personal computing device to the particular external device.

5. The apparatus of claim 1, further comprising a user interface, wherein the at least one processor to obtain an input from the particular user whereby the particular user to indicate authorization of the particular external device, wherein the at least one processor to, via the at least one communication interface, initiate transmission of the one or more additional signal packets representative of the one or more communication, security, and/or cryptographic parameters to the external device at least in part in response to the user input.

6. The apparatus of claim 5, wherein the user interface to comprise implicit bio-authorization, and wherein the at least one processor to initiate transmission of the one or more additional signal packets representative of the one or more communication, security, and/or cryptographic parameters to the external device at least in part in response to an authentication, utilizing at least in part the at least one processor, via the implicit bio-authorization.

7. The apparatus of claim 1, wherein the at least one processor to obtain, at least in part via the at least one communication interface, one or more signal packets representative of one or more doctor directives, medical diagnoses and/or actionable omic content for the particular user from the server computing device, wherein the at least one processor to initiate transmission, at least in part via the at least one communication interface, of the one or more signal packets representative of the one or more doctor directives, medical diagnoses, and/or actionable omic content to the particular external device at least in part in response to a user indication of authorization of the particular external device.

8. The apparatus of claim 1, wherein the at least one processor to obtain, at least in part via the at least one communication interface, one or more signal packets representative of one or more doctor directives, medical diagnoses and/or actionable omic content for the particular user from the external computing device, wherein the at least one processor to initiate transmission, at least in part via the at least one communication interface, of the one or more signal packets representative of the one or more doctor directives, medical diagnoses, and/or actionable omic content to the secure storage device at least in part in response to a user indication of authorization of the secure storage device.

9. The apparatus of claim 1, wherein the at least one processor to obtain, at least in part via the at least one communication interface, from the particular external device one or more signal packets representative of one or more omic, environmental, and/or behavioral parameters for the particular user generated at least in part via the particular external device, wherein the at least one processor to initiate storage of the one or more omic, environmental, and/or behavioral parameters in the at least one memory, and wherein the at least one processor to initiate transmission at least in part via the at least one communication interface of the one or more signal packets representative of the one or more omic, environmental, and/or behavioral parameters generated at least in part by the particular external device to the server computing device, wherein the one or more omic, environmental, and/or behavioral parameters generated at least in part by the particular external device to be stored in the bio-ledger and/or the biosphere ledger for the particular user.

10. The apparatus of claim 1, wherein the portable computing device to comprise an intermediary device, wherein the server computing device to comprise a secure storage device, and wherein the particular external device to comprise a bio-smart device.

11. A method, comprising:
establishing a communication connection between a portable computing device and a server computing device utilizing, at least in part, at least one processor of the portable computing device;
receiving, via at least one communication interface of the portable computing device, one or more signal packets representative of one or more communication, security, and/or cryptographic parameters from the server computing device, wherein the one or more communication, security, and/or cryptographic parameters to enable, at least in part, one or more external computing devices to read from and/or write to a database of the server computing device containing particular omic and/or environmental content associated with a particular user;
storing the one or more communication, security, and/or cryptographic parameters in at least one memory of the portable computing device; and
detecting, at least in part via the at least one processor, a signal transmitted by a particular external device of the one or more external computing devices;
establishing a communication connection between the portable computing device and the particular external device utilizing, at least in part, the at least one processor and the at least one communication interface;
transmitting, via the communication interface, one or more additional signal packets representative of the one or more communication, security, and/or cryptographic parameters to the particular external device at least in part in response to the establishing the communication connection between the portable computing device and the particular external device by the at least one processor, wherein the one or more communication, security, and/or cryptographic parameters to enable, at least in part, the particular external device to read from and/or write to the database of the server computing device containing the particular omic and/or environmental content associated with the particular user;

obtaining, via the at least one processor, one or more signal packets representative of one or more doctor directives, medical diagnoses, and/or actionable omic content for the particular user from the server computing device; and transmitting, at least in part via the at least one communication interface at least in part in connection with the at least one processor, the one or more signal packets representative of one or more doctor directives, medical diagnoses, and/or actionable omic content to the particular external device at least in part in response to a user indication of authorization of the particular external device.

12. The method of claim 11, wherein the receiving the one or more signal packets representative of the one or more communication, security, and/or cryptographic parameters from the server computing device includes receiving, via the at least one communication interface, the one or more signal packets via a wired connection with the server computing device.

13. The method of claim 11, wherein the detecting the signal transmitted by the particular external device includes acquiring, at least in part via the wireless communication interface, one or more wireless signals transmitted by the particular external device.

14. The method of claim 11, wherein the at least one communication interface to include a wired communication interface, and wherein the detecting the signal transmitted by the particular external device includes detecting, at least in part via the wired communication interface, a physical connection of the personal computing device to the particular external device.

15. The method of claim 11, wherein the transmitting the one or more additional signal packets to the particular external device comprises transmitting the one or more additional signal packets responsive at least in part to an input obtained via a user interface of the portable computing device from the particular user whereby the particular user indicates authorization of the particular external device.

16. The method of claim 15, wherein the user interface to comprise bio-authorization circuitry, and wherein the transmitting the one or more additional signal packets to the particular external device includes initiating the transmission at least in part in response to an authentication via the bio-authorization circuitry.

17. The method of claim 11, further comprising:
receiving, at least in part via the at least one communication interface, one or more signal packets representative of one or more doctor directives, medical diagnoses, and/or actionable omic content for the particular user from the particular external computing device; and transmitting, at least in part via the at least one communication interface at least in part in connection with the at least one processor, the one or more signal packets representative of one or more doctor directives, medical diagnoses, and/or actionable omic content to the secure storage device at least in part in response to a user indication of authorization of the particular external device.

18. The method of claim 11, wherein the particular omic, environmental, and/or behavioral content associated with the particular user is logically and/or physically partitioned within the database of the server computing device as a bio-ledger and a biosphere ledger, and the method further comprising:

receiving from the particular external device at least in part via the at least one communication interface one or more signal packets representative of one or more omic, environmental, and/or behavioral parameters for the particular user generated at least in part via the particular external device;

storing the one or more omic, environmental, and/or behavioral parameters in the at least one memory; and transmitting, at least in part via the at least one communication interface, the one or more signal packets representative of the one or more omic, environmental, and/or behavioral parameters generated at least in part by the particular external device to the server computing device, wherein the one or more omic, environmental, and/or behavioral parameters generated at least in part by the particular external device to be stored in the bio-ledger and/or the biosphere ledger for the particular user.

19. The method of claim 11, wherein the portable computing device comprises an intermediary device, wherein the server computing device comprises a secure storage device, and wherein the particular external device comprises a bio-smart device.

20. An apparatus, comprising:
at least one communication interface of a portable computing device to establish a communication connection between the portable computing device and a server computing device;

a user interface of the portable computing device to comprise implicit bio-authorization circuitry; and at least one processor of the portable computing device to:
obtain, at least in part via the at least one communication interface, one or more signal packets representative of one or more communication, security, and/or cryptographic parameters from the server computing device, wherein the one or more communication, security, and/or cryptographic parameters to enable, at least in part, one or more external computing devices to read from and/or write to a database of the server computing device to contain particular omic and/or environmental content associated with a particular user;

initiate storage of the one or more communication, security, and/or cryptographic parameters in at least one memory of the portable computing device;

detect, at least in part via the at least one communication interface, a signal transmitted by a particular external device of the one or more external computing devices;

establish, at least in part via the at least one communication interface, a communication connection between the portable computing device and the particular external device; and initiate transmission, at least in part via the at least one communication interface, of one or more additional signal packets representative of the one or more communication, security, and/or cryptographic parameters to the particular external device at least in part in response to a detection of the communication connection between the portable computing device and the particular external device and at least in part in response to an input obtained from the particular user via the user interface bio-authorization circuitry whereby the particular user to indicate authorization of the particular external device, wherein the one or more communication, security, and/or cryptographic parameters to enable, at least in part, the particular external device to read from and/or write to the database of the server computing device containing the particular omic and/or environmental content associated with the particular user.

* * * * *